(12) United States Patent
Korfhage et al.

(10) Patent No.: US 8,309,303 B2
(45) Date of Patent: Nov. 13, 2012

(54) REVERSE TRANSCRIPTION AND AMPLIFICATION OF RNA WITH SIMULTANEOUS DEGRADATION OF DNA

(75) Inventors: Christian Korfhage, Langenfeld (DE); Ralf Peist, Hilden (DE); Dirk Löffert, Düsseldorf (DE)

(73) Assignee: QIAGEN GmbH, Hilden (DE)

( * ) Notice: Subject to any disclaimer, the term of this patent is extended or adjusted under 35 U.S.C. 154(b) by 673 days.

(21) Appl. No.: 11/887,678

(22) PCT Filed: Mar. 27, 2006

(86) PCT No.: PCT/EP2006/002771
§ 371 (c)(1),
(2), (4) Date: Oct. 6, 2009

(87) PCT Pub. No.: WO2006/103039
PCT Pub. Date: Oct. 5, 2006

(65) Prior Publication Data
US 2010/0015602 A1    Jan. 21, 2010

(30) Foreign Application Priority Data

Apr. 1, 2005  (EP) .................................... 05007157

(51) Int. Cl.
*C12Q 1/68* (2006.01)
*C12P 19/34* (2006.01)
*C07H 21/00* (2006.01)
*C07H 21/02* (2006.01)
*C07H 21/04* (2006.01)

(52) U.S. Cl. ...... 435/6.1; 435/91.2; 536/22.1; 536/23.1; 536/24.3

(58) Field of Classification Search ............. 435/6, 91.2, 435/6.1; 536/22.1, 23.1, 24.3
See application file for complete search history.

(56) References Cited

U.S. PATENT DOCUMENTS

| | | |
|---|---|---|
| 2,264,423 A | 12/1941 | Wingenroth |
| 3,395,018 A | 7/1968 | Read |
| 3,654,090 A | 4/1972 | Wilhelmus et al. |
| 3,687,808 A | 8/1972 | Merigan, Jr. et al. |
| 3,921,105 A | 11/1975 | Brgelz |
| 3,983,421 A | 9/1976 | Yogore |
| 3,995,018 A | 11/1976 | Sjoquist |
| 4,299,916 A | 11/1981 | Litman et al. |
| 4,469,863 A | 9/1984 | Ts'o et al. |
| 4,476,301 A | 10/1984 | Imbach et al. |
| 4,748,111 A | 5/1988 | Dattagupta et al. |
| 4,816,567 A | 3/1989 | Cabilly et al. |
| 4,837,003 A | 6/1989 | Nicolotti |
| 4,845,205 A | 7/1989 | Huynh Dinh et al. |
| 4,883,750 A | 11/1989 | Whiteley et al. |
| 4,937,183 A | 6/1990 | Ultee et al. |
| 4,940,670 A | 7/1990 | Rhodes |
| 4,965,188 A | 10/1990 | Mullis et al. |
| 4,981,957 A | 1/1991 | Lebleu et al. |
| 4,994,373 A | 2/1991 | Stavrianopoulos et al. |
| 4,994,557 A | 2/1991 | Kassis et al. |
| 5,001,050 A | 3/1991 | Blanco et al. |
| 5,023,243 A | 6/1991 | Tullis |
| 5,034,506 A | 7/1991 | Summerton et al. |
| 5,043,272 A | 8/1991 | Hartley |
| 5,106,727 A | 4/1992 | Hartley et al. |
| 5,118,800 A | 6/1992 | Smith et al. |
| 5,130,238 A | 7/1992 | Malek et al. |
| 5,130,302 A | 7/1992 | Spielvogel et al. |
| 5,134,066 A | 7/1992 | Rogers et al. |
| 5,137,806 A | 8/1992 | LeMaistre et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,187,060 A | 2/1993 | Cerutti et al. |
| 5,188,897 A | 2/1993 | Suhadolnik et al. |
| 5,198,543 A | 3/1993 | Blanco et al. |
| 5,214,134 A | 5/1993 | Weis et al. |
| 5,216,141 A | 6/1993 | Benner |
| 5,235,033 A | 8/1993 | Summerton et al. |
| 5,242,794 A | 9/1993 | Whiteley et al. |
| 5,262,311 A | 11/1993 | Pardee et al. |
| 5,264,423 A | 11/1993 | Cohen et al. |
| 5,264,562 A | 11/1993 | Matteucci |
| 5,264,564 A | 11/1993 | Matteucci |
| 5,264,567 A | 11/1993 | Numata et al. |
| 5,268,486 A | 12/1993 | Waggoner et al. |
| 5,273,638 A | 12/1993 | Konrad et al. |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |

(Continued)

FOREIGN PATENT DOCUMENTS

| | | |
|---|---|---|
| AU | 84173/91 | 2/1992 |
| AU | 649066 | 5/1994 |
| AU | 5850996 | 11/1996 |
| AU | 714486 | 1/2000 |
| AU | 749560 | 6/2002 |

(Continued)

OTHER PUBLICATIONS

Breslow et al., Effects of metal ions, including Mg2+ and lanthanides, on the cleavage of ribonucleotides and RNA model compounds. PNAS 88 : 4080 (1991).*

Das et al. Full-length cDNAs: more than just reaching the ends. Physiological Genomics 6 : 57 (2001).*

Dostie et al. Numerous microRNPs in neuronal cells containing novel microRNAs. RNA 9 : 180 (2003).*

(Continued)

*Primary Examiner* — Ethan C Whisenant
(74) *Attorney, Agent, or Firm* — Ballard Spahr LLP

(57) ABSTRACT

The invention relates to a method for processing RNA, in particular, a RNA reaction method and kits for carrying out said RNA reaction method.

15 Claims, 5 Drawing Sheets

U.S. PATENT DOCUMENTS

Figure 1:
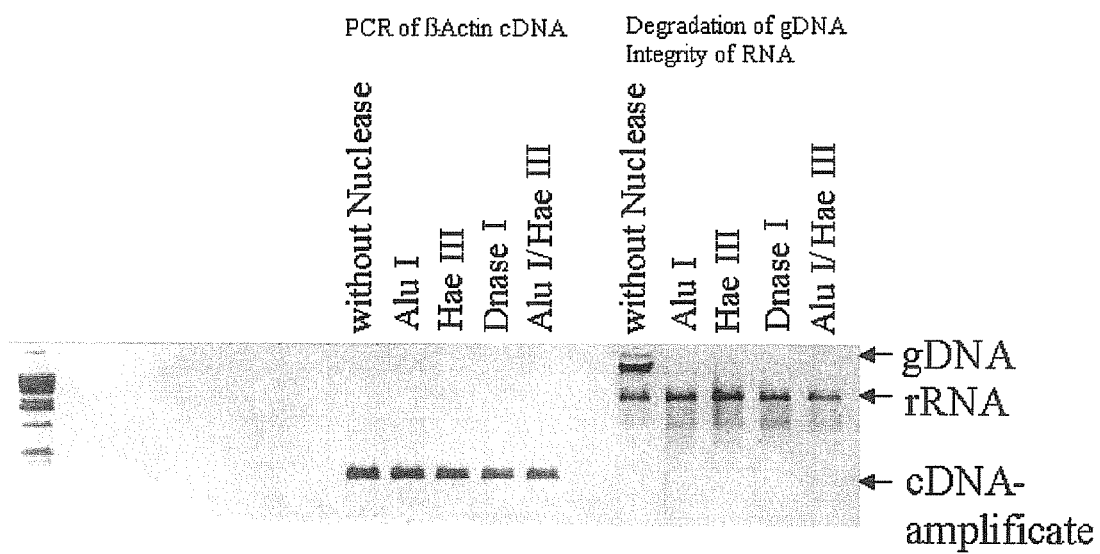

| | | |
|---|---|---|
| 5,321,131 A | 6/1994 | Agrawal et al. |
| 5,328,824 A | 7/1994 | Ward et al. |
| 5,334,711 A | 8/1994 | Sproat et al. |
| 5,354,668 A | 10/1994 | Auerbach |
| 5,359,044 A | 10/1994 | Cook et al. |
| 5,367,066 A | 11/1994 | Urdea et al. |
| 5,367,069 A | 11/1994 | Beck et al. |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,409,818 A | 4/1995 | Davey et al. |
| 5,412,087 A | 5/1995 | McGall et al. |
| 5,427,930 A | 6/1995 | Birkenmeyer et al. |
| 5,429,807 A | 7/1995 | Matson et al. |
| 5,432,272 A | 7/1995 | Benner |
| 5,434,257 A | 7/1995 | Matteucci et al. |
| 5,443,986 A | 8/1995 | Haughland et al. |
| 5,445,934 A | 8/1995 | Fodor et al. |
| 5,446,137 A | 8/1995 | Maag et al. |
| 5,451,067 A | 9/1995 | Pieper |
| 5,451,203 A | 9/1995 | Lamb |
| 5,453,496 A | 9/1995 | Caruthers et al. |
| 5,455,166 A | 10/1995 | Walker |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,427 A | 12/1995 | Fujima |
| 5,476,786 A | 12/1995 | Huston |
| 5,476,925 A | 12/1995 | Letsinger et al. |
| 5,484,908 A | 1/1996 | Froehler et al. |
| 5,489,677 A | 2/1996 | Sanghvi et al. |
| 5,500,341 A | 3/1996 | Spears |
| 5,502,177 A | 3/1996 | Matteucci et al. |
| 5,510,270 A | 4/1996 | Fodor et al. |
| 5,514,785 A | 5/1996 | Van Ness et al. |
| 5,516,134 A | 5/1996 | Crawford et al. |
| 5,516,663 A | 5/1996 | Backman et al. |
| 5,516,664 A | 5/1996 | Hyman |
| 5,519,126 A | 5/1996 | Hecht |
| 5,519,134 A | 5/1996 | Acevedo et al. |
| 5,521,065 A | 5/1996 | Whiteley et al. |
| 5,523,204 A | 6/1996 | Singer et al. |
| 5,525,711 A | 6/1996 | Hawkins et al. |
| 5,536,821 A | 7/1996 | Agrawal et al. |
| 5,538,871 A | 7/1996 | Nuovo et al. |
| 5,539,082 A | 7/1996 | Nielsen et al. |
| 5,541,306 A | 7/1996 | Agrawal et al. |
| 5,541,307 A | 7/1996 | Cook et al. |
| 5,547,843 A | 8/1996 | Studier et al. |
| 5,550,111 A | 8/1996 | Suhadolnik et al. |
| 5,552,540 A | 9/1996 | Haralambidis |
| 5,556,748 A | 9/1996 | Douglas |
| 5,556,771 A | 9/1996 | Shen et al. |
| 5,556,772 A | 9/1996 | Sorge et al. |
| 5,561,045 A | 10/1996 | Dorval et al. |
| 5,561,225 A | 10/1996 | Maddry et al. |
| 5,563,037 A | 10/1996 | Sutherland et al. |
| 5,563,253 A | 10/1996 | Agrawal et al. |
| 5,563,912 A | 10/1996 | Yasunaga et al. |
| 5,565,339 A | 10/1996 | Bloch et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,609 A | 1/1997 | Auerbach |
| 5,591,722 A | 1/1997 | Montgomery et al. |
| 5,593,836 A | 1/1997 | Niemiec et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,599,695 A | 2/1997 | Pease et al. |
| 5,599,921 A | 2/1997 | Sorge et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,389 A | 3/1997 | Auerbach |
| 5,614,390 A | 3/1997 | McCaslin et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,629,158 A | 5/1997 | Uhlen |
| 5,629,179 A | 5/1997 | Mierendorf et al. |
| 5,633,360 A | 5/1997 | Bischofberger et al. |
| 5,635,602 A | 6/1997 | Cantor et al. |
| 5,639,599 A | 6/1997 | Ryder et al. |
| 5,639,873 A | 6/1997 | Barascut et al. |
| 5,646,265 A | 7/1997 | McGee |
| 5,648,213 A | 7/1997 | Reddy et al. |
| 5,648,245 A | 7/1997 | Fire et al. |
| 5,654,413 A | 8/1997 | Brenner |
| 5,658,873 A | 8/1997 | Bertsch-Frank et al. |
| 5,663,312 A | 9/1997 | Chaturvedula |
| 5,665,539 A | 9/1997 | Sano et al. |
| 5,670,633 A | 9/1997 | Cook et al. |
| 5,677,437 A | 10/1997 | Teng et al. |
| 5,677,439 A | 10/1997 | Weis et al. |
| 5,679,509 A | 10/1997 | Wheeler et al. |
| 5,681,941 A | 10/1997 | Cook et al. |
| 5,683,985 A | 11/1997 | Chu et al. |
| 5,691,136 A | 11/1997 | Lupski et al. |
| 5,695,933 A | 12/1997 | Schalling et al. |
| 5,700,920 A | 12/1997 | Altmann et al. |
| 5,710,028 A | 1/1998 | Eyal et al. |
| 5,712,100 A | 1/1998 | Nakahama et al. |
| 5,714,320 A | 2/1998 | Kool |
| 5,714,331 A | 2/1998 | Buchardt et al. |
| 5,719,262 A | 2/1998 | Buchardt et al. |
| 5,728,526 A | 3/1998 | George, Jr. et al. |
| 5,733,733 A | 3/1998 | Auerbach |
| 5,736,365 A | 4/1998 | Walker et al. |
| 5,744,305 A | 4/1998 | Fodor et al. |
| 5,766,891 A | 6/1998 | Shuman |
| 5,770,408 A | 6/1998 | Sato |
| 5,795,714 A | 8/1998 | Cantor et al. |
| 5,800,992 A | 9/1998 | Fodor et al. |
| 5,800,994 A | 9/1998 | Martinelli et al. |
| 5,807,674 A | 9/1998 | Tyagi |
| 5,817,529 A | 10/1998 | Wu |
| 5,821,084 A | 10/1998 | Olmsted et al. |
| 5,824,517 A | 10/1998 | Cleuziat et al. |
| 5,830,711 A | 11/1998 | Barany et al. |
| 5,849,544 A | 12/1998 | Harris et al. |
| 5,854,033 A | 12/1998 | Lizardi |
| 5,856,096 A | 1/1999 | Windle et al. |
| 5,866,329 A | 2/1999 | Demetriou et al. |
| 5,866,336 A | 2/1999 | Nazarenko et al. |
| 5,871,697 A | 2/1999 | Rothberg et al. |
| 5,871,914 A | 2/1999 | Nathan |
| 5,871,921 A | 2/1999 | Landegren et al. |
| 5,871,928 A | 2/1999 | Fodor et al. |
| 5,874,260 A | 2/1999 | Cleuziat et al. |
| 5,876,924 A | 3/1999 | Zhang et al. |
| 5,876,932 A | 3/1999 | Fischer |
| 5,876,992 A | 3/1999 | De Rosier et al. |
| 5,880,473 A | 3/1999 | Ginestet |
| 5,882,912 A | 3/1999 | Sandstrom et al. |
| 5,882,935 A | 3/1999 | Hirai et al. |
| 5,886,329 A | 3/1999 | Kim |
| 5,888,731 A | 3/1999 | Yager et al. |
| 5,891,636 A | 4/1999 | Van Gelder et al. |
| 5,909,132 A | 6/1999 | Trofimenkoff et al. |
| 5,912,124 A | 6/1999 | Kumar |
| 5,912,148 A | 6/1999 | Eggerding |
| 5,914,229 A | 6/1999 | Loewy |
| 5,925,517 A | 7/1999 | Tyagi et al. |
| 5,942,391 A | 8/1999 | Zhang et al. |
| 5,942,609 A | 8/1999 | Hunkapiller et al. |
| 5,945,312 A | 8/1999 | Goodman et al. |

| | | | |
|---|---|---|---|
| 5,955,933 A | 9/1999 | Nishihara et al. | |
| 5,959,095 A | 9/1999 | Martinelli et al. | |
| 5,962,223 A | 10/1999 | Whiteley et al. | |
| 5,968,743 A | 10/1999 | Matsunaga et al. | |
| 5,976,806 A | 11/1999 | Mahajan et al. | |
| 5,985,639 A | 11/1999 | Christianson et al. | |
| 5,998,175 A | 12/1999 | Akhavan-Tafti | |
| 6,007,994 A | 12/1999 | Ward et al. | |
| 6,008,373 A | 12/1999 | Waggoner et al. | |
| 6,013,431 A | 1/2000 | Soderlund et al. | |
| 6,013,444 A | 1/2000 | Dau et al. | |
| 6,017,703 A | 1/2000 | Kinders et al. | |
| 6,020,138 A | 2/2000 | Akhavan-Tafti | |
| 6,025,139 A | 2/2000 | Yager et al. | |
| 6,027,889 A | 2/2000 | Barany et al. | |
| 6,027,923 A | 2/2000 | Wallace | |
| 6,033,881 A | 3/2000 | Himmler et al. | |
| 6,037,130 A | 3/2000 | Tyagi et al. | |
| 6,054,274 A | 4/2000 | Sampson et al. | |
| 6,057,105 A | 5/2000 | Hoon et al. | |
| 6,064,274 A | 5/2000 | Nayebi et al. | |
| 6,077,668 A | 6/2000 | Kool | |
| 6,077,674 A | 6/2000 | Schleifer et al. | |
| 6,087,133 A | 7/2000 | Dattagupta et al. | |
| 6,087,476 A | 7/2000 | Kenten et al. | |
| 6,096,880 A | 8/2000 | Kool | |
| 6,117,635 A | 9/2000 | Nazarenko et al. | |
| 6,124,120 A | 9/2000 | Lizardi | |
| 6,132,728 A | 10/2000 | Beachy et al. | |
| 6,140,055 A | 10/2000 | Todd et al. | |
| 6,143,495 A | 11/2000 | Lizardi et al. | |
| 6,169,816 B1 | 1/2001 | Ravkin | |
| 6,183,960 B1 | 2/2001 | Lizardi | |
| 6,197,533 B1 | 3/2001 | Dawkes et al. | |
| 6,203,984 B1 | 3/2001 | Hu et al. | |
| 6,210,884 B1 | 4/2001 | Lizardi | |
| 6,214,587 B1 | 4/2001 | Dattagupta et al. | |
| 6,221,603 B1 | 4/2001 | Mahtani | |
| 6,225,636 B1 | 5/2001 | Ginestet | |
| 6,235,502 B1 | 5/2001 | Weissman et al. | |
| 6,242,188 B1 | 6/2001 | Dattagupta et al. | |
| 6,248,535 B1 | 6/2001 | Danenberg et al. | |
| 6,255,082 B1 | 7/2001 | Lizardi | |
| 6,255,636 B1 | 7/2001 | Cochran, II et al. | |
| 6,259,807 B1 | 7/2001 | Ravkin | |
| 6,274,320 B1 | 8/2001 | Rothberg et al. | |
| 6,277,607 B1 | 8/2001 | Tyagi et al. | |
| 6,280,949 B1 | 8/2001 | Lizardi | |
| 6,287,765 B1 | 9/2001 | Cubicciotti | |
| 6,287,768 B1 | 9/2001 | Chenchik et al. | |
| 6,287,776 B1 | 9/2001 | Hefti | |
| 6,287,824 B1 | 9/2001 | Lizardi | |
| 6,288,220 B1 | 9/2001 | Kambara et al. | |
| 6,291,183 B1 | 9/2001 | Pirrung et al. | |
| 6,291,187 B1 | 9/2001 | Kingsmore et al. | |
| 6,291,193 B1 | 9/2001 | Khodadoust | |
| 6,291,669 B1 | 9/2001 | Kwiatkowski et al. | |
| 6,294,664 B1 | 9/2001 | Ravikumar et al. | |
| 6,297,006 B1 | 10/2001 | Drmanac et al. | |
| 6,300,073 B1 | 10/2001 | Zhao et al. | |
| 6,312,902 B1 | 11/2001 | Shultz et al. | |
| 6,316,229 B1 | 11/2001 | Lizardi et al. | |
| 6,323,009 B1 | 11/2001 | Lasken et al. | |
| 6,329,150 B1 | 12/2001 | Lizardi et al. | |
| 6,344,329 B1 | 2/2002 | Lizardi | |
| 6,355,431 B1 | 3/2002 | Chee et al. | |
| 6,361,940 B1 | 3/2002 | Van Ness et al. | |
| 6,365,729 B1 | 4/2002 | Tyagi et al. | |
| 6,368,801 B1 | 4/2002 | Faruqi | |
| 6,403,319 B1 | 6/2002 | Lizardi et al. | |
| 6,417,340 B1 | 7/2002 | Mirkin et al. | |
| 6,440,707 B1 | 8/2002 | Kwok et al. | |
| 6,458,544 B1 | 10/2002 | Miller | |
| 6,458,556 B1 | 10/2002 | Hayashizaki | |
| 6,472,185 B2 | 10/2002 | McCasky Feazel et al. | |
| 6,475,736 B1 | 11/2002 | Stanton, Jr. | |
| 6,479,235 B1 | 11/2002 | Schumm et al. | |
| 6,479,242 B1 | 11/2002 | Guo et al. | |
| 6,479,244 B1 | 11/2002 | Belouchi et al. | |
| 6,498,023 B1 | 12/2002 | Abarzua | |
| 6,506,563 B1 | 1/2003 | Ward et al. | |
| 6,531,283 B1 | 3/2003 | Kingsmore et al. | |
| 6,573,051 B2 | 6/2003 | Alsmadi et al. | |
| 6,617,137 B2 | 9/2003 | Dean et al. | |
| 6,632,609 B2 | 10/2003 | Lizardi | |
| 6,635,425 B2 | 10/2003 | Bandaru et al. | |
| 6,642,034 B2 | 11/2003 | Lizardi | |
| 6,670,126 B2 | 12/2003 | Kingsmore et al. | |
| 6,686,157 B2 | 2/2004 | Ward et al. | |
| 6,703,228 B1 | 3/2004 | Landers et al. | |
| 6,703,885 B1 | 3/2004 | Fan et al. | |
| 6,706,519 B1 | 3/2004 | Kellogg et al. | |
| 6,713,257 B2 | 3/2004 | Shoemaker et al. | |
| 6,777,183 B2 | 8/2004 | Abarzua | |
| 6,797,474 B2 | 9/2004 | Lizardi | |
| 6,811,986 B2 | 11/2004 | Bandaru et al. | |
| 6,830,884 B1 | 12/2004 | Hafner et al. | |
| 6,861,222 B2 | 3/2005 | Ward et al. | |
| 6,861,231 B2 | 3/2005 | Shao | |
| 6,884,586 B2 | 4/2005 | Van Ness et al. | |
| 6,921,642 B2 | 7/2005 | Kingsmore et al. | |
| 6,942,972 B2 | 9/2005 | Farooqui et al. | |
| 6,977,148 B2 | 12/2005 | Dean et al. | |
| 6,977,153 B2 | 12/2005 | Kumar et al. | |
| RE39,007 E | 3/2006 | Dattagupta et al. | |
| 7,041,480 B2 | 5/2006 | Abarzua | |
| 7,074,600 B2 | 7/2006 | Dean et al. | |
| 7,297,485 B2 | 11/2007 | Bornarth et al. | |
| 7,358,047 B2 | 4/2008 | Hafner et al. | |
| 7,553,619 B2 | 6/2009 | Kumar et al. | |
| 7,618,776 B2 | 11/2009 | Lizardi | |
| 2001/0041340 A1 | 11/2001 | Kingsmore et al. | |
| 2002/0009716 A1 | 1/2002 | Abarzua | |
| 2002/0026046 A1* | 2/2002 | Pasloske et al. | 536/25.4 |
| 2002/0042052 A1 | 4/2002 | Nilsen et al. | |
| 2002/0119465 A1 | 8/2002 | Zhao et al. | |
| 2002/0120409 A1 | 8/2002 | Cao et al. | |
| 2002/0172972 A1 | 11/2002 | Tabor et al. | |
| 2002/0192649 A1 | 12/2002 | Lizardi | |
| 2002/0192658 A1 | 12/2002 | Ward et al. | |
| 2002/0197694 A1 | 12/2002 | Shao | |
| 2003/0008313 A1 | 1/2003 | Wiltshire | |
| 2003/0022167 A1 | 1/2003 | Alsmadi et al. | |
| 2003/0032014 A1 | 2/2003 | Wei et al. | |
| 2003/0032024 A1 | 2/2003 | Lizardi | |
| 2003/0059786 A1 | 3/2003 | Ward et al. | |
| 2003/0092901 A1 | 5/2003 | Farooqui et al. | |
| 2003/0099954 A1* | 5/2003 | Miltenyi et al. | 435/6 |
| 2003/0108902 A1 | 6/2003 | Abarzua | |
| 2003/0121338 A1 | 7/2003 | Yates | |
| 2003/0129658 A1* | 7/2003 | Yamaji et al. | 435/7.1 |
| 2003/0143613 A1 | 7/2003 | Kingsmore et al. | |
| 2003/0152932 A1 | 8/2003 | Kumar et al. | |
| 2003/0165948 A1 | 9/2003 | Alsmadi et al. | |
| 2003/0175788 A1 | 9/2003 | Alsmadi et al. | |
| 2003/0186288 A1* | 10/2003 | Spivack et al. | 435/6 |
| 2003/0207267 A1 | 11/2003 | Lasken et al. | |
| 2003/0207323 A1 | 11/2003 | Bandaru et al. | |
| 2003/0219751 A1 | 11/2003 | Lao et al. | |
| 2003/0235849 A1 | 12/2003 | Lizardi et al. | |
| 2004/0018489 A1* | 1/2004 | Ma et al. | 435/6 |
| 2004/0063144 A1 | 4/2004 | Lizardi | |
| 2004/0091857 A1 | 5/2004 | Nallur et al. | |
| 2004/0121338 A1 | 6/2004 | Alsmadi et al. | |
| 2004/0126770 A1 | 7/2004 | Kumar et al. | |
| 2004/0191784 A1 | 9/2004 | Abarzua et al. | |
| 2004/0248103 A1 | 12/2004 | Feaver et al. | |
| 2004/0248105 A1 | 12/2004 | Kumar | |
| 2004/0265897 A1 | 12/2004 | Lizardi | |
| 2005/0003369 A1* | 1/2005 | Christians et al. | 435/6 |
| 2005/0003410 A1* | 1/2005 | Frazer et al. | 435/6 |
| 2005/0069938 A1 | 3/2005 | Wang | |
| 2005/0069939 A1 | 3/2005 | Wang | |
| 2005/0074804 A1 | 4/2005 | Wang | |
| 2005/0079523 A1 | 4/2005 | Hafner et al. | |
| 2005/0112639 A1 | 5/2005 | Wang | |
| 2006/0083683 A1 | 4/2006 | Hsei et al. | |
| 2006/0126764 A1 | 6/2006 | Eklund et al. | |

| | | | |
|---|---|---|---|
| 2006/0166227 | A1 | 7/2006 | Kingsmore et al. |
| 2006/0188892 | A1 | 8/2006 | Latham et al. |
| 2008/0096258 | A1 | 4/2008 | Korfhage et al. |
| 2011/0112173 | A1* | 5/2011 | Brown et al. ............... 514/44 R |

FOREIGN PATENT DOCUMENTS

| | | |
|---|---|---|
| EP | 0 070 685 | 7/1982 |
| EP | 0 128 332 | 12/1984 |
| EP | 0 310 030 | 4/1989 |
| EP | 0 320 308 | 6/1989 |
| EP | 0 356 021 | 2/1990 |
| EP | 0 379 369 | 7/1990 |
| EP | 0 395 398 | 10/1990 |
| EP | 0 439 182 | 7/1991 |
| EP | 0 466 520 | 1/1992 |
| EP | 0 505 012 | 9/1992 |
| EP | 0 531 080 | 3/1993 |
| EP | 0 278 340 | 8/1993 |
| EP | 0278340 | 8/1993 |
| EP | 0 640 691 | 3/1995 |
| EP | 0 667 393 | 8/1995 |
| EP | 0 678 582 | 10/1995 |
| EP | 0 745 690 | 12/1996 |
| EP | 0 756 009 | 1/1997 |
| EP | 1 056 884 | 12/2001 |
| EP | 1056884 | 12/2001 |
| EP | 1 132 470 | 9/2005 |
| EP | 1132470 | 9/2005 |
| GB | 2332516 | 6/1999 |
| JP | 4262799 | 9/1992 |
| JP | 4304900 | 10/1992 |
| JP | 5130869 | 5/1993 |
| JP | 5146299 | 6/1993 |
| JP | 2005304396 | 11/2005 |
| WO | WO 94/16106 | 7/1984 |
| WO | WO 94/16108 | 7/1984 |
| WO | WO 89/09824 | 10/1989 |
| WO | WO 90/11372 | 10/1990 |
| WO | WO 91/06643 | 5/1991 |
| WO | WO 91/08307 | 6/1991 |
| WO | WO 91/16446 | 10/1991 |
| WO | WO 92/01813 | 2/1992 |
| WO | WO 94/24312 | 10/1994 |
| WO | WO 95/03430 | 2/1995 |
| WO | WO 95/03432 | 2/1995 |
| WO | WO 95/25180 | 9/1995 |
| WO | WO 95/22623 | 11/1995 |
| WO | WO 95/35390 | 12/1995 |
| WO | WO 96/00795 | 1/1996 |
| WO | WO 96/14406 | 5/1996 |
| WO | WO 96/33207 | 10/1996 |
| WO | WO 98/02449 | 1/1997 |
| WO | WO 97/07235 | 2/1997 |
| WO | WO 98/14610 | 4/1997 |
| WO | WO 97/17076 | 5/1997 |
| WO | WO 97/17471 | 5/1997 |
| WO | WO 97/19193 | 5/1997 |
| WO | WO 97/20948 | 6/1997 |
| WO | WO 97/42346 | 11/1997 |
| WO | WO 98/04746 | 2/1998 |
| WO | WO 98/16248 | 4/1998 |
| WO | WO 98/39485 | 9/1998 |
| WO | WO 99/18241 | 4/1999 |
| WO | WO 99/31276 | 6/1999 |
| WO | WO 99/54452 | 10/1999 |
| WO | WO 00/04193 | 1/2000 |
| WO | WO 00/15779 | 3/2000 |
| WO | WO 00/15849 | 3/2000 |
| WO | WO 00/36141 | 6/2000 |
| WO | WO 00/70095 | 11/2000 |
| WO | WO 00/71562 | 11/2000 |
| WO | WO 01/20039 | 3/2001 |
| WO | WO 01/27326 | 4/2001 |
| WO | WO 01/38580 | 5/2001 |
| WO | WO 01/40516 | 6/2001 |
| WO | WO 01/61037 | 8/2001 |
| WO | WO 01/64952 | 9/2001 |
| WO | WO 01/77390 | 10/2001 |
| WO | WO 01/79420 | 10/2001 |
| WO | WO 01/88190 | 11/2001 |
| WO | WO 01/97616 | 12/2001 |
| WO | WO 02/00934 | 1/2002 |
| WO | WO 02/02792 | 1/2002 |
| WO | WO 02/053780 | 7/2002 |
| WO | WO 02/077256 | 10/2002 |
| WO | WO 02/103058 | 12/2002 |
| WO | WO 03/008538 | 1/2003 |
| WO | WO 03/033724 | 4/2003 |
| WO | WO 03/066908 | 8/2003 |
| WO | WO 03/072809 | 9/2003 |
| WO | WO 2004/009814 | 1/2004 |
| WO | WO 2004/058987 | 7/2004 |
| WO | WO 2004/061119 | 7/2004 |

OTHER PUBLICATIONS

Krichevsky et al., A microRNA array reveals extensive regulation of microRNAs during brain development. RNA 9 : 1274 (2003).*
Santoro et al., A general purpose RNA-cleaving DNA enzyme. PNAS 94 : 4262 (1997).*
Schnierle et al., Cap-specific mRNA (nucleoside-O2'-)-methyltransferase and poly(A) polymerase stimulatory activities of vaccinia virus are mediated by a single protein. PNAS 89 (7) : 2897 (1992).*
Gene Characterization Kits ; The Stratagene Catalog p. 39 (1988).*
Hayward-Lester et al., Accurate and Absolute Quantitative Measurement of gene expression by single-tube RT-PCR and HPLC. Genome Research 5:494 (1995).*
Wang et al., Quantitation of mRNA by the polymerase chain reaction. PNAS 86 : 9717 (1989).*
AAAI Board of Directors. (1995) Measurement of specific and non-specific IgG4 levels as diagnostic and prognostic tests for clinical allergy. J Allergy Clin Immunol. 95: 652-654.
Abravaya et al. (1995) Detection of point mutations with a modified ligase chain reaction (Gap-LCR). Nucleic Acids Res. 23(4): 675-682.
Agüero et al. (2000). A random sequencing approach for the analysis of the Trypanosoma cruzi genome: general structure, large gene and repetitive DNA families, and gene discovery. Genome Res. 10(12): 1996-2005.
Aliotta et al. (1996) Thermostable Bst DNA polymerase I lacks a 3'→5' proofreading exonuclease activity. Genet Anal. 12: 185-195.
Alsmadi et al. (2009) Specific and complete human genome amplification with improved yield achieved by phi29 DNA polymerase and a novel primer at elevated temperature. BMC Res Notes. 2: 48.
Altschul et al. (1997) Gapped BLAST and PSI-BLAST: a new generation of protein database search programs. Nucleic Acids Res. 25(17): 3389-402.
Alves et al. (1988) Dot blot detection of point mutations with adjacently hybridising synthetic oligonucleotide probes. Nucleic Acids Res. 16(17): 8723.
Anderson et al. (1997) A comparison of selected mRNA and protein abundances in human liver. Electrophoresis. 18: 533-537.
Andras et al. (2001) Strategies for signal amplification in nucleic acid detection. Mol Biotechnol. 19(1): 29-44.
Ansari-Lari et al. (1996) Improved ligation-anchored PCR strategy for identification of 5' ends of transcripts. Biotechniques. 21(1): 34-6, 38.
Applied Biosystems. "Avoiding DNA contamination in RT-PCR" internet webpage retrieved from http://www.ambion.com/techlib/tb/tb_176.html on Jan. 14, 2011.
Applied Biosystems. "Methods to remove DNA contamination from RNA samples" internet webpage retrieved from http://www.ambion.com/techlib/tb/tb_181.html on Jan. 14, 2011.
Apweiler et al. (2001) The InterPro database, an integrated documentation resource for protein families, domains and functional sites. Nucleic Acids Res. 29(1): 37-40.
Armitage et al. (1998) Hairpin-forming peptide nucleic acid oligomers. Biochemistry. 37(26): 9417-25.
Arn et al. (1996) the 2'-5' RNA ligase of *Escherichia coli*. Purification, cloning, and genomic disruption. J. Biol. Chem. 271(49): 31145-53.
Arnold et al. (1989) Assay formats involving acridinium-ester-labeled DNA probes. Clin Chem. 35(8): 1588-1594.

Asseline et al. (1992) Solid-phase preparation of 5′,3′-heterobifunctional oligodeoxyribonucleotides using modified solid supports. Tetrahedron. 48(7): 1233-1254.

Atencia et al. (1999) T4 RNA ligase catalyzes the synthesis of dinucleoside polyphosphates. Eur J Biochem. 261(3): 802-11.

Auer et al. (1996) Selective amplification of RNA utilizing the nucleotide analog dITP and Thermus thermophilus DNA polymerase. Nucleic Acids Res. 24(24): 5021-5.

Ausubel et al. (Eds). (1987). Current Protocols in Molecular Biology. vol. 1, Unit 1.6—Minipreps of Plasmid DNA, Unit 1.7—CsCl/Ethidium Bromide Preparations of Pplasmid DNA, Unit 2.2—Preparation of Genomic DNA from Mammalian Tissue.

Baldauf et al. (2000) A kingdom-level phylogeny of eukaryotes based on combined protein data. Science. 290(5493): 972-7.

Baner et al. (1998) Signal amplification of padlock probes by rolling circle replication. Nucl. Acid Res. 26(22): 5073-5078.

Barany. (1991) Genetic disease detection and DNA amplification using cloned thermostable ligase. Proc. Natl. Acad. Sci. USA 88: 189-193.

Barbato et al. (1987) Solid Phase Synthesis of Cyclic Oligodeoxyribonucleotides. Tetrahedron Letters. 28(46): 5727-5728.

Bauer et al. (1997) Use of manganese in RT-PCR eliminates PCR artifacts resulting from DNase I digestion, Biotechniques. 22(6):1128-32.

Beaucage et al. (1981) Deoxynucleoside phosphoramidites—a new class of key intermediates for deoxypolynucleotide synthesis. Tetrahedron Lett. 22(20): 1859-1862.

Becker et al. (1999) LMPCR for detection of oligonucleotide-directed triple helix formation: a cautionary note. Antisense Nucleic Acid Drug Dev. 9(3): 313-6.

Becker et al. (2000) PCR bias in ecological analysis: a case study for quantitative Taq nuclease assays in analyses of microbial communities. Appl Environ Microbiol. 66(11): 4945-53.

Beier et al. (1999) Versatile derivatisation of solid support media for covalent bonding on DNA-microchips. Nucleic Acids Res. 27(9): 1970-7.

Beigelman et al. (1994) Synthesis of 1-deoxy-d-ribofuranose phosphoramidite & the incorporation of abasic nucleotides in stem-loop II of a hammerhead ribozyme. Bioorganic & Medicinal Chemistry Letters. 4(14): 1715-1720.b.

Bertina et al. (1994) Mutation in blood coagulation factor V associated with resistance to activated protein C. Nature. 369: 64-67.

Betz et al. (1981) Variants of a cloned synthetic lactose operator. I. A palindromic dimer lactose operator derived from one stand of the cloned 40-base pair operator. Gene. 13(1): 1-12.

Bi et al. (1997) CCR: a rapid and simple approach for mutation detection. Nucleic Acids Res. 25(14): 2949-51.

Birkenmeyer et al. (1991) DNA probe amplification methods. J.Virol. Meth. 35: 117-126.

Birnboim HC. (1983) A rapid alkaline extraction method for the isolation of plasmid DNA. Methods Enzymol. 100: 243-255.

Blain et al. (1995) Effects on DNA synthesis and translocation caused by mutations in the RNase H domain of Moloney murine leukemia virus reverse transcriptase.J Virol. 69(7): 4440-52.

Blanc et al. (1999) the mitochondrial RNA ligase from Leishmania tarentolae can join RNA molecules bridged by a complementary RNA. J. Biol. Chem. 274(34): 24289-96.

Blanco et al. (1984) Characterization and purification of a phage Æ29-encoded DNA polymerase required for the initiation of replication. Proc. Natl. Acad. Sci. USA 81: 5325-5329.

Blanco et al. (1989) Highly Efficient DNA Synthesis by the Phage Æ29DNA Polymerase. J. Biol. Chem. 264(15): 8935-8940.

Blanco et al. (1994) Terminal protein-primed DNA amplification. Proc Natl Acad Sci USA. 91:12198-12202.

Bloch et al. (1988) Alpha-anomeric DNA: beta-RNA hybrids as new synthetic inhibitors of *Escherichia coli* RNase H, Drosophila embryo RNase H and M-MLV reverse transcriptase. Gene. 72(1-2): 349-60.

Boehmer et al. (1993) Herpes Simplex Virus Type 1 ICP8: Helix-Destabilizing Properties. J. Virol. 67(2): 711-715.

Bonaldo et al. (1996) Normalization and subtraction: two approaches to facilitate gene discovery. Genome Res. 6(9): 791-806.

Bonnet et al. (1999) Thermodynamic basis of the enhanced specificity of structured DNA probes. Proc. Natl. Acad. Sci. USA. 96(11): 6171-6176.

Boore et al. (2005) Sequencing and comparing whole mitochondrial genomes of animals. Methods Enzymol. 395: 311-48.

Brandenburg et al. (1995) Branched oligodeoxynucleotides: a new synthetic strategy and formation of strong intra- and intermolecular triple helical complexes Bioorganic & Medicinal Chemistry Letters. 5(8): 791-794.

Braun et al. (1999) Cholera toxin suppresses interleukin (IL)-12 production and IL-12 receptor beta1 and beta2 chain expression. J Exp Med. 189(3): 541-52.

Brennan et al. (1983) Using T4 RNA ligase with DNA substrates. Methods Enzymol. 100: 38-52.

Broude et al. (1994) Enhanced DNA sequencing by hybridization. Proc Natl Acad Sci U S A. 91(8): 3072-6.

Brownstein et al. (1996) Modulation of non-templated nucleotide addition by Taq DNA polymerase: primer modifications that facilitate genotyping. Biotechniques. 20(6): 1004-6, 1008-10.

Brush. (1998) Dye hard: protein gel staining products. The Scientist. 12: 16-22.

Bryant et al. (1982) Phosphorothioate substrates for T4 RNA ligase. Biochemistry. 21(23): 5877-85.

Buchanan et al. (2000) Long DOP-PCR of rare archival anthropological samples. Hum Biol. 72(6): 911-25.

Burgess et al. (1996) A new photolabile protecting group for nucleotides. Abstracts of Papers, Part 2; 211th ACS National Meeting, American Chemical Society. New Orleans, LA.

Butler et al. (1982) Bacteriophage SP6-specific RNA polymerase. J. Biol. Chem. 257(10): 5772-5778.

Cameron et al. (2000) A sea urchin genome project: sequence scan, virtual map, and additional resources. Proc Natl Acad Sci U S A. 97(17): 9514-8.

Capobianco et al. (1990) One pot solution synthesis of cyclic oligodeoxyribonucleotides. Nucleic Acids Res. 18(9): 2661-9.

Carninci et al. (1998) Thermostabilization and thermoactivation of thermolabile enzymes by trehalose and its application for the synthesis of full length cDNA. Proc Natl Acad Sci U S A. 95(2): 520-4.

CDP-Star CSPD & AMPPD Substrates for A1 Phosphatase. Printout on Mar. 24, 2000 from webpage (www.tropix.com/alkasubs.htm).

Chandler DP. (1998) Redifining relativity: quantitative PCR at low template concentrations for industrial and environmental microbiology. J. Indust. Microbiol. Biotech. 21: 128-140.

Chang. (2000) The pharmacological basis of anti-IgE therapy. Nat Biotech. 18: 157-162.

Chatterjee et al. (1991) Cloning and overexpression of the gene encoding bacteriophage T5 DNA polymerase. Gene. 97: 13-19.

Chen et al. (1998) Amplification of closed circular DNA in vitro. Nucleic Acids Res. 26(23): 1126-7.

Chetverina et al. (1993) Cloning of RNA molecules in vitro. Nucl. Acids Res. 21(10): 2349-2353.

Cheung et al. (1996) Whole genome amplification using a degenerate oligonucleotide primer allows hundreds of genotypes to be performed on less than one nanogram of genomic DNA. Proc Natl Acad Sci USA. 93(25): 14676-79.

Choo et al. (1994) Differentiation-independent constitutive expression of the human papillomavirus type 16 E6 and E7 oncogenes in the CaSki cervical tumour cell line. J Gen Virol. 75 (Pt 5): 1139-47.

Christian et al. (2001) Detection of DNA point mutations and mRNA expression levels by rolling circle amplification in individual cells. Proc Natl Acad Sci U S A. 98(25): 14238-142+A8543.

Colantuoni et al. (2001) Gene Expression Profiling in Postmortem Rett Syndrome Brain: Differential Gene Expression and Patient Classification. Neutoboil. Dis. 8: 847-865.

Colantuoni et al. High Throughput Analysis of Gene Expression in the Human Brain. J. Neurosci. Res. 59: 1-10.

Connolly BA. (1985) Chemical synthesis of oligonucleotides containing a free sulphydryl group and subsequent attachment of thiol specific probes. Nucleic Acids Res. 13(12): 4485-502.

Connolly BA. (1987) The synthesis of oligonucleotides containing a primary amino group at the 5′-terminus. Nucleic Acids Res. 15(7): 3131-9.

Craxton et al. (1991) Linear Amplification Sequencing, a Powerful Method for Sequencing DNA. Meth. Compan. Meth. Enzymol. 3(1): 20-26.

Cremer et al. (1988) Detection of chromosome aberrations in metaphase and interphase tumor cells by in situ hybridization using chromosome-specific library probes. Hum Genet. 80(3): 235-46.

Crollius et al. (2000) Characterization and repeat analysis of the compact genome of the freshwater pufferfish Tetraodon nigroviridis. Genome Res. 10(7): 939-49.

Crooke et al. (1996) Pharmacokinetic properties of several novel oligonucleotide analogs in mice. J Pharmacol Exp Ther. 277(2): 923-937.

Cummins et al. (1996) Biochemical and physicochemical properties of phosphorodithioate DNA. Biochemistry. 35(26): 8734-41.

Damha et al. (1998) Synthesis of a branched DNA/RNA chimera similar to the msDNA molecule of Myxococcus Xanthus. 39(23): 3907-3910.

Das et al. Full-length cDNAs: more than just reaching the ends. Physiological Genomics 6: 57 (2001).

Daubendiek et al. (1995) Rolling-circle RNA synthesis: circular oligonucleotides as efficient substrates for T7 RNA polymerase. J Am Chem Soc. 117: 7818-7819.

Daubendiek et al. (1997) Generation of catalytic RNAs by rolling transcription of synthetic DNA nanocircles. Nature Biotechnology. 15(3): 273-277.

Davanloo et al. (1984) Cloning and expression of the gene for bacteriophage T7 RNA polymerase. Proc Natl Acad Sci USA. 81: 2035-2039.

Davies et al. (1999) Profiling of amyloid beta peptide variants using SELDI Protein Chip arrays. Biotechniques. 27(6): 1258-61.

Davis et al. (1980) A Manual for Genetic Engineering. Advanced Bacterial Genetics. Cold Spring Harbor Laboratory. Cold Spring Harbor, NY.

de Baar, et al. (2001) Single rapid real-time monitored isothermal RNA amplification assay for quantification of human immunodeficiency virus type 1 isolates from groups M, N, and O. J Clin Microbiol. 39(4): 1378-84.

de Vega et al. (1997) An invariant lysine residue is involved in catalysis at the 3'-5' exonuclease active site of eukaryotic-type DNA polymerases. J Mol Biol. 270(1): 65-78.

de Vroom et al. (1988) Synthesis of cyclic oligonucleotides by a modified phosphotriester approach. Nucleic Acids Res. 16(10): 4607-20.

Dean et al. (2001) Rapid Amplification of Plasmid and Phage DNA Using Phi29 DNA Polymerase and Multiply-Primed Rolling Circle Amplification. Genome Res. 11: 1095-1099.

Dean et al. (2002) Comprehensive human genome amplification using multiple displacement amplification. Proc Natl Acad Sci USA. 99(8): 5261-66.

Detter et al. (2002) Isothermal strand-displacement amplification applications for high-throughput genomics. Genomics. 80(6): 691-98.

Diegelman et al. (1998) Generation of circular RNAs and trans-cleaving catalytic RNAs by rolling transcription of circular DNA oligonucleotides encoding hairpin ribozymes. Nucleic Acids Res. 26(13): 3235-41.

Doherty et al. (2000) Structural and mechanistic conservation in DNA ligases. Nucleic Acids Res. 28(21): 4051-8.

Dolinnaya et al. (1993) Oligonucleotide circularization by template-directed chemical ligation. Nucleic Acids Res. 21(23): 5403-7.

Dostie et al. Numerous microRNPs in neuronal cells containing novel microRNAs. RNA 9: 180 (2003).

Dreyer et al. (1985) Sequence-specific cleavage of single-stranded DNA: oligodeoxynucleotide-EDTA X Fe(II). Proc Natl Acad Sci U S A. 182(4): 968-72.

Durand et al. (1990) Circular dichroism studies of an oligodeoxyribonucleotide containing a hairpin loop made of a hexaethylene glycol chain: conformation and stability. Nucleic Acids Res. 18(21): 6353-9.

Dynal. (1995) DYNAL Technical Handbook. Biomagnetic techniques in molecular biology.

Eads et al. (1999) CpG island hypermethylation in human colorectal tumors is not associated with DNA methyltransferase overexpression. Cancer Res. 59(10): 2302-2306.

Eberwine et al. (1992) Analysis of gene expression in single live neurons. Proc Natl Acad Sci USA. 89(7): 3010-3014.

Eckert et al. (1991) DNA polymerase fidelity and the polymerase chain reaction. PCR Methods Appl. 1(1): 17-24.

Eckstein et al. (1989) Phosphorothioates in molecular biology. Trends Biochem Sci. 14(3): 97-100.

Egholm et al. (1992) Peptide nucleic acids (PNA). Oligonucleotide analogs with an achiral peptide backbone. J. Am. Chem. Soc., 114 (5), pp. 1895-1897.

Ekins et al. (1991) Multianalyte microspot immunoassay—microanalytical "compact disk" of the future. Review. Clin Chem. 37(11): 1955-67.

Ekins. (1998) Ligand assays: from electrophoresis to miniaturized microarrays. Clin Chem. 44(9): 2015-2030.

Englisch et al. (199) Chemically modified oligonucleotides as probes and inhibitors. Angewandte Chemie, Intl Ed. 30(6): 613-722.

Erie et al. (1989) Melting behavior of a covalently closed, single-stranded, circular DNA.Biochemistry. 28(1): 268-73.

Ernst et al. (1989) Cyanine dye labeling reagents for sulfhydryl groups. Cytometry. 10: 3-10.

Esteban et al. (1993) Fidelity of 29 DNA Polymerase. Journal of Biological Chemistry. 268(4): 2719-2726.

Faruqi et al. (2001) High-throughput genotyping of single nucleotide polymorphisms with rolling circle amplification. BMC Genomics. 2(1): 4.

Fermentas Life Sciences. (2010) Thermophilic DNA Polymerases Product Page (p. 13). Retrieved from Fermentas Website Product page on Sep. 13, 2010 at http://www.fermentas.com/en/products/all/modifying-enzymes/thermophilic-polymerases.

Fields et al. (1994) How many genes in the human genome? Nat Genet. 7:345-346.

Fire et al. (1995) Rolling replication of short DNA circles. Proc Natl Acad Sci USA. 92: 4641-4645.

Fleischmann et al. (1995) Whole-Genome Random Sequencing and Assembly of Haemophilus influenza Rd. Science 269:496-512.

Fu et al. (1994) Hammerhead Ribozymes Contianing Non-Nucleoside Linkers are Active RNA Catalysts. J. Am. Chem. Soc. 116: 4591-4598.

Gait MJ. (1993) Oligoribonucleotides. Antisense Research and Applications. (Crooke et al, eds., CRC Press) Chapter 16, pp. 289-301.

Galli et al. (1995) Transcriptional analysis of rolling circle replicating plasmid pVT736-1: evidence for replication control by antisense RNA. J Bacteriol. 177(15): 4474-4480.

Gasparini et al. (1999) Analysis of 31 CFTR mutations by polymerase chain reaction/oligonucleotide ligation assay in a pilot screening of 4476 newborns for cystic fibrosis. J Med Screen. 6(2): 67-9.

Gasparro et al. (1994) Site-specific targeting of psoralen photoadducts with a triple helix-forming oligonucleotide: characterization of psoralen monoadduct and crosslink formation. Nucleic Acids Research. 22(14): 2845-2852.

Ge H. (2000) UPA, a universal protein array system for quantitative detection of protein-protein, protein-DNA, protein-RNA and protein-ligand interactions. Nucleic Acids Res. 28(2): e3.

GE Healthcare. (2010) GE Healthcare Life Sciences: "TempliPhi FAQ" Retrieved from the Internet: http://www.gelifesciences.com/aptrix2 uppO1077.nsf/Contentsample_preparation-product_selection_category-roll ing_circle_amplification-sample_templiphi faq [retrieved on Jul. 29, 2010].

Gerdes et al. (1994) Dynamic Changes in the Higher-Level Chromatin of Specific Sequences Revealed by In Situ Hybridization to Nuclear Halos. J. Cell Biol. 126(2): 289-304.

Gillespie et al. (2000) HLA class II typing of whole genome amplified mouth swab DNA. Tissue Antigens. 56(6): 530-8.

Gryaznov et al. (1993) Template controlled coupling and recombination of oligonucleotide blocks containing thiophosphoryl groups. Nucleic Acids Res. 21(6): 1403-8.

Grzybowski et al. (1993) Synthesis and antibody-mediated detection of oligonucleotides containing multiple 2,4-dinitrophenyl reporter groups. Nucleic Acids Res. 21(8): 1705-12.

Guatelli et al. (1990) Isothermal, in vitro amplification of nucleic acids by a multienzyme reaction molded after retroviral replication. Proc. Natl. Acad. Sci. USA 87: 1874-1878.

Guillier-Gencik et al. (1999) Generation of whole-chromosome painting probes specific to each chicken macrochromosome. Cytogenet Cell Genet. 87(3-4): 282-5.

Gumport et al. (1981) T4 RNA ligase as a nucleic acid synthesis and modification reagent. Gene Amplif Anal. 2: 313-45.

Gunji et al. (1992) Correlation between the serum level of hepatitis C virus RNA and disease activities in acute and chronic hepatitis C. Int J Cancer. 52(5): 726-730.

Guo et al. (1994) Direct fluorescence analysis of genetic polymorphisms by hybridization with oligonucleotide arrays on glass supports. Nucl. Acids Res. 22(24): 5456-5464.

Guo et al. (1997) Enhanced discrimination of single nucleotide polymorphisms by artificial mismatch hybridization. Nature Biotechnology. 15: 331-335.

Gupta et al. (1990) A universal solid support for the synthesis of 3'-thiol group containing oligonucleotides. Tetrahedron Letters. 31(17): 2471-2474.

Gupta et al. (1993) Expression of HIV-1 RNA in plasma correlates with the development of AIDS: a multicenter AIDS cohort study (MACS) Ninth International Conference on AIDS/Fourth STD World Congress. Berlin, Germany (abstract).

Gusev et al. (2001) Rolling circle amplification: a new approach to increase sensitivity for immunohistochemistry and flow cytometry. American Journal of Pathology. 159(1): 63-69.

Gygi et al. (1999) Correlation between protein and mRNA abundance in yeast. Mol Cell Biol. 19(3): 1720-1730.

Haaf et al. (1994) High resolution ordering of YAC contigs using extended chromatin and chromosomes. Hum Mol Genet. 3(4): 629-33.

Hacia et al. (1996) Detection of heterozygous mutations in BRCA1 using high density oligonucleotide arrays and two-colour fluorescence analysis. Nat. Genet. 14: 441-447.

Haff et al. (1997) Single-nucleotide polymorphism identification assays using a thermostable DNA polymerase and delayed extraction MALDI-TOF mass spectrometry. Genome Res. 7(4): 378-88.

Hagiwara et al. (1993) Quantitation of hepatitis C virus RNA in serum of asymptomatic blood donors and patients with type C chronic liver disease. Hepatology. 17(4): 545-550.

Hall et al. (1957) Nucleotide. Part XLI. Mixed anhydrides an intermediate in the synthesis of dinucleoside phosphates. J Chem Soc. 3291-3296.

Hall et al. (2000) Sensitive detection of DNA polymorphisms by the serial invasive signal amplification reaction. Proc. Natl. Acad. Sci. USA 97(15): 8272-8277.

Hanvey et al. (1992) Antisense and antigene properties of peptide nucleic acids. Science. 258: 1481-1485.

Harada et al. (1993) in vitro selection of optimal DNA substrates for T4 RNA ligase. Proc Natl Acad Sci U S A. 90(4): 1576-9.

Harada et al. (1994) In vitro selection of optimal DNA substrates for ligation by a water-soluble carbodiimide. J Mol Evol. 38(6): 558-60.

Haralambidis et al. (1987) Preparation of base-modified nucleosides suitable for non-radioactive label attachment and their incorporation into synthetic oligodeoxyribonucleotides. Nucleic Acids Res. 15(12): 4857-76.

Harper et al. (1999) Recent advances and future developments in PGD. Prenat Diagn. 19(13): 1193-9.

Hata et al. (1988) Structure of the human ornithine transcarbamylase gene. J Biochem. 103: 302-308.

Heinonen et al. (1997) Simple triple-label detection of seven cystic fibrosis mutations by time-resolved fluorometry. Clin Chem. 43(7): 1142-1150.

Hendrickson et al. (1995) High sensitivity multianalyte immunoassay using covalent DNA-labeled antibodies and polymerase chain reaction. Nucleic Acids Res. 23(3): 522-529.

Henegariu et al. (2000) Custom flourescent-nucleotide synthesis as an alternative method for nucleic acid labeling. Nat Biotech. 18: 345-346.

Hermanson et al. (1992) Immobilized Affinity Ligands. Academic Press, NY.

Higgins et al. (1979) Addition of oligonucleotides to the 5'-terminus of DNA by T4 RNA ligase. Nucleic Acids Res. 6(3): 1013-24.

Higgins et al. (1979) DNA joining enzymes: a review. Methods Enzymol. 68: 50-71.

Hinton et al. (1978) T4 RNA Ligase joins 2'-deoxyribonucleoside 3',5'-bisphosphates to oligodeoxyribonucleotides. Biochemistry. 17(24): 5091-7.

Hinton et al. (1979) The synthesis of oligodeoxyribonucleotides using RNA ligase. Nucleic Acids Res. 7(2): 453-64.

Hinton et al. (1982) The preparative synthesis of oligodeoxyribonucleotides using RNA ligase. Nucleic Acids Res. 10(6): 1877-94.

Hoeltke et al. (1992) Multiple nucleic acid labeling and rainbow detection. Anal Biochem. 207: 24-31.

Holland et al. (1991) Detection of specific polymerase chain reaction product by utilizing the 5'→3' exonuclease activity of Thermus aquaticus DNA polymerase. Proc. Natl. Acad. Sci. USA 88: 7276-7280.

Holloway et al. (1993) An exonuclease-amplification coupled capture technique improves detection of PCR product. Nucleic Acids Research. 21(16): 3905-3906.

Holmes et al. (Eds.) (1981) Large Scale Isolation of Plasmid DNA. Harvesting and Lysis of Bacteria. pp. 89-91.

Holton et al. (1991) A simple and efficient method for direct cloning of PCR products using ddT-tailed vectors. Nucleic Acids Res. 19(5): 1156.

Horn et al. (1997) Chemical synthesis and characterization of branched oligodeoxyribonucleotides (bDNA) for use as signal amplifiers in nucleic acid quantification assays. Nucleic Acids Res. 25(23): 4842-9.

Hoy et al. (1993) Bromodeoxyuridine/DNA analysis of replication in CHO cells after exposure to UV light. Mutat. Res. 290: 217-230.

Hsu et al. (2000) Hydration of [d(CGC)r(aaa)d(TTTGCG)]2. J. Mol. Biol. 295, 1129-1137.

Hsuih et al. (1995) Quantitative detection of HCV RNA using novel ligation-dependent polymerase chain reaction. American Association for the Study of Liver Diseases. (Chicago, IL) [poster abstract].

Hsuih et al. (1996) Novel, ligation-dependent PCR assay for detection of hepatitis C in serum. J Clin Microbiol. 34(3): 501-7.

Humphery-Smith et al. (1997) Proteome Analysis: Genomics via the Output Rather than the Input Code. J. Protein Chem. 16(5): 537-544.

Huryn et al. (1992) AIDS-driven nucleoside chemistry. Chem Rev. 92: 1745-1768.

Iakobashvili et al. (1999) Low temperature cycled PCR protocol for Klenow fragment of DNA polymerase I in the presence of proline. Nucleic' Acids Res. 27(6): 1566-8.

Innis et al. (1988) DNA sequencing with Thermus aquaticus DNA polymerase and direct sequencing of polymerase chain reaction-amplified DNA. Proc Natl Acad Sci USA. 85(24): 9436-9440.

Intergen Company. Amplifluor™ Apoptosis Gene System. Retrieved on Jan. 3, 2002 from product webpage at http://www.intergenco.com/body_apoptosis_amplifluor.html (4 pages).

Intergen Company. Principles of the Amplifluor™ Universal Amplification and Detection System Procedure. Retrieved on Jan. 3, 2002 from product webpage at http://www.intergenco.com/body_apoptosis_uniprimer.html (2 pages).

Ishikawa et al. (1995) Sequence-based typing of HLA-A2 alleles using a primer with an extra base mismatch. Hum Immunol. 42(4): 315-318.

Itaka et al. (2002) Evaluation by fluorescence resonance energy transfer of the stability of nonviral gene delivery vectors under physiological conditions. Biomacromolecules. 3(4): 841-5.

Itakura et al. (1984) Synthesis and Use of Synthetic Oligonucleotides. Annu. Rev. Biochem. 53: 323-356.

Iuodka et al. (1991) [Substrate specificity of T4 RNA-ligase. The role of phosphate nucleotide residues in the formation of a covalent AMP-RNA-ligase complex]. [Article in Russian]. Biokhimiia. 56(5): 798-805.

Iyer et al. (1990) 3-H-1,2-benzodithiole-3-one 1, 1-dioxide as an improved sulfurizing reagent in the solid-phase synthesis of oligodeoxyribonucleosdie phosphorothioates. J Am Chem Soc. 112: 1253-1254.

Jablonski et al. (1986) Preparation of oligodeoxynucleotide-alkaline phosphatase conjugates and their use as hybridization probes. Nucleic Acids Res. 14(15): 6115-28.

Jacobsen et al. (1974) The N-terminal amino acid sequences of DNA polymerase I from *Escherichia coli* and of the large and the small fragments obtained by a limited proteolysis. Eur J Biochem. 45: 623-627.

Jalanko et al. (1992) Screening for defined cystic fibrosis mutations by solid-phase minisequencing. Clin Chem. 38(1): 39-43.

James et al. (1997) Surprising fidelity of template-directed chemical ligation of oligonucleotides. Chem Biol. 4(8): 595-605.

Jiang et al. (1996) An efficient method for generation and subcloning of tandemly repeated DNA sequences with defined length, orientation and spacing. Nucl. Acids Res. 24(16): 3278-3279.

Johnstone et al. (1987) Immunochemistry In Practice, Blackwell Scientific Publications, Oxford, England, Chapters 2 and 3, pp. 30-85.

Johnstone et al. (1987) Immunochemistry in Practice, Blackwell Scientific Publications, Oxford, England, pp. 209-216 and 241-242.

Jonsson et al. (1995) Sequence of the DNA ligase-encoding gene from thermus scotoductus and conserved motifs in DNA ligases. Gene. 151: 177-180.

Jun-Dong et al. (1990) Application of Wittig Reaction to Adenosine Derivatives. Synthesis. Oct. 1990, 909-911.

Jung et al. (1987) Bacteriophage PRD1 DNA polymerase: Evolution of DNA polymerases. Proc. Natl. Acad. Sci. USA 84: 8287-8291.

Kabanov et al. (1990) A new class of antivirals: antisense oligonucleotides combined with a hydrophobic substituent effectively inhibit influenze virus reproduction and synthesis of virus-specific proteins in MDCK cells. FEBS Lett. 259(2): 327-330.

Kabat. (1968) Structural Concepts in Immunology and Immunohistochemistry. Holt, Rinehart and Winston, Inc. pp. 162-168.

Kaboord et al. (1995) Accessory proteins function as matchmakers in the assembly of the T4 DNA polymerase holoenzyme. Current Biology. 5(2): 149-157.

Kälin et al. (1992) Evaluation of the ligase chain reaction (LCR) for the detection of point mutations. Mutation Research. 283(2): 119-128.

Kalnik et al. (1988) NMR studies of abasic sites in DNA duplexes: deoxyadenosine stacks into the helix opposite the cyclic analogue of 2-deoxyribose. Biochemistry. 27(3): 924-31.

Kaluz et al. (1995) Enzymatically produced composite primers: an application of T4 RNA ligase-coupled primers to PCR. Biotechniques. 19(2): 182-4, 186.

Kanaya et al. (1986) Template-directed polymerization of oligoadenylates using cyanogen bromide. Biochemistry. 25(23):7423-30.

Kang et al. (2000) Transcript quantitation in total yeast cellular RNA using kinetic PCR. Nucleic Acids Res. 28(2): e2.

Kaplan et al. (1978) Rapid Photolytic of Adenosine 5'-Triphosphate from a Protected Analogue: Utilization by the Na:K Pump of Human Red Blood Cell Ghosts. Biochemistry 17: 1929-1935.

Kapuschoc et al. (2002) Differential localization of nuclear-encoded tRNAs between the cytosol and Mitochondrion in Leishmania tarentolae. RNA. 8(1): 57-66.

Kazakov et al. (1998) RNA Padlocks: Locking out ribosomes. Presentation at IBC 5th Annual International Conference on Antisense. Coronado, CA.

Kellogg et al. (1994) TaqStart Antibody: "Hot Start" PCR facilitated by a neutralizing monoclonal antibody directed against Taq DNA polymerase. BioTechniques. 16(6): 1134-1137.

Kerkhof. (1994) A comparison of substrates for quantifying the signal from a nonradiolabeled DNA probe. Analytical Biochemistry. 205: 359-364.

Kessler. (1991) the digoxigenin:anti-dioxgenin (DIG) technology—a survey on the concept and realization of a novel bioanalytical indicator system. Mol Cell Probes. 5: 161-205.

Khrapko et al. (1991) Hybridization of DNA with oligonucleotides immobilized in gel: a convenient method for detecting single base substitutions. Molecular Biology (Mosk) (USSR). 25: 718-730.

Kim et al. (1999) Whole genome amplification and molecular genetic analysis of DNA from paraffin-embedded prostate adenocarcinoma tumor tissue. J Urol. 162(4): 1512-18.

Kim et al. (2000) Regulation of cell growth and HPV genes by exogenous estrogen in cervical cancer cells. Int J Gynecol Cancer. 10(2): 157-164.

Kimpton et al. (1993) Automated DNA Profiling Employing Multiplex Amplification of Short Tandem Repeat Loci. PCR Methods and Applications. 3: 13-22.

King et al. (1994) Bridging the Gap. Joining of nonhomologous ends by DNA polymerases. J. Biol. Chem. 269(18): 13061-13064.

Kinoshita et al. (1996) Strand Ligation in a Double-stranded DNA by T4 RNA Ligase. Chem. Lett. 25(9): 797-798.

Kinoshita et al. (1997) Fluorescence-, isotope- or biotin-labeling of the 5'-end of single-stranded DNA/RNA using T4 RNA ligase. Nucleic Acids Res. 25(18): 3747-8.

Klein et al. (1999) Comparative genomic hybridization, loss of heterozygosity, and DNA sequence analysis of single cells. Proc Natl Acad Sci USA. 96(8): 4494-9.

Kling J. (1994) Genetic Engineering Without Restriction. Double Twist.

Kobayashi et al. (1995) Fluorescence-based DNA minisequence analysis for detection of known single-base changes in genomic DNA. Mol Cell Probes. 9(3): 175-82.

Komura et al. (1998) Terminal transferase-dependent PCR: a versatile and sensitive method for in vivo footprinting and detection of DNA adducts. Nucleic Acids Res. 26(7): 1807-11.

Kong et al. (1993) Characterization of a DNA polymerase from the hyperthermophile archaea thermococcus litoralis. Journal of Biological Chemistry. 268(3): 1965-1975.

Kononen et al. (1998) Tissue microarrays for high-throughput molecular profiling of tumor specimens. Nat Med. 4(7): 844-7.

Kool. (1996) Circular oligonucleotides: new concepts in oligonucleotide design. Annual Rev Biomol Struct. 25: 1-28.

Kornberg et al. (1992) DNA Replication (2nd Edition). W.H. Freeman and Company, New York. Chapter 1, pp. 20-21.

Krichevsky et al. (2003) A microRNA array reveals extensive regulation of microRNAs during brain development. RNA 9: 1274-1281.

Kricka LJ. (1993) Ultrasensitive immunoassay techniques. Clin Biochem. 26(5): 325-31.

Kuchel et al. (Eds.). (1997) Schaum's Outline. Biochemistry. (2nd Edition).

Kumar et al. (1991) A simple method for introducing a thiol group at the 5'-end of synthetic oligonucleotides. Nucleic Acids Res. 19(16): 4561. No abstract available.

Kunkel et al. (1987) Rapid and efficient site-specific mutagenesis without phenotypic selection. Methods in Enzymology. 154: 367-382.

Kuukasjärvi et al. (1997) Optimizing DOP-PCR for universal amplification of small DNA samples in comparative genomic hybridization. Genes Chromosomes Cancer. 18(2): 94-101.

Kwoh et al. (1989) Transcription-based amplification system and detection of amplified human immunodeficiency virus type 1 with a bead-based sandwich hybridization format. Proc. Natl. Acad. Sci. USA 86: 1173-1177.

Laffler et al. (1993) The ligase chain reaction in DNA-based diagnosis. Ann Biol Clin (Paris). 51(9): 821-6.

Lage et al. (2003) Whole genome analysis of genetic alterations in small DNA samples using hyperbranched strand displacement amplification and array-CGH. Genome Res., 13(2): 294-307.

Lamture et al. (1994) Direct detection of nucleic acid hybridization on the surface of a charge coupled device. Nucleic Acids Research. 22(11): 2121-2125.

Landegren et al. (1988) A ligase-mediated gene detection technique. Science. 241: 1077-1080.

Landegren. (1993) Molecular mechanics of nucleic acid sequence amplification. Trends Genetics. 9(6): 199-202.

Langer et al. (1981) Enzymatic synthesis of biotin-labeled polynucleotides: novel nucleic acid affinity probes. Proc Natl Acad Sci USA. 78(11): 6633-6637.

Lantz et al. (2000) Biotechnical use of polymerase chain reaction for microbiological analysis of biological samples. Biotechnol Annu Rev. 5: 87-130.

Laval et al. (1989) Structural organization and expression of amplified chromosomal sequences, which include the rudimentary gene, in cultured Drosophila cells resistant to N-(phosphonacetyl)-L-aspartate. Mol Gen Genet. 220(1): 102-112.

Lawyer et al. (1993) High-level expression, purification, and enzymatic characterization of full-length thermus aquaticus DNA polymerase and a truncated form deficient in 5' to 3' exonuclease activity. PCR Methods Applications. 2(4): 275-287.

Lee et al. (1998) Coordinated leading and lagging strand DNA synthesis on a minicircular template. Mol Cell. (7): 1001-10.

Lee HH. (1996) Ligase chain reaction. Biologicals. 24(3):197-9.

LeFrere et al. (1992) Towards a new predictor of AIDS progression through the quantitation of HIV-1 DNA copies by PCR in HIV-infected individuals. British Journal of Haematology. 82(2): 467-471.

Lesnik et al. (1995) Relative Thermodynamic Stability of DNA, RNA, and DNA:RNA Hybrid Duplexes: Relationship with Base Composition and Structure. Biochemistry 34: 10807-10815.

Letsinger et al. (1976) Synthesis of thymidine oligonucleotides by phosphite triester intermediates. J Am Chem Soc. 98(12): 3655-3661.

Letsinger et al. (1989) Cholesteryl-conjugated oligonucleotides: synthesis, properties, and activity as inhibitors of replication of human immunodeficiency virus in cell culture. Proc Natl Acad Sci USA. 86: 6553-6556.

Letsinger et al. (1995) Use of a Stilbenedicarboxamide Bridge in Stabilizing, Monitoring, and Photochemically Altering Folded Conformations of Oligonucleotides. J. Am. Chem. Soc. 117: 7323-7328.

Li et al. (1987) Enzyme-linked synthetic oligonucleotide probes: non-radioactive detection of enterotoxigenic *Escherichia coli* in faecal specimens. Nucleic Acid Research. 15(13): 5275-5287.

Li et al. (1999) Synthesis by a Solvothermal Route and Characterization of CuInSe2 Nanowhiskers and Nanoparticles. Adv. Mater. 11(17): 1456-1459.

Lichter et al. (1990) High-resolution mapping of human chromosome 11 by in situ hybridization with cosmid clones. Science. 247: 64-69.

Lim et al. (1997) Synthesis of DNA Dumbbells: Chemical vs. Enzymatic Ligation of Self-Complementary Oligonucleotides. Nucleosides & Nucleotides. 16(1-2): 41-51.

Lin et al. (1995) Single-site polymerase chain reaction through single oligonucleotide ligation. Anal Biochem. 231(2): 449-52.

Ling et al. (1997) Approaches to DNA mutagenesis: an overview. Anal Biochem. 254(2): 157-78.

Little et al. (1999) Strand Displacement Amplification and Homogeneous Real-Time Detection Incorporated in a Second-Generation DNA Probe System, BDProbeTectET. Clin. Chem. 45(6): 777-784.

Liu et al. (1993) Mapping the 5' and 3' ends of Tetrahymena thermophila mRNAs using RNA ligase mediated amplification of cDNA ends (RLM-RACE). Nucleic Acids Res. 21(21): 4954-60.

Liu et al. (1996) Rolling Circle DNA Synthesis: Small Circular Oligonucleotides as Efficient Templates for DNA Polymerases. J Am Chem Soc. 118(7): 1587-1594.

Lizardi et al. (1997) FISH with a twist. Nat Genet. 16(3): 217-8.

Lizardi et al. (1998) Mutation detection and single-molecule counting using isothermal rolling-circle amplification. Nat Genet. 19: 225-232.

Loakes et al. (1994) 5-Nitroindole as an universal base analogue. Nucl. Acids Res. 22(20): 4039-4043.

Lockhart et al. (1996) Expression monitoring by hybridization to high-density oligonucleotide arrays. Nature Biotechnology. 14: 1675-1680.

Löffert et al. (1998) PCRoptimziation: degenerate primers. Qiagen News. (Issue 2).

Lu et al. (1993) High concentration of peripheral blood mononuclear cells harboring infectious virus correlates with rapid progression of human immunodeficiency virus Type1-related diseases. JID 168(5): 1165-8116.

Lukyanov et al. (1996) Molecule by molecule PCR amplification of complex DNA mixtures for direct sequencing: an approach to in vitro cloning. Nucleic Acids Research. 24(11): 2194-2195.

Luo et al. (1996) Improving the fidelity of thermus thermophilus DNA ligase. Nucl Acids Res. 24(14): 3071-3078.

Lyons et al. (1994) Immunosuppressant FK506 promotes neurite outgrowth in cultures of PC12 cells and sensory ganglia. Proc Natl Acad Sci USA. 91(8): 3191-3195.

MacKellar et al. (1992) Synthesis and physical properties of anti-HIV antisense oligonucleotides bearing terminal lipophilic groups. Nucleic Acids Res. 20(13):3411-7.

Mahadeva et al. (1998) A simple and efficient method for the isolation of differentially expressed genes. J Mol Biol. 284(5): 1391-8.

Malboeuf et al. (2001) Thermal effects on reverse transcription: improvement of accuracy and processivity in cDNA synthesis. Biotechniques. 30(5): 1074-8, 1080, 1082, passim.

Maniatis et al. (1982) Molecular Cloning: A Laboratory Manual. (Cold Spring Harbor Laboratory) Eds, pp. 280-281.

Manoharan et al. (1992) Chemical modifications to improve uptake and bioavailability of antisense oligonucleotides. Ann NY Acad Sci. 660: 306-309.

Manoharan et al. (1993) Introduction of a lipophilic thioether tether in the minor groove of nucleic acids for antisense applications. Bioorg Med Chem Let. 3(12): 2765-2770.

Manoharan et al. (1994) Cholic acid-oligonucleotide conjugates for antisense applications. Bioorg Med Chem Let. 4(8): 1053-1060.

Manoharan et al. (1995) Lipidic nucleic acids. Tetra Lett. 36(21): 3651-3654.

Manoharan et al. (1995) Oligonucletoide conjugates: alteration of the pharmacokinetic properties of antisense agents. Nucleosides & Nucleotides. 14: 969-973.

Marshall et al. (1994) Detection of HCV RNA by the asymmetric gap ligase chain reaction. PCR Methods and Applications. 4: 80-84.

Marshall et al. (1997) A biopolymer by any other name would bind as well: a comparison of the ligand-binding pockets of nucleic acids and proteins. Structure. 5(6): 729-734.

Maskos et al. (1992) Oligonucleotide hybridizations on glass supports: a novel linker for oligonucleotide synthesized in situ. Nucl. Acids Res. 20(7): 1679-1684.

Mathur et al. (2000) Cervical epidermal growth factor-receptor (EGF-R) and serum insulin-like growth factor II (IGF-II) levels are potential markers for cervical cancer. Am J Reprod Immunol. 44(4): 222-30.

Matray et al. (1998) Selective and Stable DNA Base Pairing without Hydrogen Bonds. J Am. Chem. Soc. 120(24): 6191-6192.

Matray et al. (1999) A specific partner for abasic damage in DNA. Nature. 399(6737): 704-8.

Matsumoto et al. (1989) Primary structure of bacteriophage M2 DNA polymerase: conserved segments within protein-priming DNA polymerases and DNA polymerase I of *Escherichia coli*. Gene. 84(2): 247-255.

Matteucci et al. (1981) Synthesis of deoxyoligonucleotides on a polymer support. J Am Chem Soc. 103:3185-3191.

Matz et al. (1999) Amplification of cDNA ends based on template-switching effect and step-out PCR. Nucleic Acid Research. 27(6): 1558-1560.

McCoy et al. (1980) T4 ribonucleic acid ligase joins single-strand oligo (deoxyribonucleotides). Biochemistry. 19(4): 635-42.

McCray et al. (1980) A new approach to time-resolved studies of ATP-requiring biological systems: laser flash photolysis of caged ATP. Proc Natl Acad Sci USA. 77(12): 7237-7241.

McGraw et al. (1990) Sequence-dependent oligonucleotide-target duplex stabilities: rules from empirical studies with a set of twenty-mers. Biotechniques. 8(1): 674-678 (1990).

Melton et al. (1984) Efficient in vitro synthesis of biologically active RNA and RNA hybridization probes from plasmids containing a bacteriophage SP6 promoter. Nucleic Acids Research. 12(18): 7035-7056.

Mendoza et al. (1999) High-throughput microarray-based enzyme-linked immunosorbent assay (ELISA). Biotechniques. 27(4): 778-80, 782-6, 788.

Metzker et al. (1994) Termination of DNA synthesis by novel 3'-modified- deoxyribonucleoside 5'-triphosphates. Nucleic Acids Research. 22(20): 4259-4267.

Milla et al. (1998) Use of the restriction enzyme AvaI and exo-Bst polymerase in strand displacement amplification. Biotechniques, 24(3): 392-96.

Mishra et al. (1995) Improved leishmanicidal effect of phosphorotioate antisense oligonucleotides by LDL-mediated delivery. Biochim Biophys Acta. 1264(2): 229-37.

Monji et al. (1987) A novel immunoassay system and bioseparation process based on thermal phase separating polymers. Appl Biochem Biotechnol. 14(2): 107-20.

Moore et al. (1992) Site-specific modification of pre-mRNA: the 2'-hydroxyl groups at the splice sites. Science. 256(5059): 992-7.

Moran et al. (1996) Non-hydrogen bonding 'terminator' nucleosides increase the 3'-end homogeneity of enzymatic RNA and DNA synthesis. Nucleic Acids Research. 24(11): 2044-2052.

Moretti et al. (1998) Enhancement of PCR amplification yield and specificity using AmpliTaq Gold DNA polymerase. Biotechniques. 25(4): 716-22.

Morvan et al. (1986) alpha-DNA. I. Synthesis, characterization by high field 1H-NMR, and base-pairing properties of the unnatural hexadeoxyribonucleotide alpha-[d(CpCpTpTpCpC)] with its complement beta-[d(GpGpApApGpG)]. Nucleic Acids Res. 14(12): 5019-35.

Mujumdar et al. (1989) Cyanine dye labeling reagents containng isothiocyanate groups. Cytometry. 10: 11-19.

Mullenix et al. (2001) Allergen-specific IgE detection on microarrays using rolling circle amplification: correlation with in vitro assays for serum IgE. Clinical Chemistry. 47(10): 1926-1929.

Myakishev et al. (2001) High-throughput SNP genotyping by allele-specific PCR with universal energy-transfer-labeled primers. Genome Res. 11(1):163-169.

Myers et al. (1991) Reverse transcription and DNA amplification by a Thermus thermophilus DNA polymerase. Biochemistry. 30(31): 7661-6.

Nagamine et al. (2001) Loop-mediated isothermal amplification reaction using a nondenatured template. Clin Chem., 47(9): 1742-3.

Nallur et al. (2001) Signal amplification by rolling circle amplification on DNA microarrays. Nucl. Acids. Res. 29(23): e118.

Narang et al. (1980) Chemical synthesis of deoxynucleotides by the modified tester method. Methods Enzymology. 65: 610-620.

Naritsin et al. (1991) Melting of oligodeoxynucleotides with various structures. J. Biomol. Struct. Dyn. 8(4): 813-25.

Navarro et al. (1996). A general strategy for cloning viroids and other small circular RNAs that uses minimal amounts of template and does not require prior knowledge of its sequence. J Virol Methods. 56(1): 59-66.

Nazarenko et al. (1997) A closed tube format for amplification and detection of DNA based on energy transfer. Nucleic Acids Res. 25(12): 2516-21.

Nelson et al. (2002) TempliPhi, phi29 DNA polymerase based rolling circle amplification of templates for DNA sequencing. Biotechniques. 32: S44-S47.

New England BioLabs. Polymerase from NEB printed information from New England BioLabs webpage (3 total pages), retrieved on Jul. 26, 2007 at http://www.neb.com/nebecomm/tech_reference/polymerases/polymerase_from_neb.asp.

New England BioLabs. Product Information for M-MuLV Reverste Trasncriptase from New England BioLabs website, retrieved on Apr. 4, 2007.

Newton et al. (1989) Analysis of any point mutation in DNA. The amplification refractory mutation system (ARMS). Nucl. Acids Res. 17(7): 2503-2516.

Nichols et al. (1994) A universal nucleoside for use at ambiguous sites in DNA primers. Nature. 369(6480): 492-493.

Nielsen et al. (1991) Sequence-Selective Recognition of DNA by Strand Displacement with a Thymine-Substituted Polymide. Science 254: 1497-1500.

Nielsen et al. (1993) Peptide nucleic acids (PNAs): potential antisense and anti-gene agents. Anti-Cancer Drug Design. 8: 53-63.

Nielsen et al. (1994) Peptide nucleic acid (PNA). A DNA mimic with a peptide backbone. Bioconjugate Chemistry. 5: 3-7.

Nikiforov et al. (1994) Genetic bit analysis: a solid phase method for typing single nucleotide polymorphisms. Nucleic Acids Research. 22(20): 4167-4175.

Nikiforov et al. (1994) The use of phosphorothioate primers and exonuclease hydrolysis for the preparation of single-stranded PCR products and their detection by solid-phase hybridization. PCR Methods and Applications. 3: 285-291.

Nilsson et al. (1994) Padlock Probes: Circularizing Oligonucleotides for Localized DNA Detection. Science 265(5181): 2085-2088.

Nilsson et al. (1997) Padlock probes reveal single-nucleotide differences, parent of origin and in situ distribution of centromeric sequences in human chromosomes 13 and 21. Nature Genet. 16: 252-255.

Nilsson et al. (2002) Real-time monitoring of rolling-circle amplification using a modified molecular beacon design. Nucleic Acids Res. 30(14): e66.

Notomi et al. (2000) Loop-mediated isothermal amplification of DNA. Nucleic Acids Res., 28(12): E63.

Nuovo et al. (1999) In Situ Amplification Using Universal Energy Transfer-labeled Primers. J. Histochem. Cytochem. 47(3): 273-279.

Nycz et al. (1998) Quantitative reverse transcription strand displacement amplification: quantitation of nucleic acids using an isothermal amplification technique. Anal Biochem. 259(2): 226-34.

Oberhauser et al. (1992) Effective incorporation of 2'-O-methyl-oligoribonucleotides into liposomes and enhanced cell association through modification with thiocholesterol. Nucleic Acids Res. 20(3): 533-8.

Oda et al. (1999) Accurate quantitation of protein expression and site-specific phosphorylation. Proc Natl Acad Sci USA. 96: 6591-6596.

Okayama et al. (1982) High-efficiency cloning of full-length cDNA. Mol Cell Biol. 2(2): 161-170.

Ørum et al. (1993) Single base pair mutation analysis by PNA directed PCR clamping. Nucleic Acids Research. 21(23): 5332-5336.

Ott et al. (1987) Protection of oligonucleotide primers against degradation by DNA polymerase I. Biochemistry. 26(25): 8237-41.

Oyama et al. (1988) Avian myeloblastosis virus reverse transcriptase is easier to use than the Klenow fragment of DNA polymerase I for labeling the 3'-end of a DNA fragment. Anal Biochem. 172(2): 444-50.

Panasenko et al. (1978) A simple, three-step procedure for the large scale purification of DNA ligase from a hybird 1 lysogen construction in vitro. Journal Biological Chemistry. 253(13): 4590-4592.

Park et al. (1996) Detection of hepatitis C virus RNA using ligation-dependent polymerase chain reaction in formalin-fixed, paraffin-embedded liver tissues. Am J Pathol. 149(5): 1485-91.

Parker et al. (1991) Targeted gene walking polymerase chain reaction. Nucl Acids Res. 19: 3055-3060.

Parra et al. (1993) High resolution visual mapping of stretched DNA by fluorescent hybridization. Nat Genet. 5(1): 17-21.

Partha et al. (1990) Novel Thymidine Analogues via Reaction of Unprotected 5'-Deoxy-5'-iodothymidine with Dianions. vol. 31, Issue 10, pp. 1777-1780.

Patel et al. (1996) Formation of chimeric DNA primer extension products by template switching onto an annealed downstrem oligonucleotide. Proc. Natl. Acad. Sci. USA. 93(7): 2969-2974.

Patton et al. (1995) Components of the Protein Synthesis and Folding Machinery are Induced in Vascular Smooth Muscle Cells by Hypertrophic and Hyperplastic Agents. J. Biol. Chem. 270(36): 21404-21410.

Patton. (1999) Proteome analysis II. Protein subcellular redistribution: linking physiology to genomics via the proteome and separation techniques involved. J Chromatogr. B 722: 203-223.

Patton. (2000) Making Blind Robots See: The Snyergy Between Fluorscent Dyes and Imaging Devices in Automated Proteomics. Biotechniques 28(5): 944-957.

Paulson et al. (1999) Loss of heterozygosity analysis using whole genome amplification, cell sorting, and fluorescence-based PCR. Genome Res. 9(5): 482-91.

Paunio et al. (1996) Preimplantation diagnosis by whole-genome amplification, PCR amplification, and solid-phase minisequencing of blastomere DNA. Clin Chem. 42(9): 1382-90.

Pease et al. (1994) Light-generated oligonucleotide arrays for rapid DNA sequence analysis. Proc Natl Acad Sci USA. 91(11): 5022-5026.

Petric et al. (1991) Ligation with T4 RNA ligase of an oligodeoxyribonucleotide to covalently-linked cross-sectional base-pair analogues of short, normal, and long dimensions. Nucleic Acids Res. 19(3): 585-90.
Piatak et al. (1993) High levels of HIV-1 in plasma during all stages of infection determined by competitive PCR. Science. 259: 1749-1754.
Pieles et al. (1989) Psoralen covalently linked to oligodeoxyribonucleotides: synthesis, sequence specific recognition of DNA and photo-cross-linking to pyrimidine residues of DNA. Nucleic Acids Res. 17(1): 285-99.
Pillai, V.N. Rajasekharan. (1980) Photoremovable protecting groups in organic synthesis. Synthesis. Jan. 1980 (1):1-26.
Pless et al. (1975) Solid support synthesis of oligothymidylates using phosphorochloridates and 1-alkylmidazoles. Nucl Acids Res. 2(6): 773-786.
Pokrovskaya et al. (1994) In vitro transcription: preparative RNA yields in analytical scale reactions. Analytical Biochemistry. 220: 420-423.
Porstmann et al. (1985) Quantitation of 5-bromo-2-deoxyuridine incorporation into DNA: an enzyme immunoassay for the assessment of the lymphoid cell proliferative response. J. Immunol Meth. 82: 169-179.
Prakash et al. (1991) Molecular recognition by circular oligonucleotides. Strong binding of single-stranded DNA and RNA. J. Chem. Soc., Chem. Commun., 1161-1163.
Prakash et al. (1992) Structural Effects in the Recognition of DNA by Circular Oligonucleotides. J. Amer. Chem. Soc. 114: 3523-3527.
Prober et al. (1987) A system for rapid DNA sequencing with fluorescent chain-terminating dideoxynucleotides. Science. 238: 336-341.
Pruckler et al. (1995) Comparison of Legionella pneumophila isolates by arbitrarily primed PCR and pulsed-field gel electrophoresis: analysis from seven epidemic investigations. J Clin Microbiol. 33(11): 2872-5.
Ramsing et al. (1989) Helix-Coil Transsition of Parallel-Stranded DNA. Thermodynamics of Hairpin and Linear Duplex Oligonucleotides. Biochemistry 28: 9528-9535.
Ray et al. (1990) Novel Thymidine Analogues via Reaction of Unprotected 5'-Deoxy-5'- Iodothymidine with Dianions. Heterocycles. 31(10): 1777-1780.
Rector et al. (2004) A sequence-independent strategy for detection and cloning of circular DNA virus genomes by using multiply primed rolling-circle amplification. J Virol. 78(10): 4993-4998.
Reese et al. (1999) The H-phosphonate approach to the solution phase synthesis of linear and cyclic oligoribonucleotides. Nucleic Acids Res. 27(4): 963-71.
Richards et al. (1997) Conditional mutator phenotypes in hMSH2-deficient tumor cell lines. Science. 277: 1523-1526.
Ried et al. (1982) Simultaneous visualization of seven different DNA probes by in situ hybridization using combinational fluorescence and digital imaging microscopy. Proc Natl Acad Sci USA. 89(4): 1388-1392.
Rigler et al. (1995) Difference in the mechanism of stimulation of T7 DNA polymerase by two binding modes of *Escherichia coli* single-stranded DNA-binding protein. Journal of Biological Chemistry. 270(15): 8819-8919.
Robins et al. (1988) Fluorination at C5' of nucleosides. Synthesis of the new class of 5'-fluoro-5'-S-aryl (alkyl) thionucleosides from adenosine. Tetrahedron Letters: 29(45): 5729-5732.
Rodriguez et al. (1998) Large scale isolation of genes as DNA fragment lengths by continuous elution electrophoresis through an agarose matrix. Electrophoresis. 19(5): 646-52.
Rossi et al. (1997) Functional characterization of the T4 DNA ligase: a new insight into the mechanism of action. Nucleic Acids Res. 25(11): 2106-13.
Rubin et al. (1995) Convergent DNA synthesis: a non-enzymatic dimerization approach to circular oligodeoxynucleotides. Nucleic Acids Res. 23(17): 3547-53.
Rudbeck et al. (1998) Rapid, simple alkaline extraction of human genomic DNA from whole blood, buccal epithelial cells, semen and forensic stains for PCR. Biotechniques. 25(4): 588-90, 592.

Ruiz et al. (1998) Homology-dependent gene silencing in Paramecium. Mol Biol Cell. 9(4): 931-43.
Rychlik et al. (1990) Optimizaton of the annealing temperature for DNA amplification in vitro. Nucleic Acids Research. 18(21): 6409-6412.
Ryo et al. (2000) A Modified Serial Analysis of Gene Expression That Generates Longer Sequence Tags by Nonpalindromic Cohesive Linker Ligation. Analytical Biochemistry. 277, 160-162.
Rys et al. (1993) Preventing False Positives: Quantitative Evaluatio of Three Protocols for Inactivation of Polymerase Chain Reaction Amplication Products. J. Clin. Microbiol. 31(9): 2356-2360.
Saiki et al. (1985) Enzymatic Amplifications of beta-Globin Genomic Sequences and Restriction Site Analysis for Diagnosis of Sickle Cell Anemia. Science 230: 1350-1354.
Saiki et al. (1988) Primer-Directed Enzymatic Amplification of DNA with a Thermostable DNA Polymerase. Science. 239: 487-491.
Saison-Behmoaras et al. (1991) Short modified antisense oligonucleotides directed against Ha-ras point mutation induce selective cleavage of the mRNA and inhibit T24 cells proliferation. EMBO J. 10(5): 1111-1118.
Saksela et al. (1994) Human immunodeficiency virus type 1 mRNA expression in peripheral blood cells predicts disease progression independently of the numbers of CD4+ lymphocytes. Proc Natl Acad Sci USA. 91(3): 1104-1108.
Salunkhe et al. (1992) Control of folding and binding of oligonucleotides by use of a nonnucleotide linker. J. Am. Chem. Soc. 114: 8768-8772.
Sambrook et al. *Molecular Cloning: A Laboratory Manual.* 2nd Edition (Cold Spring Harbor Laboratory Press, Cold Spring Harbor, N.Y., 1989) Chapters 5, 6).
Sanghvi. (1993) Heterocyclic base modifications in nucleic acids and their applications in antisense oligonucleotides. Antisense Research and Applications. (Crooke et al, eds., CRC Press) Chapters 15-16, pp. 273-301.
Sano et al. (1988) Detection of heavy methylation in human repetitive DNA subsets by a monoclonal antibody against 5-methylcytosine. Biochim Biophys Acta. 951: 157-165.
Santoro et al. A general purpose RNA-cleaving DNA enzyme. PNAS 94: 4262 (1997).
Saris et al. (1982) Blotting of RNA onto ion exchange paper allowing subsequent characterization by in situ translation in addition to blot hybridization. Nucleic Acids Res. 10(16): 4831-4843.
Sasvari-Szekely et al. (2000) Rapid genotyping of factor V Leiden mutation using single-tube bidirectional allele-specific amplification and automated ultrathin-layer agarose gel electrophoresis. Electrophoresis. 21(4): 816-21.
Schaefer BC. (1995) Revolutions in rapid amplification of cDNA ends: new strategies for polymerase chain reaction cloning of full-length cDNA ends. Anal Biochem. 227(2): 255-73.
Schena et al. (1994) Parallel human genome analysis: microarray-based expression monitoring of 1000 genes. Proc Natl Acad Sci USA. 93: 10614-10619.
Schena et al. (1995) Quantitative monitoring of gene expression patterns with a complementary DNA microarray. Science. 270: 467-470.
Schena et al. (2000) Genes, genomes, and chips. Chapter 1, pp. 1-16.
Schenborn et al. (1985) A novel transcription property of SP6 and T7 RNA polymerases: dependence on template structure. Nucleic Acids Research. 13(17): 6223-6236.
Schenk et al. (1995) The accessibility of thiophosphorylated groups in DNA fragments to the enzymatic activity of ligases and restriction endonuclease Bbs I. Biochem Mol Biol Int. 36(5): 1037-43.
Schnierle et al., Cap-specific mRNA (nucleoside-02'-)-methyltransferase and poly(A) polymerase stimulatory activities of vaccinia virus are mediated by a single protein. PNAS 89 (7) : 2897 (1992).
Schwarz. (1990) Improved yields of long PCR products using gene 32 protein. Nucl Acids Res. 18(4): 1079.
Schweitzer et al. (2000) Immunoassays with rolling circle DNA amplification: a versatile platform for ultrasensitive antigen detection. PNAS. 97(18): 10113-10118.
Schweitzer et al. (2001) Combining nucleic acid amplification and detection. Curr Opin Biotechnol. 12(1): 21-27.

Schweitzer et al. (2002) Multiplexed protein profiling on microarrays by rolling-circle amplification. Nat. Biotech. 20: 359-365.

Séquin, Urs. (1974) Nucleosides and Nucleotides. Part 7. Four dithymidine monophosphates with different anomeric configurations, their synthesis and behaviour towards phosphodiesterases Helvetica Chimica Acta. 57: 68-81.

Shea et al. (1990) Synthesis, hybridization properties and antiviral activity of lipid-oligodeoxynucleotide conjugates. Nucl Acids Res. 18(13): 3777-3783.

Shumaker et al. (1996) Mutation detection by solid phase primer extension. Human Mutation. 7(4): 346-354.

Siegal et al. (1992) A Novel DNA Helicase from Calf Thymus. J. Biol. Chem. 267(19): 13629-13635.

Silber et al. (1972) Purification and properties of bacteriophage T4-induced RNA ligase. Proc Natl Acad Sci U S A. 69(10): 3009-13.

Silzel et al. (1998) Mass-sensing, multianalyte microarray immunoassay with imaging detection. Clin Chem. 44(9): 2036-43.

Simpson. (1997) The natural somatic mutation frequency and human carcinogenesis. Adv Cancer Res. 71: 209-240.

Sinha et al. (1988) The preparation and application of functionalised synthetic oligonucleotides: III. Use of H-phosphonate derivatives of protected amino-hexanol and mercapto-propanol or -hexanol. Nucleic Acids Res. 16(6): 2659-69.

Skaliter et al. (1994) Rolling circle DNA replication in vitro by a complex of herpes simplex virus type 1-encoded enzymes. Proc Natl Acad Sci USA. 91(22): 10665-10669.

Skerra A. (1992) Phosphorothioate primers improve the amplification of DNA sequences by DNA polymerases with proofreading activity. Nucleic Acids Res. 20(14): 3551-54.

Smart Notes from Cepheid. Sensitivity and Specificity Utilizing Amplifluor™ Primers. (2 pages).

Sørensen et al. (2000) Branched oligonucleotides containing bicyclic nucleotides as branching points and DNA or LNA as triplex forming branch. Bioorg Med Chem Lett. 10(16): 1853-1856.

Southern EM. (1975) Detection of specific sequences among DNA fragments separated by gel electrophoresis. J Mol Biol. 98(3): 503-17.

Speicher et al. (1996) Karyotyping human chromosomes by combinatorial multi-fluor FISH. Nature Genetics. 12(4): 368-375.

Sperling et al. (2002) Random sequencing of Paramecium somatic DNA. Eukaryot Cell. 1(3): 341-52.

Stefano et al. (1997) Rapid and sensitive detection of Chlamydia trachomatis using a ligatable binary RNA probe and Q beta replicase. Mol Cell Probes. 11(6): 407-26.

Stein et al. (1991) Mode of action of 5'-linked cholesteryl phosphorothioate oligodeoxynucleotides in inhibiting syncytia formation and infection by HIV-1 and HIV-2 in vitro. Biochemistry. 30(9): 2439-44.

Steller et al. (1995) Insulin-like growth factor II mediates epidermal growth factor-induced mitogenesis in cervical cancer cells. Proc Natl Acad Sci U S A. 92(26): 11970-4.

Stewart et al. (1998) A quantitative assay for assessing allelic proportions by iterative gap ligation.b Nucleic Acids Res. 26(4):961-6.

Stimpson et al. (1995) Real-time detection of DNA hybridization and metling on oligonucleotide arrays by using optical wave guides. Proc. Natl. Acad. Sci. USA 92(14): 6379-6383.

Stratagene Catalog. (1988) Gene characterization Kits, Table of Contents. p. 39.

Stratagene Catalog. (1992) Sequencing Thermalbase® Sequencing Kit, p. 76.

Stratagene Catalog. (1999) RT-PCR Systems and Kits, Stratagene Catalog, 1999 pp. 154-155.

Strauss et al. (1993) Quantitative measure of calretinin and b-actin mRNA in rat brain micropunches without prior isolation of RNA. Mol Brain Res. 20: 229-239.

Strong et al. (1997) Marked improvement of PAC and BAC cloning is achieved using electroelution of pulsed-field gel-separated partial digests of genomic DNA. Nucleic Acids Res. 25(19):3959-3961.

Studier et al. (1990) Use of T7 RNA Polymerase to Direct Expression of Cloned Genes. Meth. Enzymol. 185: 60-89.

Stump et al. (1999) The use of modified primers of eliminate cycle sequencing artifacts. Nucl. Acids Res. 27(23): 4642-4648.

Suzuki et al. (1994) Mechanistic studies on depurination and apurinic site chain breakage in oligodeoxyribonucleotides. Nucleic Acids Res. 22(23): 4997-5003.

Svinarchuk et al. (1993) Inhibition of HIV proliferation in MT-4 cells by antisense oligonucleotide conjugated to lipophilic groups. Biochimie. 75: 49-54.

Syvanen et al. (1986) Fast quantification of nucleic acid hybrids by affinity-based hybrid collection. Nucleic Acids Research. 14(12): 5037-5049.

Tabor et al. (1987) Selective oxidation of the exonuclease domain of bacteriophage T7 DNA polymerase. J. Biol. Chem. 262: 15330-15333.

Tabor et al. (1989) Effect of manganese ions on the incorporation of dideoxynucleotides by bacteriophage T7 DNA polymerase and *Escherichia coli* DNA polymerase I. Proc. Natl. Acad. Sci. USA. 86, 4076-4080.

Tabor et al. (1989) Selective inactivation of the exonuclease activity of bacteriohage T7 DNA polymerase by in vitro mutagenesis. J Biol Chem. 264(11): 6447-6458.

Takasugi et al. (1991) Sequence-specific photo-induced cross-linking of the two strands of double-helical DNA by a psoralen covalently linked to a triple helix-forming oligonucleotide. Proc Natl Acad Sci U S A. 88(13):5602-6.

Takeshita et al. (1987) Oligodeoxynucleotides containing synthetic abasic sites. Model substrates for DNA polymerases and apurinic/apyrimidinic endonucleases. J Biol Chem. 262(21): 10171-9.

Tanaka et al. (1989) Cleavage of a Nucleosidic Oxetane with Carbanions: Synthesis of a Highly Promising Candidate for Anti-HIV Agents—a Phosphonate Isotere of AZT 5'-Phosphate. Tetrahedron Lett. 30(19): 2567-2570.

Taylor, Richard (Ed.) (1991) .*Protein immobilization: fundamentals and applications*, M. Dekker, New York, 1991.

Telenius et al. (1992) Degenerate oligonucleotide-primed PCR: general amplification of target DNA by a single degenerate primer. Genomics. 13(3): 718-25.

Tenover et al. (1994) Comparison of traditional and molecular methods of typing isolates of *Staphylococcus aureus*. J. Clin. Microbiol. 32(2): 407-15.

Tessier et al. (1996) Ligation of single-stranded oligodeoxyribonucleotides by T4 RNA ligase. Anal Biochem. 158(1): 171-8.

Theillet C. (1998) Full speed ahead for tumor screening. Nat Med. 4(7): 767-8.

Thelwell et al. (2000) Mode of action and application of Scorpion primers to mutation detection. Nucl. Acids Res. 28(19):3752-3761.

Thomas et al. (1997) Cascade rolling circle amplification, a homogeneous fluorescence detection system for DNA diagnostics. Clin Chem. 43: 2219-2220.

Thomas et al. (1999) Amplification of padlock probes for DNA diagnostics by cascade rolling circle amplification or the polymerase chain reaction. Arch Pathol Lab Med. 123(12): 1170-1176.

Thorbjarnardottir et al. (1995) Cloning and sequence analysis of the DNA ligase-encoding gene of *Rhodothermus marinus*, overproduction, purification and characterization of two thermophilic DNA ligases. Gene 161: 1-6.

Thuong et al. Solid phase synthesis of oligo-α- and oligo-β-deoxynucleotidescovalently linked to an acridine. pp. 5905-5908. Tetrahedron Lett. 29(46): 5905-5908.

Tobe et al. (1996) Single-well genotyping of diallelic sequence variations by a two-color ELISA-based oligonucleotide ligation assay. Nucleic Acids Res. 24(19): 3728-32.

Troutt et al. (1992) Ligation-anchored PCR: a simple amplification technique with single-sided specificity. Proc Natl Acad Sci U S A. 89(20):9823-5.

Tsurumi et al. (1993) Functional interaction between Epstein-Barr virus DNA polymerase catalytic subunit and its accessory subunit in vitro. Journal of Virology. 67(12): 7648-7653.

Tuma et al. (1999) Characterization of SYBR Gold nucleic acid gel stain: a dye optimized for use with 300-nm ultraviolet transilluminators. Anal Biochem. 268(2): 278-88.

Tyagi et al. (1996) Extremely sensitive, background-free gene detection using binary probes and beta replicase. Proc Natl Acad Sci U S A. 93(11): 5395-5400.

Tyagi et al. (1996) Molecular beacons: probes that fluoresce upon hybridization. Nature Biotechnology. 14: 303-308.

Uemori et al. (1993) Cloning of the DNA Polymerase Gene of *Bacillus caldotenax* and Characterizaion of the Gene Product. J. Biochem. 113: 401-410.

Unrau et al. (1994) Non-cloning amplification of specific DNA fragments from whole genomic DNA digests using DNA 'indexers'. Gene. 145(2): 163-9.

Välimaa et al. (1998) Detection of HLA-B27 alleles by group-specific amplification and time-resolved fluorometry. J Immunol Methods. 219(1-2): 131-137.

Van Gelder et al. (1990) Amplified RNA synthesized from limited quantities of heterogeneous cDNA. Proc. Natl. Acad. Sci. USA. 87, 1663-1667.

Velculescu et al. (1995) Serial Analysis of Gene Expression. Science 270: 484-487.

Villemain et al. (1996) the N-terminal B-domain of T4 gene 32 protein modulates the lifetime of cooperatively bound Gp32-ss nucleic acid complexes. Biochemistry. 35: 14395-14404.

Vincent et al. (2004) Helicase-dependent isothermal DNA amplification. EMBO Rep., 5(8): 795-800.

Vogelstein et al. (1980) Supercoiled loops and eucaryotic DNA replication. Cell. 22: 79-85.

Voisey et al. (2001) Interrogation of multimeric DNA amplification products by competitive primer extension using bst DNA polymerase (large fragment). Biotechniques. 31(5): 1122-4, 1126, 1128-29.

Waggoner. (1995) Covalent labeling of proteins and nucleic acids with fluorophores. Meth Enzymology. 246: 362-373.

Walder et al. (1993) Use of PCR primers containing a 3'-terminal ribose residue to prevent cross-contamination of amplified sequences. Nucleic Acids Res. 21(18): 4339-43.

Walker et al. (1992) Isothermal in vitro amplification of DNA by a restriction enzyme/DNA polymerase system. Proc Natl Acad Sci USA. 89: 392-396.

Walker et al. (1992) Strand displacement amplification—an isothermal, in vitro DNA amplification technique. Nucleic Acids Research. 20(7): 1691-1696.

Walker et al. (1994) Multiplex strand displacement amplification (SDA) and detection of DNA sequences from Mycobacterium tuberculosis and other mycobacteria. Nucleic Acids Res. 22(13): 2670-2677.

Walker et al. (1996) Detection of Mycobacterium tuberculosis DNA with thermophilic strand displacement amplification and fluorescence polarization. Clin. Chem. 42(10): 1604-1608.

Walter et al. (1994) Strand displacement amplification as an in vitro model for rolling-circle replication: deletion formation and evolution during serial transfer. Proc Natl Acad Sci USA. 91: 7937-7941.

Wang et al. (1989) Quantitation of mRNA by the polymerase chain reaction. Proc Natl Acad Sci U S A. 86(24): 9717-21.

Wang et al. (1994) Circular RNA oligonucleotide. Synthesis, nucleic acid binding properties, and a comparison with circular DNAs. Nucl. Acids. Res. 22(12): 2326-2333.

Wang et al. (1998) Large-scale identification, mapping, and genotyping of single-nucleotide polymorphisms in the human genome. Science. 280: 1077-1082.

Wang et al. (1998) Oligoribonucleotide circularization by 'template-mediated' ligation with T4 RNA ligase: synthesis of circular hammerhead ribozymes. Nucleic Acids Res. 26(10): 2502-4.

Wang et al. (2004) DNA amplification method tolerant to sample degradation. Genome Res., 14(11): 2357-66.

Wansink et al. (1993) Fluorescent labeling of nascent RNA reveals transcription by RNA polymerase II in domains scattered throughout the nucleus. Journal of Cell Biology. 122(2): 283-293.

Warnecke et al. (1997) Detection and measurement of PCR bias in quantitative methylation analysis of bisulphite-treated DNA. Nucleic Acids Res. 25(21): 4422-26.

Welford et al. (1998) Detection of differentially expressed genes in primary tumor tissues using representational differences analysis coupled to microarray hybridization. Nucleic Acids Res. 26(12): 3059-65.

Wells et al. (1999) Detailed chromosomal and molecular genetic analysis of single cells by whole genome amplification and comparative genomic hybridisation. Nucleic Acids Res. 27(4): 1214-8.

Wells et al. (2000) Comprehensive chromosomal analysis of human preimplantation embryos using whole genome amplification and single cell comparative genomic hybridization. Mol Hum Reprod. 6(11): 1055-62.

Wemmer et al. (1985) Preparation and melting of single strand circular DNA loops. Nucleic Acids Res. 13(23): 8611-21.

Wharam et al. (2001) Specific detection of DNA and RNA targets using a novel isothermic nucleic acid amplification assay based on the formation of a three-way junction structure. Nucleic Acid Research. 29(11): e54.

White et al. (1991) Concatemer chain reaction: a Taq DNA polymerase-mediated mechanism for generating long tandemly repetitive DNA sequences. Anal Biochem. 199(2): 184-90.

Whiting et al. (1994) Strand displacement synthesis capability of Moloney murine leukemia virus reverse transcriptase. J. Virol. 68(8): 4747-58.

Wiedmann et al. (1994) Ligase chain reaction (LCR)—overview and applications. PCR Methods and Applications. (Cold Spring Harbor Laboratory Press, Cold Spring Harbor, NY) [pp. S51-S64].

Wiegant et al. (1992) High-resolution in situ hybridization using DNA halo preparations. Hum Mol Genet. 1(8): 587-91.

Will et al. (1991) The synthesis of oligonucleotides that contain 2,4-dinitrophenyl reporter groups. Carbohydr Res. 216: 315-22.

Wilson et al. (1993) Enzyme complex amplification—a signal amplification method for use in enzyme immunoassays. Anal Biochem. 209(1): 183-187.

Wiltshire et al. (2000) Detection of multiple allergen-specific IgEs on microarrays by immunoassay with rolling circle amplification. Clin Chem. 46(12): 1990-1993.

Winn-Deen et al. (1993) Non-radioactive detection of mycobacterium tuberculosis LCR products in a microtitre plate format. Molecular and Cellular Probes. (England) 7(3): 179-186.

Wirth et al. (1995) Staining methods in gel electrophoresis, including the use of multiple detection methods. J. Chromatogr. 698: 123-143.

Wolf et al. (1997) The Cloning Debates and Progress in Biotechnology. Clinical Chemistry. 43:2019-2020.

Xu et al. (2001) Nonenzymatic autoligation in direct three-color detection of RNA and DNA point mutations. Nat Biotechnol. 19(2): 148-52.

Yang et al. (1999) Combining SSH and cDNA microarrays for rapid identification of differentially expressed genes. Nucleic Acids Res. 27(6): 1517-23.

Yates et al. (2001) Quantitative detection of hepatitis B virus DNA by real-time nucleic acid sequence-based amplification with molecular beacon detection. J Clin Microbiol. 39(10): 3656-65.

Young et al. (1985) Quantitative analysis of solution hybridization. Nucleic Acid Hybridisation: A Practical Approach. (IRL Press) pp. 47-71.

Yu et al. (1994) Cyanine dye dUTP analogs for enzymatic labeling of DNA probes. Nucleic Acids Research. 22(15): 3226-3232.

Yunis et al. (1978) The characterization of high-resolution G-banded chromosomes of man. Chromosoma. 67(4): 293-307.

Zehavi et al. (1972) Light sensitive glycosides. I. 6-nitroveratryl b-D-glucopyranoside and 2-nitrobenzyl b-D-glucopyranoside. J. Organic Chem. 37(14): 2281-2285.

Zehavi et al. (1972) Light-sensitive glycosides. II. 2-Nitrobenzyl 6-deoxy-.alpha.-L-mannopyranoside and 2-nitrobenzyl 6-deoxy-.beta.-L-galactopyranoside Uri. J. Org. Chem., 37 (14), pp. 2285-2288.

Zhang et al. (1990) Amplification of target-specific, ligation-dependent circular probe. Gene 211: 277-285.

Zhang et al. (1992) Whole genome amplification from a single cell: Implications for genetic analysis. Proc. Natl. Acad. Sci. USA 89: 5847-5851.

Zhang et al. (1996) Single-stranded DNA ligation by T4 RNA ligase for PCR cloning of 5'-noncoding fragments and coding sequence of a specific gene. Nucleic Acids Res. 24(5): 990-1.

Zhao et al. (1995) Assessment of stress gene mRNAs (HSP-27, 60 and 70) in obstructed rabbit urinary bladder using a semi-quantitative RT-PCR method. Mol Cell Biochem. (1): 1-7.

Zhenodarova et al. (1989) [Substrate specificity of T4 RNA-ligase. The effect of the nucleotide composition of substrates and the size of phosphate donor on the effectiveness of intermolecular ligation]. Bioorg Khim. 15(4): 478-83.

Zhu et al. (1994) Purification and characterization of PRD1 DNA polymerase. Biochimica Biophysica Acta. 1219(2): 267-276.

Zhu et al. (2001) Global Analysis of Protein Activities Using Proteome Chips. Science 293: 2101-2105.

Zijderveld et al. (1994) Helix-Destabilizing Properties of the Adenovirus DNA-Binding Protein. J. Virol. 68(2): 1158-1164.

Zirvi et al. (1999) Improved fidelity of thermostable ligases for detection of microsatellite repeat sequences using nucleoside analogs. Nucleic Acids Res. 27(24): e41.

Zirvi et al. (1999) Ligase-based detection of mononucleotide repeat sequences. Nucleic Acids Res. 27(24) :e40.

Zuckermann et al. (1987) Efficient methods for attachment of thiol specific probes to the 3'-ends of synthetic oligodeoxyribonucleotides. Nucleic Acids Res. 15(13): 5305-21.

Issue Notification issued May 14, 2003 for U.S. Appl. No. 09/803,713, filed Mar. 9, 2001 (Inventors—Alsmadi et al.).

Notice of Allowance issued Feb. 4, 2003 for U.S. Appl. No. 09/803,713, filed Mar. 9, 2001 (Inventors—Alsmadi et al.).

Supplemental Amendment filed Jan. 23, 2003 for U.S. Appl. No. 09/803,713, filed Mar. 9, 2001 (Inventors—Alsmadi et al.).

Response after Non-Final Action filed Nov. 5, 2002 for U.S. Appl. No. 09/803,713, filed Mar. 9, 2001 (Inventors—Alsmadi et al.).

Non-Final Rejection issued Jun. 5, 2002 for U.S. Appl. No. 09/803,713, filed Mar. 9, 2001 (Inventors—Alsmadi et al.).

Response to Election / Restriction filed Mar. 21, 2002 for U.S. Appl. No. 09/803,713, filed Mar. 9, 2001 (Inventors—Alsmadi et al.).

Restriction Requirement issued Feb. 21, 2002 for U.S. Appl. No. 09/803,713, filed Mar. 9, 2001 (Inventors—Alsmadi et al.).

Notice of Abandonment issued Mar. 8, 2007 for U.S. Appl. No. 10/325,490, filed Dec. 19, 2002 (Alsmadi et al.).

Non-Final Rejection issued Aug. 9, 2006 for U.S. Appl. No. 10/325,490, filed Dec. 19, 2002 (Alsmadi et al.).

Response after Non-Final Action filed May 22, 2006 for U.S. Appl. No. 10/325,490, filed Dec. 19, 2002 (Alsmadi et al.).

Non-Final Rejection issued Jan. 24, 2006 for U.S. Appl. No. 10/325,490, filed Dec. 19, 2002 (Alsmadi et al.).

Response to Election / Restriction filed Oct. 19, 2005 for U.S. Appl. No. 10/325,490, filed Dec. 19, 2002 (Alsmadi et al.).

Restriction Requirement issued Sep. 16, 2005 for U.S. Appl. No. 10/325,490, filed Dec. 19, 2002 (Alsmadi et al.).

Notice of Abandonment issued Nov. 27, 2006 for U.S. Appl. No. 10/404,944, filed Mar. 31, 2003 (Alsmadi et al.).

Non-Final Rejection issued May 9, 2006 for U.S. Appl. No. 10/404,944, filed Mar. 31, 2003 (Alsmadi et al.).

Response after Non-Final Action filed Mar. 2, 2006 for U.S. Appl. No. 10/404,944, filed Mar. 31, 2003 (Alsmadi et al.).

Non-Final Rejection issued Dec. 5, 2005 for U.S. Appl. No. 10/404,944, filed Mar. 31, 2003 (Alsmadi et al.).

Preliminary Amendment filed Mar. 31, 2003 for U.S. Appl. No. 10/404,944, filed Mar. 31, 2003 (Alsmadi et al.).

Issue Notification issued Mar. 21, 2002 for U.S. Appl. No. 09/547,757, filed Apr. 12, 2000 (Faruqi).

Notice of Allowance issued Aug. 31, 2001 for U.S. Appl. No. 09/547,757, filed Apr. 12, 2000 (Faruqi).

Issue Notification issued Feb. 20, 2003 for U.S. Appl. No. 09/597,836, filed Jun. 20, 2000 (Kingsmore et al.).

Notice of Allowance issued Nov. 17, 2002 for U.S. Appl. No. 09/597,836, filed Jun. 20, 2000 (Kingsmore et al.).

Response to Office Action filed Sep. 18, 2002 for U.S. Appl. No. 09/597,836, filed Jun. 20, 2000 (Kingsmore et al.).

Final Rejection issued Mar. 19, 2002 for U.S. Appl. No. 09/597,836, filed Jun. 20, 2000 (Kingsmore et al.).

Response after Non-Final Action issued Feb. 5, 2002 for U.S. Appl. No. 09/597,836, filed Jun. 20, 2000 (Kingsmore et al.).

Non-Final Rejection issued Nov. 5, 2001 for U.S. Appl. No. 09/597,836, filed Jun. 20, 2000 (Kingsmore et al.).

Response after Non-Final Action filed Sep. 20, 2001 for U.S. Appl. No. 09/597,836, filed on Jun. 20, 2000 (Kingsmore et al.).

Non-Final Rejection issued Mar. 20, 2001 for U.S. Appl. No. 09/597,836, filed Jun. 20, 2000 (Kingsmore et al.).

Response filed Oct. 23, 2000 for U.S. Appl. No. 09/597,836, filed Jun. 20, 2000 (Kingsmore et al.).

Certificate of Correction issued Sep. 27, 2005 for U.S. Appl. No. 10/341,287, filed Jan. 13, 2003 (Kingsmore et al.).

Request for Certificate of Correction filed Aug. 23, 2005 for U.S. Appl. No. 10/341,287, filed Jan. 13, 2003 (Kingsmore et al.).

Issue Notification issued Jul. 6, 2005 for U.S. Appl. No. 10/341,287, filed Jan. 13, 2003 (Kingsmore et al.).

Notice of Allowance issued Mar. 15, 2005 for U.S. Appl. No. 10/341,287, filed Jan. 13, 2003 (Kingsmore et al.).

Response after Non-Final Action filed Jan. 4, 2005 for U.S. Appl. No. 10/341,287, filed Jan. 13, 2003 (Kingsmore et al.).

Non-Final Rejection issued Oct. 22, 2004 for U.S. Appl. No. 10/341,287, filed Jan. 13, 2003 (Kingsmore et al.).

Preliminary Amendment filed Jan. 13, 2003 for U.S. Appl. No. 10/341,287, filed Jan. 13, 2003 (Kingsmore et al.).

Notice of Abandonment issued Jun. 10, 2009 for U.S. Appl. No. 11/187,537, filed Jul. 22, 2005 (Kingsmore et al.).

Requirement for Restriction / Election issued Oct. 6, 2008 for U.S. Appl. No. 11/187,537, filed Jul. 22, 2005 (Kingsmore et al.).

Issue Notification issued Jan. 15, 2004 for U.S. Appl. No. 09/897,259, filed Jul. 2, 2001 (Ward et al.).

Notice of Allowance issued Jul. 1, 2003 for U.S. Appl. No. 09/897,259, filed Jul. 2, 2001 (Ward et al.).

Response after Non-Final Rejection filed Apr. 11, 2003 for U.S. Appl. No. 09/897,259, filed Jul. 2, 2001 (Ward et al.).

Non-Final Rejection issued Jan. 17, 2003 for U.S. Appl. No. 09/897,259, filed Jul. 2, 2001 (Ward et al.).

Response to Election / Restriction filed Oct. 30, 2002 for U.S. Appl. No. 09/897,259, filed Jul. 2, 2001 (Ward et al.).

Restriction Requirement issued Sep. 30, 2002 for U.S. Appl. No. 09/897,259, filed Jul. 2, 2001 (Ward et al.).

Notice of Abandonment issued Nov. 14, 2007 for U.S. Appl. No. 09/910,383, filed Jul. 20, 2001 (Nallur et al.).

Advisory Action issued May 1, 2007 for U.S. Appl. No. 09/910,383, filed Jul. 20, 2001 (Nallur et al.).

Amendment/Argument after Notice of Appeal filed Apr. 18, 2007 for U.S. Appl. No. 09/910,383, filed Jul. 20, 2001 (Nallur et al.).

Notice of Appeal issued Apr. 18, 2007 for U.S. Appl. No. 09/910,383, filed Jul. 20, 2001 (Nallur et al.).

Examiner Interview Summary issued Apr. 9, 2007 for U.S. Appl. No. 09/910,383, filed Jul. 20, 2001 (Nallur et al.).

Final Rejection issued Dec. 13, 2006 for U.S. Appl. No. 09/910,383, filed Jul. 20, 2001 (Nallur et al.).

Response after Non-Final Action filed Sep. 29, 2006 for U.S. Appl. No. 09/910,383, filed Jul. 20, 2001 (Nallur et al.).

Non-Final Rejection issued Jun. 15, 2006 for U.S. Appl. No. 09/910,383, filed Jul. 20, 2001 (Nallur et al.).

Communication withdrawing Notice of Non-Compliant Amendment issued Apr. 7, 2006 for U.S. Appl. No. 09/910,383, filed Jul. 20, 2001 (Nallur et al.).

Response after Non-Final Action filed Mar. 22, 2006 for U.S. Appl. No. 09/910,383, filed Jul. 20, 2001 (Nallur et al.).

Advisory Action issued Dec. 13, 2005 for U.S. Appl. No. 09/910,383, filed Jul. 20, 2001 (Nallur et al.).

Amendment after Final Rejection filed Nov. 23, 2005 for U.S. Appl. No. 09/910,383, filed Jul. 20, 2001 (Nallur et al.).

Examiner Interview Summary Record issued Oct. 12, 2005 for U.S. Appl. No. 09/910,383, filed Jul. 20, 2001 (Nallur et al.).

Advisory Action issued Sep. 14, 2005 for U.S. Appl. No. 09/910,383, filed Jul. 20, 2001 (Nallur et al.).

Amendment after Final Rejection filed Aug. 26, 2005 for U.S. Appl. No. 09/910,383, filed Jul. 20, 2001 (Nallur et al.).

Final Rejection issued May 23, 2005 for U.S. Appl. No. 09/910,383, filed Jul. 20, 2001 (Nallur et al.).

Response after Non-Final Action filed Mar. 10, 2005 for U.S. Appl. No. 09/910,383, filed Jul. 20, 2001 (Nallur et al.).

Non-Final Rejection issued Jan. 27, 2005 for U.S. Appl. No. 09/910,383, filed Jul. 20, 2001 (Nallur et al.).

Response after Non-Final Action filed Nov. 19, 2004 for U.S. Appl. No. 09/910,383, filed Jul. 20, 2001 (Nallur et al.).

Non-Final Rejection issued Jun. 23, 2004 for U.S. Appl. No. 09/910,383, filed Jul. 20, 2001 (Nallur et al.).
Issue Notification issued Nov. 30, 2005 for U.S. Appl. No. 09/977,868, filed Oct. 15, 2001 (Dean et al.).
Notice of Allowance issued Feb. 22, 2005 for U.S. Appl. No. 09/977,868, filed Oct. 15, 2001 (Dean et al.).
Response after Non-Final Action filed Jan. 4, 2005 for U.S. Appl. No. 09/977,868, filed Oct. 15, 2001 (Dean et al.).
Non-Final Rejection issued Sep. 9, 2004 for U.S. Appl. No. 09/977,868, filed Oct. 15, 2001 (Dean et al.).
Petition for Withdrawal of Holding of Abandonment filed Feb. 13, 2004 for U.S. Appl. No. 09/977,868, filed Oct. 15, 2001 (Dean et al.).
Preliminary Amendment filed Mar. 29, 2002 for U.S. Appl. No. 09/977,868, filed Oct. 15, 2001 (Dean et al.).
Issue Notification issued Aug. 21, 2003 for U.S. Appl. No. 09/982,212, filed Oct. 18, 2001 (Dean et al.).
Notice of Allowance issued May 20, 2003 for U.S. Appl. No. 09/982,212, filed Oct. 18, 2001 (Dean et al.).
Response after Non-Final Action filed May 7, 2003 for U.S. Appl. No. 09/982,212, filed Oct. 18, 2001 (Dean et al.).
Non-Final Rejection issued Apr. 18, 2003 for U.S. Appl. No. 09/982,212, filed Oct. 18, 2001 (Dean et al.).
Second Preliminary Amendment filed Oct. 25, 2001 for U.S. Appl. No. 09/982,212, filed Oct. 18, 2001 (Dean et al.).
Preliminary Amendment filed Oct. 18, 2001 for U.S. Appl. No. 09/982,212, filed Oct. 18, 2001 (Dean et al.).
Issue Notification issued Jun. 21, 2006 for U.S. Appl. No. 10/272,465, filed Oct. 15, 2002 (Dean et al.).
Decision on Petition to Revive issued May 22, 2006 for U.S. Appl. No. 10/272,465, filed Oct. 15, 2002 (Dean et al.).
Petition to Revive Application filed Mar. 14, 2006 for U.S. Appl. No. 10/272,465, filed Oct. 15, 2002 (Dean et al.).
Notice of Allowance issued Dec. 13, 2005 for U.S. Appl. No. 10/272,465, filed Oct. 15, 2002 (Dean et al.).
Response after Non-Final Action filed Sep. 2, 2005 for U.S. Appl. No. 10/272,465, filed Oct. 15, 2002 (Dean et al.).
Non-Final Rejection issued Aug. 5, 2005 for U.S. Appl. No. 10/272,465, filed Oct. 15, 2002 (Dean et al.).
Issue Notification issued Oct. 31, 2007 for U.S. Appl. No. 10/429,229, filed May 2, 2003 (Bornarth et al.).
Supplemental Notice of Allowance issued Jul. 31, 2007 for U.S. Appl. No. 10/429,229, filed May 2, 2003 (Bornarth et al.).
Notice of Allowance issued Jun. 18, 2007 for U.S. Appl. No. 10/429,229, filed May 2, 2003 (Bornarth et al.).
Examiner Interview Summary issued Jun. 18, 2007 for U.S. Appl. No. 10/429,229, filed May 2, 2003 (Bornarth et al.).
Amendment after Final Rejection filed Jun. 5, 2007 for U.S. Appl. No. 10/429,229, filed May 2, 2003 (Bornarth et al.).
Final Rejection issued Feb. 28, 2007 for U.S. Appl. No. 10/429,229, filed May 2, 2003 (Bornarth et al.).
Response after Non-Final Action filed Dec. 14, 2006 for U.S. Appl. No. 10/429,229, filed May 2, 2003 (Bornarth et al.).
Non-Final Rejection issued Jun. 20, 2006 for U.S. Appl. No. 10/429,229, filed May 2, 2003 (Bornarth et al.).
Response to Election / Restriction filed Apr. 17, 2006 for U.S. Appl. No. 10/429,229, filed May 2, 2003 (Bornarth et al.).
Restriction Requirement issued Feb. 16, 2006 for U.S. Appl. No. 10/429,229, filed May 2, 2003 (Bornarth et al.).
Notice of Abandonment issued May 25, 2010 for U.S. Appl. No. 11/871,707, filed Oct. 12, 2007 (Bornarth et al.).
Final Rejection issued Oct. 29, 2009 for U.S. Appl. No. 11/871,707, filed Oct. 12, 2007 (Bornarth et al.).
Response after Non-Final Rejection filed Jun. 22, 2009 for U.S. Appl. No. 11/871,707, filed Oct. 12, 2007 (Bornarth et al.).
Non-Final Rejection issued Jan. 28, 2009 for U.S. Appl. No. 11/871,707, filed Oct. 12, 2007 (Bornarth et al.).
Preliminary Amendment filed Jan. 31, 2008 for U.S. Appl. No. 11/871,707, filed Oct. 12, 2007 (Bornarth et al.).
Issue Notification issued Oct. 20, 2000 for U.S. Appl. No. 08/754,681, filed Nov. 21, 1996 (Lizardi et al.).
Notice of Allowance issued Mar. 28, 2000 for U.S. Appl. No. 08/754,681, filed Nov. 21, 1996 (Lizardi et al.).
Notice of Appeal filed Feb. 4, 2000 for U.S. Appl. No. 08/754,681, filed Nov. 21, 1996 (Lizardi et al.).
Amendment after Final Rejection filed Dec. 28, 1999 for U.S. Appl. No. 08/754,681, filed Nov. 21, 1996 (Lizardi et al.).
Final Rejection issued Aug. 4, 1999 for U.S. Appl. No. 08/754,681, filed Nov. 21, 1996 (Lizardi et al.).
Supplemental Response filed Apr. 12, 1999 for U.S. Appl. No. 08/754,681, filed Nov. 21, 1996 (Lizardi et al.).
Response after Non-Final Action filed Apr. 1, 1999 for U.S. Appl. No. 08/754,681, filed Nov. 21, 1996 (Lizardi et al.).
Non-Final Rejection issued Oct. 1, 1998 for U.S. Appl. No. 08/754,681, filed Nov. 21, 1996 (Lizardi et al.).
Response after Non-Final Action filed Jul. 6, 1998 for U.S. Appl. No. 08/754,681, filed Nov. 21, 1996 (Lizardi et al.).
Non-Final Rejection issued Jan. 6, 1998 for U.S. Appl. No. 08/754,681, filed Nov. 21, 1996 (Lizardi et al.).
Response after Non-Final Action filed Oct. 21, 1997 for U.S. Appl. No. 08/754,681, filed Nov. 21, 1996 (Lizardi et al.).
Restriction Requirement issued Jun. 17, 1997 for U.S. Appl. No. 08/754,681, filed Nov. 21, 1996 (Lizardi et al.).
Issue Notification issued Nov. 21, 2001 for U.S. Appl. No. 09/602,428, filed Jun. 23, 2000 (Lizardi et al.).
Notice of Allowance issued Jun. 28, 2001 for U.S. Appl. No. 09/602,428, filed Jun. 23, 2000 (Lizardi et al.).
Response after Non-Final Action filed Apr. 9, 2001 for U.S. Appl. No. 09/602,428, filed Jun. 23, 2000 (Lizardi et al.).
Non-Final Rejection issued Nov. 22, 2000 for U.S. Appl. No. 09/602,428, filed Jun. 23, 2000 (Lizardi et al.).
Preliminary Amendment filed Jun. 23, 2000 for U.S. Appl. No. 09/602,428, filed Jun. 23, 2000 (Lizardi et al.).
Issue Notification issued Sep. 25, 2003 for U.S. Appl. No. 09/841,513, filed Apr. 24, 2001 (Lizardi).
Notice of Allowance issued Jan. 16, 2003 for U.S. Appl. No. 09/841,513, filed Apr. 24, 2001 (Lizardi).
Response after Non-Final Action filed Oct. 18, 2002 for U.S. Appl. No. 09/841,513, filed Apr. 24, 2001 (Lizardi).
Non-Final Rejection issued Apr. 30, 2002 for U.S. Appl. No. 09/841,513, filed Apr. 24, 2001 (Lizardi).
Preliminary Amendment filed Apr. 24, 2001 for U.S. Appl. No. 09/841,513, filed Apr. 24, 2001 (Lizardi).
Notice of Abandonment issued Apr. 5, 2006 for U.S. Appl. No. 10/413,041, filed Apr. 10, 2003 (Lizardi et al.).
Restriction Requirement issued Sep. 22, 2005 for U.S. Appl. No. 10/413,041, filed Apr. 10, 2003 (Lizard et al.).
Decision on Petition issued Jul. 3, 2003 for U.S. Appl. No. 10/413,041, filed Apr. 10, 2003 (Lizard et al.).
Petition to Correct Filing Date filed May 8, 2003 for U.S. Appl. No. 10/413,041, filed Apr. 10, 2003 (Lizard et al.).
Preliminary Amendment filed Apr. 10, 2003 for U.S. Appl. No. 10/413,041, filed Apr. 10, 2003 (Lizardi et al.).
Issue Notification issued Jun. 10, 2009 for U.S. Appl. No. 10/072,666, filed Feb. 8, 2002 (Kumar et al.).
Notice of Allowance issued Jan. 27, 2009 for U.S. Appl. No. 10/072,666, filed Feb. 8, 2002 (Kumar et al.).
Notice of Allowance issued Sep. 26, 2008 for U.S. Appl. No. 10/072,666, filed Feb. 8, 2002 (Kumar et al.).
Amendment after Final Rejection filed Sep. 10, 2008 for U.S. Appl. No. 10/072,666, filed Feb. 8, 2002 (Kumar et al.).
Final Rejection issued Jul. 15, 2008 for U.S. Appl. No. 10/072,666, filed Feb. 8, 2002 (Kumar et al.).
Response to Non-Final Action filed Apr. 30, 2008 for U.S. Appl. No. 10/072,666, filed Feb. 8, 2002 (Kumar et al.).
Non-Final Rejection issued Feb. 1, 2008 for U.S. Appl. No. 10/072,666, filed Feb. 8, 2002 (Kumar et al.).
Response after Non-Final Action filed Nov. 15, 2007 for U.S. Appl. No. 10/072,666, filed Feb. 8, 2002 (Kumar et al.).
Non-Final Rejection issued Jul. 9, 2007 for U.S. Appl. No. 10/072,666, filed Feb. 8, 2002 (Kumar et al.).
Response after Non-Final Action filed Apr. 24, 2007 for U.S. Appl. No. 10/072,666, filed Feb. 8, 2002 (Kumar et al.).
Non-Final Rejection issued Jan. 24, 2007 for U.S. Appl. No. 10/072,666, filed Feb. 8, 2002 (Kumar et al.).

Response to Office Action filed Nov. 30, 2006 for U.S. Appl. No. 10/072,666, filed Feb. 8, 2002 (Kumar et al.).
Advisory Action issued Nov. 8, 2006 for U.S. Appl. No. 10/072, 666, filed Feb. 8, 2002 (Kumar et al.).
Amendment after Final Rejection filed Oct. 20, 2006 for U.S. Appl. No. 10/072,666, filed Feb. 8, 2002 (Kumar et al.).
Final Rejection issued Jul. 31, 2006 for U.S. Appl. No. 10/072,666, filed Feb. 8, 2002 (Kumar et al.).
Response after Non-Final Action issued May 12, 2006 for U.S. Appl. No. 10/072,666, filed Feb. 8, 2002 (Kumar et al.).
Non-Final Rejection issued Jan. 27, 2006 for U.S. Appl. No. 10/072,666, filed Feb. 8, 2002 (Kumar et al.).
Response to Office Action issued Nov. 11, 2005 for U.S. Appl. No. 10/072,666, filed Feb. 8, 2002 (Kumar et al.).
Final Rejection issued Jul. 11, 2005 for U.S. Appl. No. 10/072,666, filed Feb. 8, 2002 (Kumar et al.).
Response after Non-Final Action filed Apr. 25, 2005 for U.S. Appl. No. 10/072,666, filed Feb. 8, 2002 (Kumar et al.).
Non-Final Rejection issued Feb. 10, 2005 for U.S. Appl. No. 10/072,666, filed Feb. 8, 2002 (Kumar et al.).
Response after Non-Final Action filed Aug. 4, 2004 for U.S. Appl. No. 10/072,666, filed Feb. 8, 2002 (Kumar et al.).
Non-Final Rejection issued Apr. 19, 2004 for U.S. Appl. No. 10/072,666, filed Feb. 8, 2002 (Kumar et al.).
Response after Non-Final Action filed Nov. 10, 2003 for U.S. Appl. No. 10/072,666, filed Feb. 8, 2002 (Kumar et al.).
Non-Final Rejection issued May 8, 2003 for U.S. Appl. No. 10/072,666, filed Feb. 8, 2002 (Kumar et al.).
Issue Notification issued Nov. 25, 2004 for U.S. Appl. No. 09/460,078, filed Dec. 14, 1999 (Hafner et al.).
Notice of Allowance issued Jul. 14, 2004 for U.S. Appl. No. 09/460,078, filed Dec. 14, 1999 (Hafner et al.).
Amendment after Final Rejection filed Jun. 14, 2004 for U.S. Appl. No. 09/460,078, filed Dec. 14,,1999 (Hafner et al.).
Examiner Interview Summary issued May 25, 2004 for U.S. Appl. No. 09/460,078, filed Dec. 14, 1999 (Hafner et al.).
Final Rejection issued Feb. 13, 2004 for U.S. Appl. No. 09/460,078, filed Dec. 14, 1999 (Hafner et al.).
Response after Non-Final Action filed Nov. 19, 2003 for U.S. Appl. No. 09/460,078, filed Dec. 14, 1999 (Hafner et al.).
Non-Final Rejection issued May 19, 2003 for U.S. Appl. No. 09/460,078, filed Dec. 14, 1999 (Hafner et al.).
Response after Non-Final Action filed Jan. 14, 2003 for U.S. Appl. No. 09/460,078, filed Dec. 14, 1999 (Hafner et al.).
Non-Final Rejection issued Sep. 4, 2002 for U.S. Appl. No. 09/460,078, filed Dec. 14, 1999 (Hafner et al.).
Amendment and Response filed Jun. 17, 2002 for U.S. Appl. No. 09/460,078, filed Dec. 14, 1999 (Hafner et al.).
Notice of Appeal filed Jan. 17, 2002 for U.S. Appl. No. 09/460,078, filed Dec. 14, 1999 (Hafner et al.).
Final Rejection issued Jul. 17, 2001 for U.S. Appl. No. 09/460,078, filed Dec. 14, 1999 (Hafner et al.).
Response after Non-Final Action filed May 21, 2001 for U.S. Appl. No. 09/460,078, filed Dec. 14, 1999 (Hafner et al.).
Non-Final Rejection issued Nov. 20, 2000 for U.S. Appl. No. 09/460,078, filed Dec. 14, 1999 (Hafner et al.).
Response to Election / Restriction filed Mar. 29, 2000 for U.S. Appl. No. 09/460,078, filed Dec. 14, 1999 (Hafner et al.).
Restriction Requirement issued Jun. 30, 2000 for U.S. Appl. No. 09/460,078, filed Dec. 14, 1999 (Hafner et al.).
Issue Notification issued Mar. 26, 2008 for U.S. Appl. No. 10/917,580, filed Aug. 13, 2004 (Hafner et al.).
Notice of Allowance issued Nov. 30, 2007 for U.S. Appl. No. 10/917,580, filed Aug. 13, 2004 (Hafner et al.).
Response after Non-Final Action filed Oct. 1, 2007 for U.S. Appl. No. 10/917,580, filed Aug. 13, 2004 (Hafner et al.).
Non-Final Rejection issued Jun. 25, 2007 for U.S. Appl. No. 10/917,580, filed Aug. 13, 2004 (Hafner et al.).
Response to Election / Restriction filed May 10, 2007 for U.S. Appl. No. 10/917,580, filed Aug. 13, 2004 (Hafner et al.).
Restriction Requirement issued Jan. 11, 2007 for U.S. Appl. No. 10/917,580, filed Aug. 13, 2004 (Hafner et al.).
Second Preliminary Amendment filed Nov. 15, 2004 for U.S. Appl. No. 10/917,580, filed Aug. 13, 2004 (Hafner et al.).
Preliminary Amendment filed Aug. 13, 2004 for U.S. Appl. No. 10/917,580, filed Aug. 13, 2004 (Hafner et al.).
Notice of Abandonment issued Nov. 13, 2008 for U.S. Appl. No. 10/325,665, filed Dec. 19, 2002 (Alsmadi et al.).
Non-Final Rejection issued Apr. 17, 2008 for U.S. Appl. No. 10/325,665, filed Dec. 19, 2002 (Alsmadi et al.).
Non-Final Rejection issued Oct. 25, 2007 for U.S. Appl. No. 10/325,665, filed Dec. 19, 2002 (Alsmadi et al.).
Amendment/Argument with Notice of Appeal filed Sep. 25, 2007 for U.S. Appl. No. 10/325,665, filed Dec. 19, 2002 (Alsmadi et al.).
Final Rejection issued Mar. 26, 2007 for U.S. Appl. No. 10/325,665, filed Dec. 19, 2002 (Alsmadi et al.).
Response after Non-Final Action filed Dec. 22, 2006 for U.S. Appl. No. 10/325,665, filed Dec. 19, 2002 (Alsmadi et al.).
Non-Final Rejection issued Aug. 3, 2006 for U.S. Appl. No. 10/325,665, filed Dec. 19, 2002 (Alsmadi et al.).
Response after Non-Final Action filed Apr. 13, 2006 for U.S. Appl. No. 10/325,665, filed Dec. 19, 2002 (Alsmadi et al.).
Non-Final Rejection issued Dec. 30, 2005 for U.S. Appl. No. 10/325,665, filed Dec. 19, 2002 (Alsmadi et al.).
Response to Election / Restriction filed Sep. 21, 2005 for U.S. Appl. No. 10/325,665, filed Dec. 19, 2002 (Alsmadi et al.).
Restriction Requirement issued Apr. 21, 2005 for U.S. Appl. No. 10/325,665, filed Dec. 19, 2002 (Alsmadi et al.).
Issue Notification issued Nov. 30, 2005 for U.S. Appl. No. 10/335,573, filed Dec. 31, 2002 (Kumar et al.).
Notice of Allowance issued Mar. 29, 2005 for U.S. Appl. No. 10/335,573, filed Dec. 31, 2002 (Kumar et al.).
Response after Non-Final Action filed Dec. 1, 2004 for U.S. Appl. No. 10/335,573, filed Dec. 31, 2002 (Kumar et al.).
Non-Final Rejection issued Jul. 29, 2004 for U.S. Appl. No. 10/335,573, filed Dec. 31, 2002 (Kumar et al.).
Notice of Abandonment issued May 12, 2008 for U.S. Appl. No. 11/201,339, filed Aug. 10, 2005 (Kumar et al.).
Restriction Requirement issued Sep. 25, 2007 for U.S. Appl. No. 11/201,339, filed Aug. 10, 2005 (Kumar et al.).
Preliminary Amendment filed Aug. 10, 2005 for U.S. Appl. No. 11/201,339, filed Aug. 10, 2005 (Kumar et al.).
Response to Final Rejection filed May 26, 2010 for U.S. Appl. No. 10/327,602, filed Dec. 20, 2002 (Lasken).
Notice of Appeal issued Apr. 27, 2010 for U.S. Appl. No. 10/327,602, filed Dec. 20, 2002 (Lasken).
Interview Summary issued Dec. 24, 2009 for U.S. Appl. No. 10/327,602, filed Dec. 20, 2002 (Lasken).
Supplemental Non-Final Rejection issued Oct. 27, 2009 for U.S. Appl. No. 10/327,602, filed Dec. 20, 2002 (Lasken).
Non-Final Rejection issued Oct. 15, 2009 for U.S. Appl. No. 10/327,602, filed Dec. 20, 2002 (Lasken).
Amendment and Response to Final Office Action filed Sep. 10, 2009 for U.S. Appl. No. 10/327,602, filed Dec. 20, 2002 (Lasken).
Final Rejection issued Jun. 10, 2009 for U.S. Appl. No. 10/327,602, filed Dec. 20, 2002 (Lasken).
Amendment and Response filed Mar. 31, 2009 for U.S. Appl. No. 10/327,602, filed Dec. 20, 2002 (Lasken).
Non-Final Rejection issued Jan. 6, 2009 for U.S. Appl. No. 10/327,602, filed Dec. 20, 2002 (Lasken).
Response after Final Rejection filed Dec. 11, 2008 for U.S. Appl. No. 10/327,602, filed Dec. 20, 2002 (Lasken).
Advisory Action issued Nov. 26, 2008 for U.S. Appl. No. 10/327,602, filed Dec. 20, 2002 (Lasken).
Amendment after Final Rejection filed Nov. 10, 2008 for U.S. Appl. No. 10/327,602, filed Dec. 20, 2002 (Lasken).
Final Rejection issued Aug. 12, 2008 for U.S. Appl. No. 10/327,602, filed Dec. 20, 2002 (Lasken).
Response after Final Rejection filed May 15, 2008 for U.S. Appl. No. 10/327,602, filed Dec. 20, 2002 (Lasken).
Non-Final Rejection issued Jan. 17, 2008 for U.S. Appl. No. 10/327,602, filed Dec. 20, 2002 (Lasken).
Amendment after Final Rejection filed Oct. 25, 2007 for U.S. Appl. No. 10/327,602, filed Dec. 20, 2002 (Lasken).

Advisory Action issued Oct. 16, 2007 for U.S. Appl. No. 10/327,602, filed Dec. 20, 2002 (Lasken).
Amendment after Final filed Oct. 1, 2007 for U.S. Appl. No. 10/327,602, filed Dec. 20, 2002 (Lasken).
Final Rejection issued May 23, 2007 for U.S. Appl. No. 10/327,602, filed Dec. 20, 2002 (Lasken).
Response after Non-Final Rejection filed Mar. 15, 2007 for U.S. Appl. No. 10/327,602, filed Dec. 20, 2002 (Lasken).
Non-Final Rejection issued Nov. 14, 2006 for U.S. Appl. No. 10/327,602, filed Dec. 20, 2002 (Lasken).
Response after Non-Final Rejection filed Aug. 24, 2006 for U.S. Appl. No. 10/327,602, filed Dec. 20, 2002 (Lasken).
Restriction Requirement issued Jun. 26, 2006 for U.S. Appl. No. 10/32,602, filed Dec. 20, 2002 (Lasken).
Notice of Allowance issued Jun. 13, 2011 for U.S. Appl. No. 10/405,822, filed Mar. 31, 2003 (Abarzua et al.).
Notice of Allowance issued Feb. 4, 2011 for U.S. Appl. No. 10/405,822, filed Mar. 31, 2003 (Abarzua et al.).
Examiner Interview Summary issued Jan. 25, 2011 for U.S. Appl. No. 10/405,822, filed Mar. 31, 2003 (Abarzua et al.).
Response to Final Rejection filed Jan. 13, 2011 for U.S. Appl. No. 10/405,822, filed Mar. 31, 2003 (Abarzua et al.).
Final Rejection issued Dec. 8, 2010 for U.S. Appl. No. 10/405,822, filed Mar. 31, 2003 (Abarzua et al.).
Response to Final Rejection filed Sep. 3, 2010 for U.S. Appl. No. 10/405,822, filed Mar. 31, 2003 (Abarzua et al.).
Examiner Interview Summary issued Aug. 18, 2010 for U.S. Appl. No. 10/405,822, filed Mar. 31, 2003 (Abarzua et al.).
Final Rejection issued Mar. 4, 2010 for U.S. Appl. No. 10/40,822, filed Mar. 31, 2003 (Abarzua et al.).
Response after Non-Final Rejection filed Nov. 25, 2009 for U.S. Appl. No. 10/405,822, filed Mar. 31, 2003 (Abarzua et al.).
Non-Final Rejection issued Jun. 1, 2009 for U.S. Appl. No. 10/405,822, filed Mar. 31, 2003 (Abarzua et al.).
Response after Final Rejection filed Mar. 11, 2009 for U.S. Appl. No. 10/405,822, filed Mar. 31, 2003 (Abarzua et al.).
Advisory Action issued Feb. 27, 2009 for U.S. Appl. No. 10/405,822, filed Mar. 31, 2003 (Abarzua et al.).
Response after Final Rejection filed Feb. 11, 2009 for U.S. Appl. No. 10/405,822, filed Mar. 31, 2003 (Abarzua et al.).
Examiner Interview Summary issued Dec. 15, 2008 for U.S. Appl. No. 10/405,822, filed Mar. 31, 2003 (Abarzua et al.).
Final Rejection issued Sep. 11, 2008 for U.S. Appl. No. 10/405,822, filed Mar. 31, 2003 (Abarzua et al.).
Response to Non-Final Rejection filed May 30, 2008 for U.S. Appl. No. 10/405,822, filed Mar. 31, 2003 (Abarzua et al.).
Non-Final Rejection issued Mar. 28, 2008 for U.S. Appl. No. 10/405,822, filed Mar. 31, 2003 (Abarzua et al.).
Response after Final Rejection filed Dec. 28, 2007 for U.S. Appl. No. 10/405,822, filed Mar. 31, 2003 (Abarzua et al.).
Advisory Action issued Nov. 9, 2007 for U.S. Appl. No. 10/405,822, filed Mar. 31, 2003 (Abarzua et al.).
Response after Final Rejection with Notice of Appeal filed Oct. 30, 2007 for U.S. Appl. No. 10/405,822, filed Mar. 31, 2003 (Abarzua et al.).
Final Rejection issued Apr. 30, 2007 for U.S. Appl. No. 10/405,822, filed Mar. 31, 2003 (Abarzua et al.).
Response after Non-Final Action filed Jan. 23, 2007 for U.S. Appl. No. 10/405,822, filed Mar. 31, 2003 (Abarzua et al.).
Non-Final Rejection issued Aug. 2, 2006 for U.S. Appl. No. 10/405,822, filed Mar. 31, 2003 (Abarzua et al.).
Response to Election / Restriction filed May 31, 2006 for U.S. Appl. No. 10/405,822, filed Mar. 31, 2003 (Abarzua et al.).
Restriction Requirement issued Dec. 13, 2005 for U.S. Appl. No. 10/405,822, filed Mar. 31, 2003 (Abarzua et al.).
Notice of Abandonment issued Jun. 5, 2009 for U.S. Appl. No. 10/454,946, filed Jun. 4, 2003 (Feaver et al.).
Non-Final Rejection issued Nov. 26, 2008 for U.S. Appl. No. 10/454,946, filed Jun. 4, 2003 (Feaver et al.).
Amendment and Response filed Aug. 29, 2008 for U.S. Appl. No. 10/454,946, filed Jun. 4, 2003 (Feaver et al.).
Examiner Interview Summary issued Aug. 8, 2008 for U.S. Appl. No. 10/454,946, filed Jun. 4, 2003 (Feaver et al.).
Advisory Action issued Mar. 25, 2008 for U.S. Appl. No. 10/454,946, filed Jun. 4, 2003 (Feaver et al.).
Notice of Appeal filed Mar. 17, 2008 for U.S. Appl. No. 10/454,946, filed Jun. 4, 2003 (Feaver et al.).
Amendment after Final filed Feb. 8, 2008 for U.S. Appl. No. 10/454,946, filed Jun. 4, 2003 (Feaver et al.).
Examiner Interview Summary issued Jan. 29, 2008 for U.S. Appl. No. 10/454,946, filed Jun. 4, 2003 (Feaver et al.).
Final Rejection issued Sep. 18, 2007 for U.S. Appl. No. 10/454,946, filed Jun. 4, 2003 (Feaver et al.).
Response after Non-Final Action filed Jul. 5, 2007 for U.S. Appl. No. 10/454,946, filed Jun. 4, 2003 (Feaver et al.).
Non-Final Rejection issued Feb. 9, 2007 for U.S. Appl. No. 10/454,946, filed Jun. 4, 2003 (Feaver et al.).
Response after Non-Final Action filed Nov. 16, 2006 for U.S. Appl. No. 10/454,946, filed Jun. 4, 2003 (Feaver et al.).
Non-Final Rejection issued Jul. 26, 2006 for U.S. Appl. No. 10/454,946, filed Jun. 4, 2003 (Feaver et al.).
Response to Election / Restriction filed May 3, 2006 for U.S. Appl. No. 10/454,946, filed Jun. 4, 2003 (Feaver et al.).
Restriction Requirement issued Feb. 6, 2006 for U.S. Appl. No. 10/454,946, filed Jun. 4, 2003 (Feaver et al.).
Issue Notification issued May 18, 2011 for U.S. Appl. No. 10/456,056, filed Jun. 6, 2003 (Kumar et al.).
Notice of Allowance issued Apr. 1, 2011 for U.S. Appl. No. 10/456,056, filed Jun. 6, 2003 (Kumar et al.).
Notice of Allowance issued Jan. 25, 2011 for U.S. Appl. No. 10/456,056, filed Jun. 6, 2003 (Kumar et al.).
Response after Non-Final Action filed Dec. 13, 2010 for U.S. Appl. No. 10/456,056, filed Jun. 6, 2003 (Kumar et al.).
Notice of Non-Compliant Amendment issued Dec. 7, 2010 for U.S. Appl. No. 10/456,056, filed Jun. 6, 2003 (Kumar et al.).
Response to Final Rejection filed Nov. 23, 2010 for U.S. Appl. No. 10/456,056, filed Jun. 6, 2003 (Kumar et al.).
Non-Final Rejection issued Jun. 24, 2010 for U.S. Appl. No. 10/456,056, filed Jun. 6, 2003 (Kumar et al.).
Response after Final Rejection filed Feb. 4, 2010 for U.S. Appl. No. 10/456,056, filed Jun. 6, 2003 (Kumar et al.).
Examiner Interview Summary issued Nov. 17, 2009 for U.S. Appl. No. 10/456,056, filed Jun. 6, 2003 (Kumar et al.).
Final Rejection issued Aug. 4, 2009 for U.S. Appl. No. 10/456,056, filed Jun. 6, 2003 (Kumar et al.).
Response to Final Rejection filed May 27, 2009 for U.S. Appl. No. 10/456,056, filed Jun. 6, 2003 (Kumar et al.).
Final Rejection issued Feb. 12, 2009 for U.S. Appl. No. 10/456,056, filed Jun. 6, 2003 (Kumar et al.).
Response after Non-Final Action filed Oct. 23, 2008 for U.S. Appl. No. 10/456,056, filed Jun. 6, 2003 (Kumar et al.).
Non-Final Rejection issued Aug. 8, 2008 for U.S. Appl. No. 10/456,056, filed Jun. 6, 2003 (Kumar et al.).
Response to Final Rejection filed Apr. 7, 2008 for U.S. Appl. No. 10/456,056, filed Jun. 6, 2003 (Kumar et al.).
Response to Final Rejection filed Mar. 7, 2008 for U.S. Appl. No. 10/456,056, filed Jun. 6, 2003 (Kumar et al.).
Notice of Appeal filed Sep. 6, 2007 for U.S. Appl. No. 10/456,056, filed Jun. 6, 2003 (Kumar et al.).
Examiner Interview Summary issued Apr. 17, 2007 for U.S. Appl. No. 10/456,056, filed Jun. 6, 2003 (Kumar et al.).
Final Rejection issued Mar. 6, 2007 for U.S. Appl. No. 10/456,056, filed Jun. 6, 2003 (Kumar et al.).
Response after Non-Final Action filed Dec. 7, 2006 for U.S. Appl. No. 10/456,056, filed Jun. 6, 2003 (Kumar et al.).
Non-Final Rejection issued Aug. 2, 2006 for U.S. Appl. No. 10/456,056, filed Jun. 6, 2003 (Kumar et al.).
Response to Election / Restriction filed May 12, 2006 for U.S. Appl. No. 10/456,056, filed Jun. 6, 2003 (Kumar et al.).
Requirement for Restriction / Election issued Feb. 23, 2006 for U.S. Appl. No. 10/456,056, filed Jun. 6, 2003 (Kumar et al.).
Issue Notification issued Nov. 9, 2001 for U.S. Appl. No. 09/605,192, filed Jun. 28, 2000 (Lasken et al.).
Response to 312 Amendment issued Aug. 17, 2001 for U.S. Appl. No. 09/605,192, filed Jun. 28, 2000 (Lasken et al.).

Amendment after Notice of Allowance filed Jul. 31, 2001 for U.S. Appl. No. 09/605,192, filed Jun. 28, 2000 (Lasken et al.).
Notice of Allowance issued May 11, 2001 for U.S. Appl. No. 09/605,192, filed Jun. 28, 2000 (Lasken et al.).
Response after Non-Final Action filed Mar. 16, 2001 for U.S. Appl. No. 09/605,192, filed Jun. 28, 2000 (Lasken et al.).
Non-Final Rejection issued Nov. 16, 2000 for U.S. Appl. No. 09/605,192, filed on Jun. 28, 2000 (Lasken et al.).
Notice of Abandonment issued May 27, 2009 for U.S. Appl. No. 09/920,571, filed Jul. 31, 2001 (Lasken et al.).
Final Rejection issued Sep. 15, 2008 for U.S. Appl. No. 09/920,571, filed Jul. 31, 2001 (Lasken et al.).
Response after Non-Final Action filed Jul. 2, 2008 for U.S. Appl. No. 09/920,571, filed Jul. 31, 2001 (Lasken et al.).
Non-Final Rejection issued Mar. 17, 2008 for U.S. Appl. No. 09/920,571, filed Jul. 31, 2001 (Lasken et al.).
Response after Non-Final Action filed Dec. 27, 2007 for U.S. Appl. No. 09/920,571, filed Jul. 31, 2001 (Lasken et al.).
Non-Final Rejection issued Jun. 28, 2007 for U.S. Appl. No. 09/920,571, filed Jul. 31, 2001 (Lasken et al.).
Response to Election/Restriction filed May 7, 2007 for U.S. Appl. No. 09/920,571, filed Jul. 31, 2001 (Lasken et al.).
Restriction Requirement issued Mar. 6, 2007 for U.S. Appl. No. 09/920,571, filed Jul. 31, 2001 (Lasken et al.).
Response to Final Rejection filed Dec. 7, 2006 for U.S. Appl. No. 09/920,571, filed Jul. 31, 2001 (Lasken et al.).
Final Rejection issued Jun. 12, 2006 for U.S. Appl. No. 09/920,571, filed Jul. 31, 2001 (Lasken et al.).
Response after Non-Final Action filed Mar. 27, 2006 for U.S. Appl. No. 09/920,571, filed Jul. 31, 2001 (Lasken et al.).
Non-Final Rejection issued Nov. 1, 2005 for U.S. Appl. No. 09/920,571, filed Jul. 31, 2001 (Lasken et al.).
Response to Final Rejection filed Aug. 15, 2005 for U.S. Appl. No. 09/920,571, filed Jul. 31, 2001 (Lasken et al.).
Advisory Action issued Jun. 20, 2005 for U.S. Appl. No. 09/920,571, filed Jul. 31, 2001 (Lasken et al.).
Response to Final Rejection with Notice of Appeal filed May 31, 2005 for U.S. Appl. No. 09/920,571, filed Jul. 31, 2001 (Lasken et al.).
Final Rejection issued Feb. 14, 2005 for U.S. Appl. No. 09/920,571, filed Jul. 31, 2001 (Lasken et al.).
Response after Non-Final Action filed Nov. 22, 2004 for U.S. Appl. No. 09/92,571, filed Jul. 31, 2001 (Lasken et al.).
Non-Final Rejection issued Aug. 25, 2004 for U.S. Appl. No. 09/920,571, filed Jul. 31, 2001 (Lasken et al.).
Advisory Action issued Jun. 23, 2004 for U.S. Appl. No. 09/920,571, filed Jul. 31, 2001 (Lasken et al.).
Response to Final Rejection with Notice of Appeal filed May 25, 2004 for U.S. Appl. No. 09/920,571, filed Jul. 31, 2001 (Lasken et al.).
Final Rejection issued Feb. 18, 2004 for U.S. Appl. No. 09/920,571, filed Jul. 31, 2001 (Lasken et al.).
Response after Non-Final Action filed Oct. 15, 2003 for U.S. Appl. No. 09/920,571, filed Jul. 31, 2001 (Lasken et al.).
Miscellaneous Communication issued Oct. 7, 2003 for U.S. Appl. No. 09/920,571, filed Jul. 31, 2001 (Lasken et al.).
Response after Non-Final Action filed Jun. 12, 2003 for U.S. Appl. No. 09/920,571, filed Jul. 31, 2001 (Lasken et al.).
Non-Final Rejection issued Dec. 20, 2002 for U.S. Appl. No. 09/920,571, filed Jul. 31, 2001 (Lasken et al.).
Supplemental Response filed Sep. 27, 2002 for U.S. Appl. No. 09/920,571, filed Jul. 31, 2001 (Lasken et al.).
Supplemental Response filed Sep. 16, 2002 for U.S. Appl. No. 09/920,571, filed Jul. 31, 2001 (Lasken et al.).
Notice of Informal or Non-Responsive Amendment issued Aug. 27, 2002 for U.S. Appl. No. 09/920,571, filed Jul. 31, 2001 (Lasken et al.).
Response after Non-Final Action filed Jun. 12, 2002 for U.S. Appl. No. 09/920,571, filed Jul. 31, 2001 (Lasken et al.).
Non-Final Rejection issued Dec. 12, 2001 for U.S. Appl. No. 09/920,571, filed Jul. 31, 2001 (Lasken et al.).
Preliminary Amendment filed Aug. 1, 2001 for U.S. Appl. No. 09/920,571, filed Jul. 31, 2001 (Lasken et al.).

Request for Certificate of Correction filed Aug. 27, 2002 for U.S. Appl. No. 09/577,444, filed May 24, 2000 (Kingsmore et al.).
Issue Notification issued Aug. 30, 2001 for U.S. Appl. No. 09/577,444, filed May 24, 2000 (Kingsmore et al.).
Notice of Allowance issued Mar. 29, 2001 for U.S. Appl. No. 09/577,444, filed May 24, 2000 (Kingsmore et al.).
Decision regarding Certificate of Correction issued Mar. 22, 2004 for U.S. Appl. No. 09/897,665, filed Jul. 2, 2001 (Kingsmore et al.).
Request for Certificate of Correction filed Feb. 25, 2004 for U.S. Appl. No. 09/897,665, filed Jul. 2, 2001 (Kingsmore et al.).
Issue Notification issued Dec. 11, 2003 for U.S. Appl. No. 09/897,665, filed Jul. 2, 2001 (Kingsmore et al.).
Notice of Allowance issued Jul. 30, 2003 for U.S. Appl. No. 09/897,665, filed Jul. 2, 2001 (Kingsmore et al.).
Notice of Appeal filed May 27, 2003 for U.S. Appl. No. 09/897,665, filed Jul. 2, 2001 (Kingsmore et al.).
Response to Final Rejection and Terminal Disclaimer filed May 27, 2003 for U.S. Appl. No. 09/897,665, filed Jul. 2, 2001 (Kingsmore et al.).
Final Rejection issued Feb. 25, 2003 for U.S. Appl. No. 09/897,665, filed Jul. 2, 2001 (Kingsmore et al.).
Response after Non-Final Action filed Dec. 4, 2002 for U.S. Appl. No. 09/897,665, filed Jul. 2, 2001 (Kingsmore et al.).
Non-Final Rejection issued Jul. 19, 2002 for U.S. Appl. No. 09/897,665, filed Jul. 2, 2001 (Kingsmore et al.).
Preliminary Amendment filed Jul. 2, 2001 for U.S. Appl. No. 09/897,665, filed Jul. 2, 2001 (Kingsmore et al.).
Issue Notification issued Oct. 2, 2003 for U.S. Appl. No. 09/910,372, filed Jul. 20, 2001 (Bandaru et al.).
Notice of Allowance issued Apr. 8, 2003 for U.S. Appl. No. 09/910,372, filed Jul. 20, 2001 (Bandaru et al.).
Supplemental Response filed Mar. 20, 2003 for U.S. Appl. No. 09/910,372, filed Jul. 20, 2001 (Bandaru et al.).
Amendment and Response filed Jan. 17, 2003 for U.S. Appl. No. 09/910,372, filed Jul. 20, 2001 (Bandaru et al.).
Non-Final Rejection issued Nov. 13, 2002 for U.S. Appl. No. 09/910,372, filed Jul. 20, 2001 (Bandaru et al.).
Response to Election / Restriction filed Sep. 27, 2002 for U.S. Appl. No. 09/910,372, filed Jul. 20, 2001 (Bandaru et al.).
Restriction Requirement issued Sep. 17, 2002 for U.S. Appl. No. 09/910,372, filed Jul. 20, 2001 (Bandaru et al.).
Issue Notification issued Oct. 14, 2004 for U.S. Appl. No. 10/465,759, filed Jun. 19, 2003 (Bandaru et al.).
Notice of Allowance issued May 4, 2004 for U.S. Appl. No. 10/465,759, filed Jun. 19, 2003 (Bandaru et al.).
Response after Non-Final Action filed Apr. 12, 2004 for U.S. Appl. No. 10/465,759, filed Jun. 19, 2003 (Bandaru et al.).
Non-Final Rejection issued Jan. 8, 2004 for U.S. Appl. No. 10/465,759, filed Jun. 19, 2003 (Bandaru et al.).
Issue Notification issued Dec. 5, 2002 for U.S. Appl. No. 09/723,685, filed Nov. 28, 2000 (Abarzua).
Notice of Allowance issued Apr. 17, 2002 for U.S. Appl. No. 09/723,685, filed Nov. 28, 2000 (Abarzua).
Response after Non-Final Action filed Dec. 10, 2001 for U.S. Appl. No. 09/723,685, filed Nov. 28, 2000 (Abarzua).
Non-Final Rejection issued Aug. 28, 2001 for U.S. Appl. No. 09/723,685, filed Nov. 28, 2000 (Abarzua).
Response after Non-Final Action filed Jun. 13, 2001 for U.S. Appl. No. 09/723,685, filed Nov. 28, 2000 (Abarzua).
Non-Final Rejection issued Mar. 13, 2001 for U.S. Appl. No. 09/723,685, filed Nov. 28, 2000 (Abarzua).
Issue Notification issued Apr. 19, 2006 for U.S. Appl. No. 10/196,539, filed Jul. 16, 2002 (Abarzua).
Notice of Allowance issued Nov. 15, 2005 for U.S. Appl. No. 10/196,539, filed Jul. 16, 2002 (Abarzua).
Response after Non-Final Action with Terminal Disclaimer filed Aug. 10, 2005 for U.S. Appl. No. 10/196,539, filed Jul. 16, 2002 (Abarzua).
Non-Final Rejection issued Mar. 10, 2005 for U.S. Appl. No. 10/196,539, filed Jul. 16, 2002 (Abarzua).
Notice of Abandonment issued Oct. 15, 2008 for U.S. Appl. No. 11/429,549, filed May 5, 2006 (Abarzua).

Non-Final Rejection issued Mar. 26, 2008 for U.S. Appl. No. 11/429,549, filed May 5, 2006 (Abarzua).
Preliminary Amendment filed May 5, 2006 for U.S. Appl. No. 11/429,549, filed May 5, 2006 (Abarzua).
Issue Notification issued Jul. 29, 2004 for U.S. Appl. No. 09/827,289, filed Apr. 5, 2001 (Abarzua).
Notice of Allowance issued Apr. 1, 2004 for U.S. Appl. No. 09/827,289, filed Apr. 5, 2001 (Abarzua).
Supplemental Response filed Feb. 12, 2004 for U.S. Appl. No. 09/827,289, filed Apr. 5, 2001 (Abarzua).
Notice of Informal or Non-Responsive Amendment issued Feb. 2, 2004 for U.S. Appl. No. 09/827,289, filed Apr. 5, 2001 (Abarzua).
Response after Non-Final Action filed Jan. 19, 2004 for U.S. Appl. No. 09/827,289, filed Apr. 5, 2001 (Abarzua).
Non-Final Rejection issued Sep. 29, 2003 for U.S. Appl. No. 09/827,289, filed Apr. 5, 2001 (Abarzua).
Response after Final Rejection filed Aug. 6, 2003 for U.S. Appl. No. 09/827,289, filed Apr. 5, 2001 (Abarzua).
Advisory Action issued Jun. 2, 2003 for U.S. Appl. No. 09/827,289, filed Apr. 5, 2001 (Abarzua).
Amendment after Final Rejection filed May 6, 2003 for U.S. Appl. No. 09/827,289, filed Apr. 5, 2001 (Abarzua).
Final Rejection issued Feb. 10, 2003 for U.S. Appl. No. 09/827,289, filed Apr. 5, 2001 (Abarzua).
Response after Non-Final Action filed Jan. 13, 2003 for U.S. Appl. No. 09/827,289, filed Apr. 5, 2001 (Abarzua).
Non-Final Rejection issued Jul. 29, 2002 for U.S. Appl. No. 09/827,289, filed Apr. 5, 2001 (Abarzua).
Response to Election / Restriction filed Jun. 19, 2002 for U.S. Appl. No. 09/827,289, filed Apr. 5, 2001 (Abarzua).
Restriction Requirement issued Jun. 11, 2002 for U.S. Appl. No. 09/827,289, filed Apr. 5, 2001 (Abarzua).
Notice of Abandonment issued Sep. 20, 2007 for U.S. Appl. No. 10/177,629, filed Jun. 19, 2002 (Wiltshire).
Final Rejection issued Aug. 21, 2006 for U.S. Appl. No. 10/177,629, filed Jun. 19, 2002 (Wiltshire).
Response after Non-Final Action & Terminal Disclaimer filed Jun. 9, 2006 for U.S. Appl. No. 10/177,629, filed Jun. 19, 2002 (Wiltshire).
Non-Final Rejection issued Jan. 10, 2006 for U.S. Appl. No. 10/177,629, filed Jun. 19, 2002 (Wiltshire).
Response to Notice of Non-Compliant Amendment filed Oct. 25, 2005 for U.S. Appl. No. 10/177,629, filed Jun. 19, 2002 (Wiltshire).
Notice of Informal or Non-Responsive Amendment issued Sep. 30, 2005 for U.S. Appl. No. 10/177,629, filed Jun. 19, 2002 (Wiltshire).
Response to Election / Restriction filed Sep. 16, 2005 for U.S. Appl. No. 10/177,629, filed Jun. 19, 2002 (Wiltshire).
Restriction Requirement issued Mar. 17, 2005 for U.S. Appl. No. 10/177,629, filed Jun. 19, 2002 (Wiltshire).
Issue Notification issued Feb. 9, 2005 for U.S. Appl. No. 09/931,736, filed Aug. 17, 2001 (Shao).
Notice of Allowance issued Nov. 18, 2004 for U.S. Appl. No. 09/931,736, filed Aug. 17, 2001 (Shao).
Appeal Brief filed Aug. 27, 2004 for U.S. Appl. No. 09/931,736, filed Aug. 17, 2001 (Shao).
Advisory Action issued May 4, 2004 for U.S. Appl. No. 09/931,736, filed Aug. 17, 2001 (Shao).
Response after Notice of Appeal filed Feb. 27, 2004. For U.S. Appl. No. 09/931,736, filed Aug. 17, 2001 (Shao).
Notice of Appeal filed Feb. 27, 2004 for U.S. Appl. No. 09/931,736, filed Aug. 17, 2001 (Shao).
Final Rejection issued Dec. 3, 2003 for U.S. Appl. No. 09/931,736, filed Aug. 17, 2001 (Shao).
Response after Non-Final Action filed Sep. 18, 2003 for U.S. Appl. No. 09/931,736, filed Aug. 17, 2001 (Shao).
Non-Final Rejection issued Jun. 30, 2003 for U.S. Appl. No. 09/931,736, filed Aug. 17, 2001 (Shao).
Response to Election / Restriction filed May 14, 2003 for U.S. Appl. No. 09/931,736, filed Aug. 17, 2001 (Shao).
Restriction Requirement issued Apr. 15, 2003 for U.S. Appl. No. 09/931,736, filed Aug. 17, 2001 (Shao).
Notice of Abandonment issued Aug. 8, 2006 for U.S. Appl. No. 10/931,015, filed Aug. 31, 2004 (Shao).
Final Rejection issued Jan. 9, 2006 for U.S. Appl. No. 10/931,015, filed Aug. 31, 2004 (Shao).
Response after Non-Final Action filed Aug. 24, 2005 for U.S. Appl. No. 10/931,015, filed Aug. 31, 2004 (Shao).
Non-Final Rejection issued May 24, 2005 for U.S. Appl. No. 10/931,015, filed Aug. 31, 2004 (Shao).
Response to Election / Restriction filed Feb. 24, 2005 for U.S. Appl. No. 10/931,015, filed Aug. 31, 2004 (Shao).
Restriction Requirement issued Jan. 24, 2005 for U.S. Appl. No. 10/931,015, filed Aug. 31, 2004 (Shao).
Preliminary Amendment filed Aug. 31, 2004 for U.S. Appl. No. 10/931,015, filed Aug. 31, 2004 (Shao).
Response after Final Action filed Aug. 8, 2011 for U.S. Appl. No. 11/744,553, filed May 4, 2007 (Korfhage et al.).
Final Rejection issued May 31, 2011 for U.S. Appl. No. 11/744,553, filed May 4, 2007 (Korfhage et al.).
Response after Non-Final Action filed Feb. 22, 2011 for U.S. Appl. No. 11/744,553, filed May 4, 2007 (Korfhage et al.).
Non-Final Rejection issued Sep. 14, 2010 for U.S. Appl. No. 11/744,553, filed May 4, 2007 (Korfhage et al.).
Response to Final Rejection filed Mar. 1, 2010 for U.S. Appl. No. 11/744,553, filed May 4, 2007 (Korfhage et al.).
Advisory Action issued Feb. 17, 2010 for U.S. Appl. No. 11/744,553, filed May 4, 2007 (Korfhage et al.).
Response after Non-Final Action filed Jan. 28, 2010 for U.S. Appl. No. 11/744,553, filed May 4, 2007 (Korfhage et al.).
Final Rejection issued Apr. 15, 2009 for U.S. Appl. No. 11/744,553, filed May 4, 2007 (Korfhage et al.).
Response after Non-Final Action filed Dec. 17, 2008 for U.S. Appl. No. 11/744,553, filed May 4, 2007 (Korfhage et al.).
Examiner Interview Summary issued Dec. 15, 2008 for U.S. Appl. No. 11/744,553, filed May 4, 2007 (Korfhage et al.).
Non-Final Rejection issued Aug. 19, 2008 for U.S. Appl. No. 11/744,553, filed May 4, 2007 (Korfhage et al.).
Response to Restriction Requirement filed Jun. 5, 2008 for U.S. Appl. No. 11/744,553, filed May 4, 2007 (Korfhage et al.).
Restriction Requirement issued May 16, 2008 for U.S. Appl. No. 11/744,553, filed May 4, 2007 (Korfhage et al.).
Preliminary Amendment filed Mar. 3, 2008 for U.S. Appl. No. 11/991,435, filed on N/A (Korfhage).
Issue Notification issued Nov. 23, 1998 for U.S. Appl. No. 08/563,912, filed Nov. 21, 1995 (Lizardi).
Notice of Allowance issued Aug. 14, 1998 for U.S. Appl. No. 08/563,912, filed Nov. 21, 1995 (Lizardi).
Amendment/Argument filed Aug. 6, 1998 for U.S. Appl. No. 08/563,912, filed Nov. 21, 1995 (Lizardi).
Notice of Appeal filed Jun. 9, 1998 for U.S. Appl. No. 08/563,912, filed Nov. 21, 1995 (Lizardi).
Final Rejection issued Dec. 9, 1997 for U.S. Appl. No. 08/563,912, filed Nov. 21, 1995 (Lizardi).
Amendment and Response filed Aug. 28, 1997 for U.S. Appl. No. 08/563,912, filed Nov. 21, 1995 (Lizardi).
Non-Final Office Action issued Feb. 28, 1997 for U.S. Appl. No. 08/563,912, filed Nov. 21, 1995 (Lizardi).
Response to Election / Restriction filed Oct. 24, 1996 for U.S. Appl. No. 08/563,912, filed Nov. 21, 1995 (Lizardi).
Restriction Requirement issued Sep. 24, 1996 for U.S. Appl. No. 08/563,912, filed Nov. 21, 1995 (Lizardi).
Issue Notification issued Mar. 15, 2001 for U.S. Appl. No. 09/132,553, filed Aug. 11, 1998 (Lizardi).
Notice of Allowce issued Nov. 7, 2000 for U.S. Appl. No. 09/132,553, filed Aug. 11, 1998 (Lizardi).
Response to Office Action filed Aug. 11, 2000 for U.S. Appl. No. 09/132,553, filed Aug. 11, 1998 (Lizardi).
Non-Final Rejection issued Apr. 11, 2000 for U.S. Appl. No. 09/132,553, filed Aug. 11, 1998 (Lizardi).
Response after Non-Final Action with Terminal Disclaimer filed Jan. 13, 2000 for U.S. Appl. No. 09/132,553, filed Aug. 11, 1998 (Lizardi).
Non-Final Rejection issued Sep. 13, 1999 for U.S. Appl. No. 09/132,553, filed Aug. 11, 1998 (Lizardi).
Preliminary Amendment filed Aug. 11, 1998 for U.S. Appl. No. 09/132,553, filed Aug. 11, 1998 (Lizardi).

Issue Notification issued Jan. 18, 2002 for U.S. Appl. No. 09/644,723, filed Aug. 23, 2000 (Lizardi).
Notice of Allowance issued Oct. 1, 2001 for U.S. Appl. No. 09/644,723, filed Aug. 23, 2000 (Lizardi).
Response after Non-Final Action with Terminal Disclaimer filed Jul. 13, 2001 for U.S. Appl. No. 09/644,723, filed Aug. 23, 2000 (Lizardi).
Non-Final Rejection issued Mar. 13, 2001 for U.S. Appl. No. 09/644,723, filed Aug. 23, 2000 (Lizardi).
Preliminary Amendment filed Aug. 23, 2000 for U.S. Appl. No. 09/644,723, filed Aug. 23, 2000 (Lizardi).
Issue Notification issued Jan. 19, 2001 for U.S. Appl. No. 09/132,552, filed Aug. 11, 1998 (Lizardi).
Non-Final Rejection issued Feb. 16, 2011 for U.S. Appl. No. 11/870,715, filed Oct. 11, 2007 (Korfhage et al.).
Response after Final Rejection filed Nov. 30, 2009 for U.S. Appl. No. 11/870,715, filed Oct. 11, 2007 (Korfhage et al.).
Final Rejection issued Oct. 16, 2009 for U.S. Appl. No. 11/870,715, filed Oct. 11, 2007 (Korfhage et al.).
Response after Final Rejection filed Jul. 24, 2009 for U.S. Appl. No. 11/870,715, filed Oct. 11, 2007 (Korfhage et al.).
Examiner Interview Summary issued Jul. 15, 2009 for U.S. Appl. No. 11/870,715, filed Oct. 11, 2007 (Korfhage et al.).
Final Rejection issued May 13, 2009 for U.S. Appl. No. 11/870,715, filed Oct. 11, 2007 (Korfhage et al.).
Response after Non-Final Action filed Feb. 9, 2009 for U.S. Appl. No. 11/870,715, filed Oct. 11, 2007 (Korfhage et al.).
Non-Final Rejection issued Nov. 12, 2008 for U.S. Appl. No. 11/870,715, filed Oct. 11, 2007 (Korfhage et al.).
Notice of Allowance issued Jul. 12, 2000 for U.S. Appl. No. 09/132,552, filed Aug. 11, 1998 (Lizardi).
Amendment and Response filed Jun. 14, 2000 for U.S. Appl. No. 09/132,552, filed Aug. 11, 1998 (Lizardi).
Final Rejection issued Apr. 6, 2000 for U.S. Appl. No. 09/132,552, filed Aug. 11, 1998 (Lizardi).
Response after Non-Final Action & Terminal Disclaimer filed Jan. 13, 2000 for U.S. Appl. No. 09/132,552, filed Aug. 11, 1998 (Lizardi).
Non-Final Rejection issued Sep. 13, 1999 for U.S. Appl. No. 09/132,552, filed Aug. 11, 1998 (Lizardi).
Preliminary Amendment filed Aug. 11, 1998 for U.S. Appl. No. 09/132,552, filed Aug. 11, 1998 (Lizaidi).
Issue Notification issued Sep. 9, 2004 for U.S. Appl. No. 10/038,718, filed Jan. 2, 2002 (Lizardi).
Notice of Allowance issued Apr. 21, 2004 for U.S. Appl. No. 10/038,718, filed Jan. 2, 2002 (Lizardi).
Response after Non-Final Action & Terminal Disclaimer filed Jan. 16, 2004 for U.S. Appl. No. 10/038,718, filed Jan. 2, 2002 (Lizardi).
Non-Final Rejection issued Oct. 22, 2003 for U.S. Appl. No. 10/038,718, filed Jan. 2, 2002 (Lizardi).
Response to Election / Restriction filed Jul. 14, 2003 for U.S. Appl. No. 10/038,718, filed Jan. 2, 2002 (Lizardi).
Restriction Requirement issued Mar. 13, 2003 for U.S. Appl. No. 10/038,718, filed Jan. 2, 2002 (Lizardi).
Preliminary Amendment filed Jan. 2, 2002 for U.S. Appl. No. 10/038,718, filed Jan. 2, 2002 (Lizardi).
Certificate of Correction issued Oct. 26, 2010 for U.S. Appl. No. 10/896,513, filed Jul. 22, 2004 (Lizardi).
Issue Notification issued Oct. 28, 2009 for U.S. Appl. No. 10/896,513, filed Jul. 22, 2004 (Lizardi).
Notice of Allowance issued Jul. 9, 2009 for U.S. Appl. No. 10/896,513, filed Jul. 22, 2004 (Lizardi).
Amendment and Response filed Mar. 26, 2009 for U.S. Appl. No. 10/896,513, filed Jul. 22, 2004 (Lizardi).
Interview Summary issued Mar. 12, 2009 for U.S. Appl. No. 10/896,513, filed Jul. 22, 2004 (Lizardi).
Non-Final Rejection issued Nov. 17, 2008 for U.S. Appl. No. 10/896,513, filed Jul. 22, 2004 (Lizardi).
Amendment and Response filed Aug. 29, 2008 for U.S. Appl. No. 10/896,513, filed Jul. 22, 2004 (Lizardi).
Advisory Action issued Jul. 23, 2008 for U.S. Appl. No. 10/896,513, filed Jul. 22, 2004 (Lizardi).

Amendment After Final Rejection filed Jun. 18, 2008 for U.S. Appl. No. 10/896,513, filed Jul. 22, 2004 (Lizardi).
Interview Summary issued Jun. 13, 2008 for U.S. Appl. No. 10/896,513, filed Jul. 22, 2004 (Lizardi).
Final Rejection issued Mar. 18, 2008 for U.S. Appl. No. 10/896,513, filed Jul. 22, 2004 (Lizardi).
Amendment After Non-Final Rejection with Terminal Disclaimer filed Dec. 11, 2007 for U.S. Appl. No. 10/896,513, filed Jul. 22, 2004 (Lizardi).
Non-Final Rejection issued Jun. 11, 2007 for U.S. Appl. No. 10/896,513, filed Jul. 22, 2004 (Lizardi).
Response to Election / Restriction filed Mar. 29, 2007 for U.S. Appl. No. 10/896,513, filed Jul. 22, 2004 (Lizardi).
Restriction Requirement issued Jan. 19, 2007 for U.S. Appl. No. 10/896,513, filed Jul. 22, 2004 (Lizardi).
Preliminary Amendment filed Jan. 25, 2005 for U.S. Appl. No. 10/896,513, filed Jul. 22, 2004 (Lizardi).
Issue Notification issued Sep. 8, 2000 for U.S. Appl. No. 08/946,732, filed Oct. 8, 1997 (Lizardi).
Office Communication issued May 3, 2000 for U.S. Appl. No. 08/946,732, filed Oct. 8, 1997 (Lizardi).
Notice of Allowance issued Jun. 22, 1999 for U.S. Appl. No. 08/946,732, filed Oct. 8, 1997 (Lizardi).
Amendment and Response filed Mar. 31, 1999 for U.S. Appl. No. 08/946,732, filed Oct. 8, 1997 (Lizardi).
Non-Final Rejection issued Oct. 1, 1998 for U.S. Appl. No. 08/946,732, filed Oct. 8, 1997 (Lizardi).
Issue Notification issued Aug. 9, 2001 for U.S. Appl. No. 09/397,915, filed Sep. 17, 1999 (Lizardi).
Notice of Allowance issued Apr. 9, 2001 for U.S. Appl. No. 09/397,915, filed Sep. 17, 1999 (Lizardi).
Response after Non-Final Action with Terminal Disclaimer filed Jan. 16, 2001 for U.S. Appl. No. 09/397,915, filed Sep. 17, 1999 (Lizardi).
Non-Final Rejection issued Aug. 14, 2000 for U.S. Appl. No. 09/397,915, filed Sep. 17, 1999 (Lizardi).
Preliminary Amendment filed Sep. 17, 1999 for U.S. Appl. No. 09/397,915, filed Sep. 17, 1999 (Lizardi).
Issue Notification issued Oct. 16, 2003 for U.S. Appl. No. 09/911,226, filed Jul. 23, 2001 (Lizardi).
Notice of Allowance issued Jun. 3, 2003 for U.S. Appl. No. 09/911,226, filed Jul. 23, 2001 (Lizardi).
Amendment and Response & Terminal Disclaimer filed Mar. 19, 2003 for U.S. Appl. No. 09/911,226, filed Jul. 23, 2001 (Lizardi).
Non-Final Rejection issued Dec. 18, 2002 for U.S. Appl. No. 09/911,226, filed Jul. 23, 2001 (Lizardi).
Preliminary Amendment filed Jul. 23, 2001 for U.S. Appl. No. 09/911,226, filed Jul. 23, 2001 (Lizardi).
Notice of Abandonment issued Oct. 28, 2009 for U.S. Appl. No. 10/700,018, filed Nov. 3, 2003 (Lizardi).
Advisory Action issued Apr. 2, 2009 for U.S. Appl. No. 10/700,018, filed Nov. 3, 2003 (Lizardi).
Notice of Appeal filed Mar. 13, 2009 for U.S. Appl. No. 10/700,018, filed Nov. 3, 2003 (Lizardi).
Amendment after Final Rejection filed Jan. 27, 2009 for U.S. Appl. No. 10/700,018, filed Nov. 3, 2003 (Lizardi).
Final Rejection issued Sep. 15, 2008 for U.S. Appl. No. 10/700,018, filed Nov. 3, 2003 (Lizardi).
Amendment after Non-Final Rejection filed Jun. 12, 2008 for U.S. Appl. No. 10/700,018, filed Nov. 3, 2003 (Lizardi).
Non-Final Rejection issued Jan. 24, 2008 for U.S. Appl. No. 10/700,018, filed Nov. 3, 2003 (Lizardi).
Response after Non-Final Action filed Oct. 31, 2007 for U.S. Appl. No. 10/700,018, filed Nov. 3, 2003 (Lizardi).
Non-Final Rejection issued Aug. 8, 2007 for U.S. Appl. No. 10/700,018, filed Nov. 3, 2003 (Lizardi).
Response after Non-Final Action filed May 14, 2007 for U.S. Appl. No. 10/700,018, filed Nov. 3, 2003 (Lizardi).
Non-Final Rejection issued Nov. 14, 2006 for U.S. Appl. No. 10/700,018, filed Nov. 3, 2003 (Lizardi).
Response after Non-Final Action filed Aug. 24, 2006 for U.S. Appl. No. 10/700,018, filed Nov. 3, 2003 (Lizardi).
Non-Final Rejection issued May 18, 2006 for U.S. Appl. No. 10/700,018, filed Nov. 3, 2003 (Lizardi).

Preliminary Amendment filed Nov. 3, 2003 for U.S. Appl. No. 10/700,018, filed Nov. 3, 2003 (Lizardi).
Issue Notification issued Oct. 25, 2001 for U.S. Appl. No. 09/357,487, filed Jul. 20, 1999 (Lizardi).
Notice of Allowance issued Jun. 5, 2001 for U.S. Appl. No. 09/357,487, filed Jul. 20, 1999 (Lizardi).
Amendment and Response filed May 18, 2001 for U.S. Appl. No. 09/357,487, filed Jul. 20, 1999 (Lizardi).
Final Rejection issued Feb. 13, 2001 for U.S. Appl. No. 09/357,487, filed Jul. 20, 1999 (Lizardi).
Amendment and Response filed Jan. 25, 2001 for U.S. Appl. No. 09/357,487, filed Jul. 20, 1999 (Lizardi).
Non-Final Rejection issued Oct. 25, 2000 for U.S. Appl. No. 09/357,487, filed Jul. 20, 1999 (Lizardi).
Amendment and Response filed Sep. 12, 2000 for U.S. Appl. No. 09/357,487, filed Jul. 20, 1999 (Lizardi).
Non-Final Rejection issued May 12, 2000 for U.S. Appl. No. 09/357,487, filed Jul. 20, 1999 (Lizardi).
International Preliminary Examination Report issued Mar. 3, 2004 for PCT/US02/02601 filed on Jan. 30, 2002 (Applicant—Molecular Staging, Inc.).
Written Opinion issued Jun. 6, 2003 for PCT/US02/02601 filed on Jan. 30, 2002 (Applicant—Molecular Staging, Inc.).
International Search Report issued May 7, 2002 for PCT/US02/02601 filed on Jan. 30, 2002 (Applicant—Molecular Staging, Inc.).
Communication regarding Expiry of Time Limit for Notice of Opposition issued Mar. 26, 2009 for EP 1928481.9, which claims priority to PCT/US01/11947 filed on Apr. 12, 2001 (Applicant—Molecular Staging, Inc.).
Communication under Rule 51(4) EPC issued Sep. 11, 2007 for EP 1928481.9, which claims priority to PCT/US01/11947 filed on Apr. 12, 2001 (Applicant—Molecular Staging, Inc.).
Response filed Nov. 27, 2006 for EP 1928481.9, which claims priority to PCT/US01/11947 filed on Apr. 12, 2001 (Applicant—Molecular Staging, Inc.).
Invitation pursuant to Article 96(2) EPC and Rule 51(2) EPC issued Nov. 10, 2006 for EP 1928481.9, which claims priority to PCT/US01/11947 filed on Apr. 12, 2001 (Applicant—Molecular Staging, Inc.).
Response filed Mar. 6, 2006 for EP 1928481.9, which claims priority to PCT/US01/11947, which claims priority to PCT/US01/11947 filed on Apr. 12, 2001 (Applicant—Molecular Staging, Inc.).
Communication pursuant to Article 96(2) EPC issued May 25, 2005 for EP 1928481.9, which claims priority to PCT/US01/11947 filed on Apr. 12, 2001 (Applicant—Molecular Staging, Inc.).
International Preliminary Examination Report issued Jan. 10, 2003 for PCT/US01/11947 filed on Apr. 12, 2001 (Applicant—Molecular Staging, Inc.).
International Search Report issued Oct. 30, 2002 for PCT/US01/11947 filed on Apr. 12, 2001 (Applicant—Molecular Staging, Inc.).
Notice of Abandonment issued Jun. 7, 2007 for CA 2405456, which claims priority to PCT/US01/11947 filed on Apr. 12, 2001 (Applicant—Molecular Staging, Inc.).
Notice of Reinstatement issued Jan. 10, 2005 for CA 2405456, which claims priority to PCT/US01/11947 filed on Apr. 12, 2001 (Applicant—Molecular Staging, Inc.).
Notice of Abandonment issued Jun. 8, 2004 for CA 2405456, which claims priority to PCT/US01/11947 filed on Apr. 12, 2001 (Applicant—Molecular Staging, Inc.).
Voluntary Amendment filed Apr. 11, 2003 for CA 2405456, which claims priority to PCT/US01/11947 filed on Apr. 12, 2001 (Applicant—Molecular Staging, Inc.).
Notice of Abandonment issued Feb. 26, 2007 for AU 2001269944, which claims priority to PCT/US01/19657 filed on Jun. 20, 2001 (Applicant—Molecular Staging, Inc.).
Examiner's Report #2 issued May 26, 2006 for AU 2001269944, which claims priority to PCT/US01/19657 filed on Jun. 20, 2001 (Applicant—Molecular Staging, Inc.).
Response filed May 16, 2006 for AU 2001269944, which claims priority to PCT/US01/19657 filed on Jun. 20, 2001 (Applicant—Molecular Staging, Inc.).
Examiner's Report #1 issued May 19, 2005 for AU 2001269944, which claims priority to PCT/US01/19657 filed on Jun. 20, 2001 (Applicant—Molecular Staging, Inc.).

Direction to Request Examination filed Oct. 30, 2003 for AU 2001269944, which claims priority to PCT/US01/19657 filed on Jun. 20, 2001 (Applicant—Molecular Staging, Inc.).
Notice of Abandonment issued Aug. 15, 2007 for CA 2411838, which claims priority to PCT/US01/19657 filed on Jun. 20, 2001 (Applicant—Molecular Staging, Inc.).
Response to Examination Report filed Nov. 23, 2005 for CN 01811542.X, which claims priority to PCT/US01/19657 filed on Jun. 20, 2001 (Applicant—Molecular Staging, Inc.).
Examination Report issued Jul. 8, 2005 for CN 01811542.X, which claims priority to PCT/US01/19657 filed on Jun. 20, 2001 (Applicant—Molecular Staging, Inc.).
Noting of Loss of Rights pursuant to Rule 112(1) EPC issued Sep. 13, 2010 for EP 1948505.1, which claims priority to PCT/US01/19657 filed on Jun. 20, 2001 (Applicant—Molecular Staging, Inc.).
Communication pursuant to Article 94(3) EPC issued Jan. 29, 2010 for EP 1948505.1, which claims priority to•PCT/US01/19657 filed on Jun. 20, 2001 (Applicant—Molecular Staging, Inc.).
Response to Rule 70(2) EPC Communication filed Oct. 6, 2009 for EP 1948505.1, which claims priority to PCT/US01/19657 filed on Jun. 20, 2001 (Applicant—Molecular Staging, Inc.).
Supplementary European Search Report issued Jul. 27, 2009 for EP 1948505.1, which claims priority to PCT/US01/19657 filed on Jun. 20, 2001 (Applicant—Molecular Staging, Inc.).
Notice of Allowance issued Mar. 1, 2011 for JP 2002-503102, which claims priority to PCT/US01/19657 filed on Jun. 20, 2001 (Applicant—Molecular Staging, Inc.).
Argument and Amendment filed Mar. 19, 2010 for JP 2002-503102, which claims priority to PCT/US01/19657 filed on Jun. 20, 2001 (Applicant—Molecular Staging, Inc.).
Notice of Rejection issued Dec. 22, 2009 for JP 2002-503102, which claims priority to PCT/US01/19657 filed on Jun. 20, 2001 (Applicant—Molecular Staging, Inc.).
Request for Examination filed Jan. 11, 2007 for JP 2002-503102, which claims priority to PCTTUS01/19657 filed on Jun. 20, 2001 (Applicant—Molecular Staging, Inc.).
International Preliminary Examination Report issued Sep. 27, 2002 for PCT/US01/19657 filed on Jun. 20, 2001 (Applicant—Molecular Staging, Inc.).
Written Opinion issued Jun. 26, 2002 for PCT/US01/19657 filed on Jun. 20, 2001 (Applicant—Molecular Staging, Inc.).
International Search Report issued Aug. 29, 2001 for PCT/US01/19657 filed on Jun. 20, 2001 (Applicant—Molecular Staging, Inc.).
Issue Notification issued Dec. 13, 2002 for SG 200207285-8, which claims priority to PCT/US01/19657 filed on Jun. 20, 2001 (Applicant—Molecular Staging, Inc.).
Office Action issued Oct. 3, 2005 for TW 90114960 filed on Jun. 28, 2001 (Applicant—Molecular Staging, Inc.).
Response to Office Action (no translation) filed Sep. 13, 2005 for TW 90114960 filed on Jun. 28, 2001 (Applicant—Molecular Staging, Inc.).
Office Action issued May 16, 2005 for TW90114960 filed on Jun. 28, 2001 (Applicant—Molecular Staging, Inc.).
Notice of Acceptance issued Mar. 29, 2006 for AU 2001271722, which claims priority to PCT/US01/20933 filed on Jul. 2, 2001 (Applicant—Molecular Staging, Inc).
Response to Examination Report filed Mar. 17, 2006 for AU 2001271722, which claims priority to PCT/US01/20933 filed on Jul. 2, 2001 (Applicant—Molecular Staging, Inc.).
Examination Report issued Jun. 17, 2005 for AU 2001271722, which claims priority to PCT/US01/20933 filed on Jul. 2, 2001 (Applicant—Molecular Staging, Inc.).
Communication pursuant to 45(3) issued Jul. 20, 2004 for AU 2001271722, which claims priority to PCT/US01/20933 filed on Jul. 2, 2001 (Applicant—Molecular Staging, Inc.).
Direction to Request Examination filed Nov. 6, 2003 for AU 2001271722, which claims priority to PCT/US01/20933 filed on Jul. 2, 2001 (Applicant—Molecular Staging.
Notice of Abandonment issued Aug. 28, 2007 for CA 2411794, which claims priority to PCT/US01/20933 filed on Jul. 2, 2001 (Applicant—Molecular Staging, Inc.).

Notice of National Entry issued Jan. 16, 2003 for CA 2411794, which claims priority to PCT/US01/20933 filed on Jul. 2, 2001 (Applicant—Molecular Staging, Inc.).
Communication re: the Expiry of the Time Limit to File Opposition issued Aug. 6, 2008 for EP 1950759.9, which claims priority to PCT/US01/20933 filed on Jul. 2, 2001 (Applicant—Molecular Staging, Inc.).
Decision to Grant pursuant to Article 97(2) EPC issued Sep. 6, 2007 for EP 1950759.9, which claims priority to PCT/US/01/20933 filed on Jul. 2, 2001 (Applicant—Molecular Staging, Inc.).
Response to Communication filed Aug. 17, 2007 for EP 1950759.9, which claims priority to PCT/US01/20933 filed on Jul. 2, 2001 (Applicant—Molecular Staging, Inc.).
Communication under Rule 51(4) issued Apr. 26, 2007 for EP 1950759.9, which claims priority to PCT/US01/20933 filed on Jul. 2, 2001 (Applicant—Molecular Staging, Inc.).
Response to Communication filed Jul. 5, 2006 for EP 1950759.9, which claims priority to PCT/US01/20933 filed on Jul. 2, 2001 (Applicant—Molecular Staging, Inc.).
Communication pursuant to Article 96(2) EPC issued Apr. 24, 2006 for EP 1950759.9, which claims priority to PCT/US01/20933 filed on Jul. 2, 2001 (Applicant—Molecular.
Response to Communication filed Oct. 24, 2005 for EP 1950759.9, which claims priority to PCT/US01/20933 filed on Jul. 2, 2001 (Applicant—Molecular Staging, Inc.).
Communication pursuant to Article 96(2) EPC issued Jun. 16, 2005 for EP 1950759.9, which claims priority to PCT/US01/20933 filed on Jul. 2, 2001 (Applicant—Molecular Staging, Inc.).
Response to Communication filed Sep. 7, 2004 for EP 1950759.9, which claims priority to PCT/US01/20933 filed on Jul. 2, 2001 (Applicant—Molecular Staging, Inc.).
Communication pursuant to Article 96(1) and Rule 51(1) EPC issued Jul. 6, 2004 for 1950759.9, which claims priority to PCT/US/01/20933 filed on Jul. 2, 2001 (Applicant—Molecular Staging, Inc.).
European Search Report issued Jul. 1, 2004 for EP 1950759.9, which claims priority to PCT/US01/20933 filed on Jul. 2, 2001 (Applicant—Molecular Staging, Inc.).
International Preliminary Examination Report issued Sep. 29, 2002 for PCT/US01/20933 filed on Jul. 2, 2001 (Applicants—Molecular Staging, Inc., Yale University).
International Search Report issued Nov. 6, 2001 for PCT/US01/20933 filed on Jul. 2, 2001 (Applicants—Molecular Staging, Inc., Yale University).
International Preliminary Examination Report issued Sep. 6, 2004 for PCT/US02/15045 filed on May 10, 2002 (Applicant—Molecular Staging, Inc.).
Written Opinion issued Mar. 19, 2004 for PCT/US02/15045 filed on May 10, 2002 (Applicant—Molecular Staging, Inc.).
International Search Report issued Feb. 10, 2003 for PCT/US02/15045 filed on May 10, 2002 (Applicant—Molecular Staging, Inc.).
Examination Report issued Jan. 8, 2007 for AU 2002362874, which claims priority to PCT/US02/33244 filed on Oct. 15, 2002 (Applicant—Molecular Staging, Inc.).
Notice of Abandonment issued Dec. 10, 2007 for CA 246933, which claims priority to PCT/US02/33244 filed on Oct. 15, 2002 (Applicant—Molecular Staging, Inc.).
Communication pursuant to Article 114(2) EPC issued Oct. 23, 2009 for EP 2801776.2, which claims priority to PCT/US02/33244 filed on Oct. 15, 2002 (Applicant—Molecular Staging, Inc.).
Response to Communication filed Dec. 5, 2007 for EP 2801776.2, which claims priority to PCT/US02/33244 filed on Oct. 15, 2002 (Applicant—Molecular Staging, Inc.).
Communication pursuant to Article 96(2) EPC issued Aug. 7, 2007 for EP 2801776.2, which claims priority to PCT/US02/33244filed on Oct. 15, 2002 (Applicant—Molecular Staging, Inc.).
Supplementary European Search Report issued Apr. 11, 2007 for EP 2801776.2, which claims priority to PCT/US02/33244 filed on Oct. 15, 2002 (Applicant—Molecular Staging, Inc.).
Response to Communication filed Dec. 6, 2006 for EP 2801776.2, which claims priority to PCT/US02/33244 filed on Oct. 15, 2002 (Applicant—Molecular Staging, Inc.).

Communication issued Nov. 7, 2006 for EP 2801776.2, which claims priority to PCT/US02/33244 filed on Oct. 15, 2002 (Applicant—Molecular Staging, Inc.).
International Preliminary Examination Report issued May 11, 2004 for PCT/US02/33244 filed on Oct. 15, 2002 (Applicant—Molecular Staging, Inc.).
Written Opinion issued Feb. 24, 2004 for PCT/US02/33244 filed on Oct. 15, 2002 (Applicant—Molecular Staging, Inc.).
International Search Report issued Oct. 17, 2003 for PCT/US02/33244 filed on Oct. 15, 2002 (Applicant—Molecular Staging, Inc.).
Notice of Acceptance issued Nov. 22, 1999 for AU 10240/97, which claims priority to PCT/US96/18812 filed on Nov. 21, 1996 (Applicant—Yale University).
First Statement of Proposed Amendments filed Oct. 15, 1999 for AU 10240/97, which claims priority to PCT/US96/18812 filed on Nov. 21, 1996 (Applicant—Yale University).
First Examination Report issued Apr. 30, 1999 for AU 10240/97, which claims priority to PCT/US96/18812 filed on Nov. 21, 1996 (Applicant—Yale University).
Notice of National Processing Completion issued Apr. 20, 2001 for BE 96940601.6, which claims priority to PCTTUS96/18812 filed on Nov. 21, 1996 (Applicant—Yale University).
Notice of Allowance issued Jun. 13, 2007 for CA 2236161, which claims priority to PCT/US96/18812 filed on Nov. 21, 1996 (Applicant—Yale University).
Comments and Amendments after Examiner's Report filed Oct. 4, 2006 for CA 2236161, which claims priority to PCT/US96/18812 filed on Nov. 21, 1996 (Applicant—Yale University).
Examination Report issued Apr. 4, 2006 for CA 2236161, which claims priority to PCT/US96/18812 filed on Nov. 21, 1996 (Applicant—Yale University).
Patent Granted issued Aug. 2, 2001 for DE 862652, which claims priority to PCT/US96/18812 filed on Nov. 21, 1996 (Applicant—Yale University).
Communication regarding Expiry of Opposition Time Period issued Jan. 15, 2002 for EP 862652, which claims priority to PCT/US96/18812 filed on Nov. 21, 1996 (Applicant—Yale University).
Decision to Grant issued Jan. 25, 2001 for EP 862652, which claims priority to PCT/US96/18812 filed on Nov. 21, 1996 (Applicant—Yale University).
Response to Communication under Rule 51(4) filed Dec. 21, 1999 for EP 862652, which claims priority to PCT/US96/18812 filed on Nov. 21, 1996 (Applicant—Yale University).
Communication under Rule 51(4) issued Jul. 1, 1999 for EP 862652, which claims priority to PCT/US96/18812 filed on Nov. 21, 1996 (Applicant—Yale University).
Notice of Allowance issued May 9, 2007 for JP 9-519942, which claims priority to PCT/US96/18812 filed on Nov. 21, 1996 (Applicant—Yale University).
Amended Claim Set filed Dec. 26, 2006 for JP 9-519942, which claims priority to PCT/US96/18812 filed on Nov. 21, 1996 (Applicant—Yale University).
Examination Report issued Jun. 27, 2006 for JP 9-519942, which claims priority to PCT/US96/18812 filed on Nov. 21, 1996 (Applicant—Yale University).
International Preliminary Examination Report issued Jan. 28, 1998 for PCT/US96/18812 filed on Nov. 21, 1996 (Applicant—Yale University).
Response to Written Opinion issued Nov. 18, 1997 for PCT/US96/18812 filed on Nov. 21, 1996 (Applicant—Yale University).
Written Opinion issued Aug. 21, 1997 for PCT/US96/18812 filed on Nov. 21, 1996 (Applicant—Yale University).
International Search Report issued Jun. 30, 1997 for PCT/US96/18812 filed on Nov. 21, 1996 (Applicant—Yale University).
International Search Report issued Apr. 28, 2003 for PCT/US03/00678 filed on Jan. 9, 2003 (Applicant—Molecular Staging, Inc.).
Notice of Acceptance issued May 12, 2005 for AU 27819/00, which claims prioity to PCT/AU99/01110 filed on Dec. 14, 1999 (Applicant—Molecular Staging, Inc.).
Response to Examination Report filed Apr. 15, 2005 for AU 27819/00, which claims prioity to PCT/AU99/01110 filed on Dec. 14, 1999 (Applicant—Molecular Staging, Inc.).

Examination Report issued Dec. 8, 2004 for AU 27819/00, which claims prioity to PCT/AU99/01110 filed on Dec. 14, 1999 (Applicant—Molecular Staging, Inc.).
Response to Examination Report filed Nov. 30, 2004 for AU 27819/00, which claims prioity to PCT/AU99/01110 filed on Dec. 14, 1999 (Applicant—Molecular Staging, Inc.).
Examination Report issued Oct. 13, 2004 for AU 27819/0, which claims prioity to PCT/AU99/01110 0 filed on Dec. 14, 1999 (Applicant—Molecular Staging, Inc.).
Response to Examination Report filed Sep. 22, 2004 for AU 27819/00, which claims prioity to PCT/AU99/01110 filed on Dec. 14, 1999 (Applicant—Molecular Staging, Inc.).
Examination Report issued Aug. 8, 2003 for AU 27819/00, which claims prioity to PCT/AU99/01110 filed on Dec. 14, 1999 (Applicant—Molecular Staging, Inc.).
Notice of Abandonment issued Feb. 11, 2008 for CA 2394800, which claims prioity to PCT/AU99/01110 filed on Dec. 14, 1999 (Applicant—Molecular Staging, Inc.).
Notice of Reinstatement issued Jan. 12, 2005 for CA 2394800, which claims priority to PCT/AU99/01110 filed on Dec. 14, 1999 (Applicant—Molecular Staging, Inc.).
Notice of Abandonment issued Feb. 9, 2004 for CA 2394800, which claims priority to PCT/AU99/01110 filed on Dec. 14, 1999 (Applicant—Molecular Staging, Inc.).
European Search Report issued Feb. 21, 2003 for EP 99969209.8, which claims prioity to PCT/AU99/01110 filed on Dec. 14, 1999 (Applicant—Molecular Staging, Inc.).
Notice of Allowance issued Jul. 22, 2008 for JP 2000-588388, which claims prioity to PCT/AU99/01110 filed on Dec. 14, 1999 (Applicant—Molecular Staging, Inc.).
Reasons for Appeal filed Jun. 19, 2008 for JP 2000-588388, which claims priority to PCT/AU99/01110 filed on Dec. 14, 1999 (Applicant—Molecular Staging, Inc.).
Amendment filed May 20, 2008 for JP 2000-588388, which claims prioity to PCT/AU99/01110 filed on Dec. 14, 1999 (Applicant—Molecular Staging, Inc.).
Argument against Final Rejection filed Apr. 8, 2008, which claims prioity to PCT/AU99/01110 for JP 2000-588388 filed on Dec. 14, 1999 (Applicant—Molecular Staging, Inc.).
Examination Report issued Jan. 8, 2008 for JP 2000-588388, which claims prioity to PCT/AU99/01110 filed on Dec. 14, 1999 (Applicant—Molecular Staging, Inc.).
Amendment filed Nov. 26, 2007 for JP 2000-588388, which claims prioity to PCT/AU99/01110 filed on Dec. 14, 1999 (Applicant—Molecular Staging, Inc.).
Examination Report issued Jul. 24, 2007 for JP 2000-588388, which claims prioity to PCT/AU99/01110 filed on Dec. 14, 1999 (Applicant—Molecular Staging, Inc.).
Written Amendment filed Dec. 15, 2004 for JP 2000-588388, which claims prioity to PCT/AU99/01110 filed on Dec. 14, 1999 (Applicant—Molecular Staging, Inc.).
International Preliminary Examination Report issued Oct. 4, 2000 for PCT/AU99/01110 filed on Dec. 14, 1999 (Diatech Pty. Ltd.).
Written Opinion issued Jun. 28, 2000 for PCT/AU99/01110 filed on Dec. 14, 1999 (Diatech Pty. Ltd.).
International Search Report issued Mar. 7, 2000 for PCT/AU99/01110 filed on Dec. 14, 1999 (Diatech Pty. Ltd.).
Notice of Abandonment issued Feb. 5, 2008 for CA 2512196, which claims priority to PCT/US03/39430 filed on Dec. 11, 2003 (Applicant—Qiagen GMBH).
Notice of National Entry issued Oct. 3, 2005 for CA 2512196, which claims priority to PCT/US03/39430 filed on Dec. 11, 2003 (Applicant—Qiagen GMBH).
Communication re: Expiry of Time Period for Opposition issued Apr. 6, 2011 for EP 3796961.5, which claims priority to PCT/US03/39430 filed on Dec. 11, 2003 (Applicant—Qiagen GMBH).
Decision to Grant a European Patent issued May 7, 2010 for EP 3796961.5, which claims priority to PCT/US03/39430 filed on Dec. 11, 2003 (Applicant—Qiagen GMBH).
Response to Communication filed Apr. 1, 2010 for EP 3796961.5, which claims priority to PCT/US03/39430 filed on Dec. 11, 2003 (Applicant—Qiagen GMBH).

Amendment or Correction of the Text for Grant filed Mar. 4, 2010 for EP 3796961.5, which claims priority to PCT/US03/39430 filed on Dec. 11, 2003 (Applicant—Qiagen GMBH).
Response to Communication filed Dec. 10, 2009 for EP 3796961.5, which claims . priority to PCT/US03/39430 filed on Dec. 11, 2003 (Applicant—Qiagen GMBH).
Communication under Rule 71(3) EPC issued Aug. 17, 2009 for EP 3796961.5, which claims priority to PCT/US03/39430 filed on Dec. 11, 2003 (Applicant—Qiagen GMBH).
Response to Communication filed Jul. 7, 2009 for EP 3796961.5, which claims priority to PCT/US03/39430 filed on Dec. 11, 2003 (Applicant—Qiagen GMBH).
Invitation pursuant to Article 94(3) and Rule 71(1) EPC issued Jun. 19, 2009 for EP 3796961.5, which claims priority to PCT/US03/39430 filed on Dec. 11, 2003 (Applicant—Qiagen GMBH).
Response to Communication filed Oct. 25, 2007 for EP 3796961.5, which claims priority to PCT/US03/39430 filed on Dec. 11, 2003 (Applicant—Qiagen GMBH).
Communication pursuant to Article 96(2) EPC issued Jun. 29, 2007 for EP 3796961.5, which claims priority to PCT/US03/39430 filed on Dec. 11, 2003 (Applicant—Qiagen GMBH).
Response to Communication filed Mar. 14, 2007 for EP 3796961.5, which claims . priority to PCT/US03/39430 filed on Dec. 11, 2003 (Applicant—Qiagen GMBH).
Proceeding further with EP patent application pursuant to Article 96(1) and Rule 51(1) EPC issued Feb. 2, 2007 for EP 3796961.5, which claims priority to PCT/US03/39430 filed on Dec. 11, 2003 (Applicant—Qiagen GMBH).
Supplementary European Search Report issued Jan. 16, 2007 for EP 3796961.5, which claims priority to PCT/US03/39430 filed on Dec. 11, 2003 (Applicant—Qiagen GMBH).
Notice of Rejection issued Sep. 29, 2009 for JP 2004-565385, which claims priority to PCT/US03/39430 filed on Dec. 11, 2003 (Applicant—Qiagen GMBH).
Request for Examination filed Nov. 22, 2006 for JP 2004-565385, which claims priority to PCT/US03/39430 filed on Dec. 11, 2003 (Applicant—Qiagen GMBH).
International Search Report issued Aug. 23, 2004 for PCT/US03/39430 filed on Dec. 11, 2003 (Applicant—Qiagen GMBH).
Notice of Abandonment issued Feb. 13, 2008 for CA 2510587, which claims priority to PCT/US03/40364 filed on Dec. 19, 2003 (Applicant—Qiagen GMBH).
Reply to Rule 124(4) Communication filed Dec. 21, 2010 for EP 3799976, which claims priority to PCT/US03/40364 filed on Dec. 19, 2003 (Applicant—Qiagen GMBH).
Minutes of Oral Proceedings issued Oct. 18, 2010 for EP 3799976, which claims priority to PCT/US03/40364 filed on Dec. 19, 2003 (Applicant—Qiagen GMBH).
Brief Communication issued Sep. 10, 2010 for EP 3799976, which claims priority to PCT/US03/40364 filed on Dec. 19, 2003 (Applicant—Qiagen GMBH).
Requests including 1st-4th Auxiliary Requests filed Aug. 23, 2010 for EP 3799976, which claims priority to PCT/US03/40364 filed on Dec. 19, 2003 (Applicant—Qiagen GMBH).
Summons to Attend Oral Proceedings issued May 6, 2010 for EP 3799976, which claims priority to PCT/US03/40364 filed on Dec. 19, 2003 (Applicant—Qiagen GMBH).
Response to Art. 94(3) EPC Communication filed Aug. 13, 2009 for EP 3799976, which claims priority to PCT/US03/40364 filed on Dec. 19, 2003 (Applicant—Qiagen GMBH).
Art. 94(3) EPC Communication issued May 14, 2009 for EP 3799976, which claims priority to PCT/US03/40364 filed on Dec. 19, 2003 (Applicant—Qiagen GMBH).
Response to Art. 94(3) EPC Communication filed Jun. 2, 2008 for EP 3799976, which claims priority to PCT/US03/40364 filed on Dec. 19, 2003 (Applicant—Qiagen GMBH).
Art. 94(3) EPC Communication issued Apr. 18, 2008 for EP 3799976, which claims priority to PCT/US03/40364 filed on Dec. 19, 2003 (Applicant—Qiagen GMBH).
Response to Art. 96(2) EPC Communication filed Dec. 17, 2007 for EP 3799976, which claims priority to PCT/US03/40364 filed on Dec. 19, 2003 (Applicant.

Art. 96(2) EPC Communication issued Aug. 22, 2007 for EP 3799976, which claims priority to PCT/US03/40364 filed on Dec. 19, 2003 (Applicant—Qiagen GMBH).
Response to Art. 96(1) Communication filed Jun. 29, 2007 for EP 3799976, which claims priority to PCT/US03/40364 filed on Dec. 19, 2003 (Applicant—Qiagen GMBH).
Art. 96(1) EPC Communication issued May 7, 2007 for 3799976, which claims priority to PCT/US03/40364 filed on Dec. 19, 2003 (Applicant—Qiagen GMBH).
Supplementary EPO Search Report issued Apr. 18, 2007 for EP 3799976, which claims priority to PCT/US03/40364 filed on Dec. 19, 2003 (Applicant—Qiagen GMBH).
Claim Set filed Sep. 22, 2010 for EP 10178502, which claims priority to PCT/US03/40364 filed on Dec. 19, 2003 (Applicant—Qiagen GMBH).
Amendment and Response filed Jul. 21, 2010 for JP 2005510007, which claims priority to PCT/US03/40364 filed on Dec. 19, 2003 (Applicant—Qiagen GMBH).
Examination Report issued Mar. 23, 2010 for JP 2005510007, which claims priority to PCT/US03/40364 filed on Dec. 19, 2003 (Applicant—Qiagen GMBH).
Amendment and Response filed Feb. 26, 2010 for JP 2005510007, which claims priority to PCT/US03/40364 filed on Dec. 19, 2003 (Applicant—Qiagen GMBH).
Examination Report issued Nov. 4, 2009 for JP 2005510007, which claims priority to PCT/US03/40364 filed on Dec. 19, 2003 (Applicant—Qiagen GMBH).
Claim Set filed Feb. 26, 2010 for JP 2010042086, which claims priority to PCT/US03/40364 filed on Dec. 19, 2003 (Applicant—Qiagen GMBH).
International Search Report issued Apr. 4, 2005 for PCT/US03/40364 filed on Dec. 19, 2003 (Applicant—Qiagen GMBH).
Notice of Abandonment issued Feb. 4, 2008 for AU 2001268725, which claims priority to PCT/US01/20217 filed on Jun. 27, 2001 (Applicant—Qiagen GMBH).
Notice of Acceptance issued Jul. 20, 2006 for AU 2001268725, which claims priority to PCT/US01/20217 filed on Jun. 27, 2001 (Applicant—Qiagen GMBH).
Response to Examiner's First Report issued Jun. 23, 2006 for AU 2001268725, which claims priority to PCT/US01/20217 filed on Jun. 27, 2001 (Applicant—Qiagen GMBH).
Examination Report issued Jul. 18, 2005 for AU 2001268725, which claims priority to PCT/US01/20217 filed on Jun. 27, 2001 (Applicant—Qiagen GMBH).
Notification of Search Results issued May 5, 2004 for AU 2001268725, which claims priority to PCT/US01/20217 filed on Jun. 27, 2001 (Applicant—Qiagen GMBH).
Notice of Abandonment issued Aug. 22, 2007 for CA 2410951, which claims priority to PCT/US01/20217 filed on Jun. 27, 2001 (Applicant—Qiagen GMBH).
Notice of National Entry issued Jan. 14, 2003 for CA 2410951, which claims priority to PCT/US01/20217 filed on Jun. 27, 2001 (Applicant—Qiagen GMBH).
Expiry of Time Limit in which to file Notice of Opposition issued Aug. 22, 2007 for EP 1946712.5, which claims priority to PCT/US01/20217 filed on Jun. 27, 2001 (Applicant—Molecular Staging, Inc.).
Decision to Grant European Patent issued Sep. 21, 2006 for EP 1946712.5, which claims priority to PCT/US01/20217 filed on Jun. 27, 2001 (Applicant—Molecular Staging, Inc.).
Brief Communication re: Amendment issued Aug. 31, 2006 for EP 1946712.5, which claims priority to PCT/US01/20217filed on Jun. 27, 2001 (Applicant—Molecular Staging, Inc.).
Response to Communication under Rule 51(4) filed Aug. 18, 2006 for EP 1946712.5, which claims priority to PCT/US01/20217 filed on Jun. 27, 2001 (Applicant—Molecular Staging, Inc.).
Communication under Rule 51(4) issued Apr. 19, 2006 for EP 1946712.5, which claims priority to PCT/US01/20217 filed on Jun. 27, 2001 (Applicant—Molecular Staging, Inc.).
Response to Invitation pursuant to Article 96(2) EPC filed Feb. 6, 2006 for EP 1946712.5, which claims priority to PCT/US01/20217 filed on Jun. 27, 2001 (Applicant—Molecular Staging, Inc.).

Communication pursuant to Article 115(2) EPC issued Jan. 9, 2006 for Ep 1946712.5, which claims priority to PCT/US01/20217 filed on Jun. 27, 2001 (Applicant—Molecular Staging, Inc.).
Transmittal of Third Party Observations issued Jan. 9, 2006 for EP 1946712.5, which claims priority to PCT/US01/20217 filed on Jun. 27, 2001 (Applicant—Molecular Staging, Inc.).
Observations by Third Party filed Dec. 22, 2005 for EP 1946712.5, which claims priority to PCT/US01/20217 filed on Jun. 27, 2001 (Applicant—Molecular Staging, Inc.).
Invitation pursuant to Article 96(2) and Rule 51(2) EPC issued Dec. 15, 2005 for EP 1946712.5, which claims priority to PCT/US01/20217 filed on Jun. 27, 2001 (Applicant—Molecular Staging, Inc.).
Brief Communication issued Dec. 6, 2005 for EP 1946712.5, which claims priority to PCT/US01/20217 filed on Jun. 27, 2001 (Applicant—Molecular Staging, Inc.).
Written Submissions with Requests filed Nov. 29, 2005 for EP 1946712.5, which claims priority to PCT/US01/20217 filed on Jun. 27, 2001 (Applicant—Molecular Staging, Inc.).
Result of Consultation issued Nov. 16, 2005 for EP 1946712.5, which claims priority to PCT/US01/20217 filed, on Jun. 27, 2001 (Applicant—Molecular Staging, Inc.).
Response to Summons to Attend Oral Proceedings filed Oct. 31, 2005 for EP 1946712.5, which claims priority to PCT/US01/20217 filed on Jun. 27, 2001 (Applicant—Molecular Staging, Inc.).
Summons to attend Oral Proceedings issued Jul. 1, 2005 for EP 1946712.5, which claims priority to PCT/US01/20217 filed on Jun. 27, 2001 (Applicant—Molecular Staging, Inc.).
Response to Office Action filed Dec. 20, 2004 for EP 1946712.5, which claims priority to PCT/US01/20217 filed on Jun. 27, 2001 (Applicant—Molecular Staging, Inc.).
Communication pursuant to Article 96(2) EPC issued Nov. 11, 2004 for EP 1946712.5, which claims priority to PCTAJS01/20217 filed on Jun. 27, 2001 (Applicant—Molecular Staging, Inc.).
Acknowledgment of Receipt of Third Party Observations issued Oct. 29, 2004 for EP 1946712.5, which claims priority to PCT/US01/20217 filed on Jun. 27, 2001 (Applicant—Molecular Staging, Inc.).
Communication pursuant to Article 115(2) EPC issued Oct. 29, 2004 for EP 1946712.5, which claims priority to PCT/US01/20217 filed on Jun. 27, 2001 (Applicant—Molecular Staging, Inc.).
Observations by Third Party filed Oct. 19, 2004 for 1946712.5, which claims priority to PCT/US01/20217 filed on Jun. 27, 2001 (Applicant—Molecular Staging, Inc.).
Response to Communication pursuant to Article 96(2) EPC filed Jul. 27, 2004 for EP 1946712.5, which claims priority to PCT/US01/20217 filed on Jun. 27, 2001 (Applicant—Molecular Staging, Inc.).
Communication pursuant to Article 96(2) EPC issued Mar. 19, 2004 for EP 1946712.5, which claims priority to PCT/US01/20217 filed on Jun. 27, 2001 (Applicant—Molecular Staging, Inc.).
Response to Communication pursuant to Article 96(2) EPC filed Jan. 30, 2004 for EP 1946712.5, which claims priority to PCT/US01/20217 filed on Jun. 27, 2001 (Applicant—Molecular Staging, Inc.).
Communication pursuant to Article 96(2) EPC issued Jul. 24, 2003 for EP 1946712.5, which claims priority to PCT/US01/20217 filed on Jun. 27, 2001 (Applicant—Molecular Staging, Inc.).
International Preliminary Examination Report issued Nov. 12, 2004 for PCT/US01/20217 filed on Jun. 27, 2001 (Applicant—Molecular Staging, Inc.).
Written Opinion issued Oct. 23, 2003 for PCT/US01/20217 filed on Jun. 27, 2001 (Applicant—Molecular Staging, Inc.).
International Search Report issued Dec. 20, 2002 for PCT/US01/20217 filed on Jun. 27, 2001 (Applicant—Molecular Staging, Inc.).
International Preliminary Examination Report issued Dec. 28, 2004 for PCT/US00/16130 filed on Jun. 12, 2000 (Applicant—Molecular Staging, Inc.).
International Search Report issued Mar. 13, 2003 for PCT/US00/16130 filed on Jun. 12, 2000 (Applicant—Molecular Staging, Inc.).
Acknowledgment of withdrawal of patent application issued Mar. 9, 2005 for EP 2705674.6, which claims priority to PCT/US02/00005 filed on Jan. 4, 2002 (Applicant—Molecular Staging, Inc.).
International Preliminary Examination Report issued May 12, 2003 for PCT/US02/00005 filed on Jan. 4, 2002 (Applicant—Molecular Staging, Inc.).

International Search Report issued Feb. 19, 2003 for PCT/US02/00005 filed on Jan. 4, 2002 (Applicant—Molecular Staging, Inc.).
Acknowledgement of Withdrawal issued Oct. 6, 2003 for EP 980827, which claims priority to PCT/US00/32370 filed on Nov. 28, 2000 (Applicant—Molecular Staging, Inc.).
Withdrawal of Application issued Sep. 10, 2003 for EP 980827, which claims priority to PCT/US00/32370 filed on Nov. 28, 2000 (Applicant—Molecular Staging, Inc.).
Response to Communication Pursuant to Rules 109 and 110 EPC filed Oct. 16, 2001 for EP 980827, which claims priority to PCT/US00/32370 filed on Nov. 28, 2000 (Applicant—Molecular Staging, Inc.).
International Search Report issued Apr. 12, 2000 for PCT/US00/32370 filed on Nov. 28, 2000 (Applicant—Molecular Staging, Inc.).
International Preliminary Examination Report issued Oct. 15, 2004 for PCT/US01/11151 filed on Apr. 5, 2001 (Applicant—Molecular Staging, Inc.).
International Search Report issued Oct. 18, 2002 for PCT/US01/11151 filed on Apr. 5, 2001 (Applicant—Molecular Staging, Inc.).
International Preliminary Examination Report issued Mar. 9, 2006 for PCT/US02/19443 filed on Jun. 19, 2002 (Applicant—Molecular Staging, Inc.).
International Search Report issued Oct. 10, 2003 for PCT/US02/19443 filed on Jun. 19, 2002 (Applicant—Molecular Staging, Inc.).
International Preliminary Examination Report issued Oct. 6, 2004 for PCT/US02/27097 filed on Aug. 14, 2002 (Applicant—Molecular Staging, Inc.).
International Search Report issued Jan. 29, 2003 for PCT/US02/27097 filed on Aug. 14, 2002 (Applicant—Molecular Staging, Inc.).
Response to Art. 94(3) EPC Communication filed Jan. 4, 2011 for EP 7118804.9 filed on Oct. 18, 2007 (Applicant—Qiagen GMBH).
Art. 94(3) EPC Communication issued Aug. 26, 2010 for EP 7118804.9 filed on Oct. 18, 2007 (Applicant—Qiagen GMBH).
Response to Art. 94(3) EPC Communication filed Sep. 29, 2008 for EP 7118804.9 filed on Oct. 18, 2007 (Applicant—Qiagen GMBH).
Art. 94(3) EPC Communication issued Aug. 7, 2008 for EP 7118804.9 filed on Oct. 18, 2007 (Applicant—Qiagen GMBH).
European Search Report issued Feb. 15, 2008 for EP 7118804.9 filed on Oct. 18, 2007 (Applicant—Qiagen GMBH).
Request for Examination filed Jul. 27, 2010 for JP 2007-276942 filed on Oct. 24, 2007 (Applicant—Qiagen GmbH).
Notice of Sealing issued Oct. 10, 2002 for AU 97915/98, which claims priority to PCT/US98/21177 filed on Oct. 8, 1998 (Applicant—Yale University).
Notice of Acceptance issued May 20, 2002 for AU 97915/98, which claims priority to PCT/US98/21177 filed on Oct. 8, 1998 (Applicant—Yale University).
Request to Amend a Complete Specification filed Mar. 27, 2002 for AU 97915/98, which claims priority to PCT/US98/21177 filed on Oct. 8, 1998 (Applicant—Yale University).
First Statement of Proposed Amendments filed Mar. 27, 2002 for AU 97915/98, which claims priority to PCT/US98/21177 filed on Oct. 8, 1998 (Applicant—Yale University).
Examiner's First Report issued May 25, 2001 for AU 97915/98, which claims priority to PCT/US98/21177 filed on Oct. 8, 1998 (Applicant—Yale University).
Notice of Abandonment issued Dec. 4, 2007 for CA 2308004, which claims priority to PCT/US98/21177 filed on Oct. 8, 1998 (Applicant—Yale University).
Notice of Acceptance issued Oct. 16, 2006 for CA 2308004, which claims priority to PCT/US98/21177filed on Oct. 8, 1998 (Applicant—Yale University).
Response to Examination filed Dec. 23, 2004 for CA 2308004, which claims priority to PCT/US98/21177 filed on Oct. 8, 1998 (Applicant—Yale University).
Examination Report issued Jun. 30, 2004 for CA 2308004, which claims priority to PCT/US98/21177 filed on Oct. 8, 1998 (Applicant—Yale University).
Voluntary Amendments filed Oct. 12, 2000 for CA 2308004, which claims priority to PCT/US98/21177 filed on Oct. 8, 1998 (Applicant—Yale University).

Communication regarding Expiry of Opposition Time Period issued Nov. 5, 2008 for EP 98952147.1, which claims priority to PCT/US98/21177 filed on Oct. 8, 1998 (Applicant—Yale University).
Decision to Grant issued Dec. 6, 2007 for EP 98952147.1, which claims priority to PCT/US98/21177 filed on Oct. 8, 1998 (Applicant—Yale University).
Brief Communication re: Request for Amendment of Application issued Nov. 2, 2007 for EP 98952147.1, which claims priority to PCT/US98/21177 filed on Oct. 8, 1998 (Applicant—Yale University).
Response to Communication under Rule 51(4) filed Oct. 5, 2007 for EP 98952147.1, which claims priority to PCT/US98/21177 filed on Oct. 8, 1998 (Applicant—Yale University).
Communication under Rule 51(4) issued Jun. 6, 2007 for EP 98952147.1, which claims priority to PCT/US98/21177 filed on Oct. 8, 1998 (Applicant—Yale University).
Response to Article 96(2) EPC and Rule 51(2) EPC Communication filed May 14, 2007 for EP 98952147.1, which claims priority to PCT/US98/21177 filed on Oct. 8, 1998 (Applicant—Yale University).
Invitation pursuant to Article 96(2) EPC and Rule 51(2) EPVC issued Apr. 16, 2007 for EP 98952147.1, which claims priority to PCT/US98/21177 filed on Oct. 8, 1998 (Applicant—Yale University).
Response to Examination Report filed Mar. 13, 2007 for EP 98952147.1, which claims priority to PCT/US98/21177 filed on Oct. 8, 1998 (Applicant—Yale University).
Invitation pursuant to Article 96(2) EPC and Rule 51(2) EPC issued Dec. 29, 2006 for 98952147.1, which claims priority to PCT/US98/21177 filed on Oct. 8, 1998 (Applicant—Yale University).
Response to Communication pursuant to Article 96(2) EPC filed Mar. 6, 2006 for EP 98952147.1, which claims priority to PCT/US98/21177 filed on Oct. 8, 1998 (Applicant—Yale University).
Examination Report issued Sep. 21, 2005 for EP 98952147.1, which claims priority to PCT/US98/21177 filed on Oct. 8, 1998 (Applicant—Yale University).
Favorable Decision regarding Notice of Appeal issued Feb. 3, 2009 for JP 2000-515033, which claims priority to PCT/US98/21177 filed on Oct. 8, 1998 (Applicant—Yale University).
Amendment and Response to Official Action filed Dec. 22, 2008 for JP 2000-515033, which claims priority to PCT/US98/21177 filed on Oct. 8, 1998 (Applicant—Yale University).
Official Action issued Dec. 2, 2008 for JP 2000-515033, which claims priority to PCT/US98/21177 filed on Oct. 8, 1998 (Applicant—Yale University).
Argument to Written Communication filed Apr. 2, 1008 for JP2000-515033, which claims priority to PCT/US98/21177 filed on Oct. 8, 1998 (Applicant—Yale University).
Report Concerning Reconsideration before Appeal issued Oct. 2, 2007 for JP 2000-515033, which claims priority to PCT/US98/21177 filed on Oct. 8, 1998 (Applicant—Yale University).
Amendment and Response to Official Action filed Dec. 28, 2006 for JP 2000-515033, which claims priority to PCT/US98/21177 filed on Oct. 8, 1998 (Applicant—Yale University).
Final Rejection issued Sep. 2, 2005 for JP 2000-515033, which claims priority to PCT/US98/21177 filed on Oct. 8, 1998 (Applicant—Yale University).
Response to Examination filed Nov. 11, 2004 for JP 2000-515033, which claims priority to PCT/US98/21177 filed on Oct. 8, 1998 (Applicant—Yale University).
Examination Report issued May 7, 2004 for JP 2000-515033, which claims priority to PCT/US98/21177 filed on Oct. 8, 1998 (Applicant—Yale University).
International Preliminary Examination Report issued Dec. 10, 1999 for PCT/US98/21177 filed on Oct. 8, 1998 (Applicant—Yale University).
Response to Written Opinion issued Oct. 18, 1999 for PCT/US98/21177 filed on Oct. 8, 1998 (Applicant—Yale University).
Written Opinion issued Jul. 20, 1999 for PCT/US98/21177 filed on Oct. 8, 1998 (Applicant—Yale University).
International Search Report issued Mar. 10, 1999 for PCT/US98/21177 filed on Oct. 8, 1998 (Applicant—Yale University).

Noting of Loss of Rights (69(1) EPC) issued Apr. 1, 2004 for EP 99935725.4, which claims priority to PCT/US99/16373 filed on Jul. 20, 1999 (Applicant—Yale University).
Examination Report issued Aug. 13, 2003 for EP 99935725.4, which claims priority to PCT/US99/16373 filed on Jul. 20, 1999 (Applicant—Yale University).
International Preliminary Examination Report issued Sep. 19, 2000 for PCT/US99/16373 filed on Jul. 20, 1999 (Applicant—Yale University).
Response to Written Opinion filed Aug. 18, 2000 for PCT/US99/16373 filed on Jul. 20, 1999 (Applicant—Yale University).
Written Opinion issued Jun. 20, 2000 for PCT/US99/16373 filed on Jul. 20, 1999 (Applicant—Yale University).
International Search Report issued Dec. 2, 1999 for PCT/US99/16373 filed on Jul. 20, 1999 (Applicant—Yale University) Applicant -.
International Search Report issued 08/08/06 for PCT Application No. PCT/EP2006/002771 filed on Mar. 27, 2006 (Applicant—Qiagen GMBH).
Written Opinion of the International Search Authority issued Oct. 2, 2007 for PCT Application No. PCT/EP2006/002771 filed on Mar. 27, 2006 (Applicant—Qiagen GMBH).
International Preliminary Opinion on Patentability issued 10/03/07 for PCT Application No. PCT/EP2006/002771 filed on Mar. 27, 2006 (Applicant—Qiagen GMBH).
Communication from the European Examining Division issued Jul. 17, 2009 for EP Application No. EP2006723749 filed on Oct. 24, 2007 (Applicant—Qiagen GMBH).
Reply to Communication from European Examining Division filed Aug. 20, 2009 for EP Application No. EP2006723749 filed on Oct. 24, 2007 (Applicant—Qiagen GMBH).
Communication from the European Examining Division issued Oct. 29, 2009 for EP Application No. EP2006723749 filed on Oct. 24, 2007 (Applicant—Qiagen GMBH).
Reply to Communication from European Examining Division filed Nov. 24, 2009 for EP Application No. EP2006723749 filed on Oct. 24, 2007 (Applicant—Qiagen GMBH).
Communication from the European Examining Division issued Dec. 23, 2009 for EP Application No. EP2006723749 filed on Oct. 24, 2007 (Applicant—Qiagen GMBH).
Reply to Communication from European Examining Division filed Apr. 9, 2010 for EP Application No. EP2006723749 filed on Oct. 24, 2007 (Applicant—Qiagen GMBH).
English Translation of Granted Claims issued Sep. 22, 2010 for EP Application No. EP2006723749 filed on Oct. 24, 2007 (Applicant—Qiagen GMBH).
Decision to Grant European Patent issued Oct. 21, 2010 for EP Application No. EP2006723749 filed on Oct. 24, 2007 (Applicant—Qiagen GMBH).
International Preliminary Report on Patentability and Written Opinion issued on Apr. 8, 2008 for International App. No. PCT/EP2006/06622, filed on Sep. 11, 2006 (Applicant—Qiagen GMBH).
International Search Report issued on Apr. 13, 2007 for International App. No. PCT/EP2006/06622, filed on Sep. 11, 2006 (Applicant—Qiagen GMBH).
Reply to Communication filed on Jan. 4, 2011 for EP Application No. EP07118804 filed on Oct. 18, 2007 (Applicant—Qiagen GMBH).
EPO Communication issued on Aug. 26, 2010 for EP Application No. EP07118804 filed on Oct. 18, 2007 (Applicant—Qiagen GMBH).
Reply to Communication from European Examining Division filed on Sep. 29, 2008 for EP Application No. EP07118804 filed on Oct. 18, 2007 (Applicant—Qiagen GMBH).
EPO Communication issued on Aug. 7, 2008 for EP Application No. EP07118804 filed on Oct. 18, 2007 (Applicant—Qiagen GMBH).
European Search Report issued on Feb. 15, 2008 for EP Application No. EP07118804 filed on Oct. 18, 2007 (Applicant—Qiagen GMBH).
Carninci et al., Thermostabilization and thermoactivation of thermolabile enzymes by trehalose and its application for the synthesis of full length cDNA, PNAS vol. 95, pp. 520-524, 1998.
Kyle et al., A microfluorometric method for quantifying RNA and DNA in terrestrial insects, Journal of Insect Science, 3:1, pp. 1-7, 2003.
Sanyal, et al., An effective method of completely removing contaminating genomic DNA from an RNA sample to be used for PCR, Molecular Biotechnology, vol. 8, No. 2, pp. 135-137, 1997.
Bauer et al., Use of manganese in RT-PCR eliminates PCR artifacts resulting from DNase I digestion, Biotechniques. Jun. 1997;22(6):1128-32.
"Avoiding DNA contamination in RT-PCR" available at http://www.ambion.com/techlib/tb/tb_176.html, Oct. 3, 2004.
"Methods to remove DNA contamination from RNA samples" available at http://www.ambion.com/techlib/tb/tb_181.html, Oct. 30, 2004.
Stratagene Catalog: RT-PCR Systems and Kits, Stratagene Catalog, 1999 pp. 154-155.
International Search Report issued Aug. 8, 2006 for PCT Application No. PCT/EP2006/002771.
Written Opinion of the International Search Authority issued Oct. 2, 2007 for PCT Application No. PCT/EP2006/002771.
International Preliminary Opinion on Patentability issued Oct. 3, 2007 for PCT Application No. PCT/EP2006/002771.
Communication from the European Examining Division issued Jul. 17, 2009 for EP Application No. EP2006723749.
Reply to Communication from European Examining Division filed Aug. 20, 2009 for EP Application No. EP2006723749.
Communication from the European Examining Division issued Oct. 29, 2009 for EP Application No. EP2006723749.
Reply to Communication from European Examining Division filed Nov. 24, 2009 for EP Application No. EP2006723749.
Communication from the European Examining Division issued Dec. 23, 2009 for EP Application No. EP2006723749.
Reply to Communication from European Examining Division filed Apr. 9, 2010 for EP Application No. EP2006723749.
English Translation of Granted Claims issued Sep. 22, 2010 for EP Application No. EP2006723749.
Decision to Grant European Patent issued Oct. 21, 2010 for EP Application No. EP2006723749.

* cited by examiner

REVERSE TRANSCRIPTION AND AMPLIFICATION OF RNA WITH SIMULTANEOUS DEGRADATION OF DNA

CROSS REFERENCE TO RELATED APPLICATIONS

The present application is a National Phase Application of International Application No. PCT/EP2006/002771, filed Mar. 27, 2006, which claims priority to European Patent Application No. 05007157.0 filed Apr. 1, 2005, which applications are incorporated herein fully by this reference.

The present invention relates to a method for the treatment of RNA, in particular an RNA reaction method, as well as kits for performing an RNA reaction method according to the invention.

Many techniques in molecular biology lead to the analysis of ribonucleic acids (RNA). In order to be able to analyse RNA it must be purified of all inhibitory and contaminating substances. Thus, for example, contamination with genomic deoxyribonucleic acid (DNA) can have an inhibitory effect or lead to false positive results. A number of techniques of molecular RNA analysis begin with the reverse transcription of RNA into cDNA. cDNA is very similar to or even identical to genomic DNA in both structure and sequence. Therefore contamination by genomic DNA can lead to false results if cDNA is to be analysed (e.g. photometric determination of cDNA quantities or its quantification by PCR).

In order to be able to analyse RNA with certainty it is therefore necessary either to separate all other distorting nucleic acids, for example genomic DNA, from the RNA before a corresponding analysis, or to degrade them into their individual components. A separation method used for some time for DNA and RNA is the so-called density gradient centrifugation. Standard substances for density gradient centrifugation are caesium chloride (CsCl) and saccharose. In the case of CsCl a density gradient is established in the equilibrium state during centrifugation dependent upon, for example, the density of the starting solution, in which each macromolecule is aligned in the zone corresponding to its intrinsic density in the gradient. In order to visualise the nucleic acid bands established after centrifugation in the centrifugation vessel ethidium bromide is added to the CsCl solution, which is incorporated into the nucleic acid and which fluoresces in UV light. This method enables the reliable separation of individual DNA fragments which are otherwise very difficult to distinguish from one another owing to the close sedimentation rates of these fragments. In CsCl density gradient centrifugation gradients with density values between 1.0 and 1.9 g/ml are normally used. Since the buoyant density of RNA is normally greater than 1.9 g/ml, in an equilibrium centrifugation (also called isopycnic centrifugation) RNA settles to the bottom of the sample vessel in a gradient whose upper density limit lies at 1.9 g/ml, whereas all other types of molecule (including DNA) form respective bands within the gradient. Thus, corresponding separation operation leads to a good separation of RNA and DNA. However, the density gradient centrifugation method is relatively expensive owing to the chemicals used, very elaborate in apparatus and also very time consuming (in most rotors long centrifugation runs of up to 2 days are necessary until an equilibrium has been established in a conventional CsCl gradient).

Therefore a made has been made to the isolation of RNA whereby either during or after RNA preparation a DNase or several DNases is/are added to the experimental batch in order to degrade DNA contamination enzymatically. Systems (so-called "kits") for this purpose have been marketed by the company QIAGEN, Hilden, Germany under the name "RNeasy Micro Kit" and "RNeasy Fibrous Tissue Kit" and by the company Promega, Madison/WI, USA, under the name "SV Total RNA Isolation System". However, these RNA preparation methods do not lead to the isolation of pure RNA. The RNA isolated is present rather more as a material that is contaminated to different extents with genomic DNA, salts, inhibitors, etc. The level of purity achievable with the above-named kits may indeed be adequate for many applications, but this is not the case for a number of other areas of application (e.g. RT-PCR).

A further method for RNA purification is also used in which chromatographical methods are employed (e.g. ion exchange chromatography, oligo-dT chromatography) in order to enrich RNA further and to reduce the amount of DNA. However, it is not possible to purify ribosomal RNA with this method.

Finally, US patent application no. 20020042052 describes further a method for the removal of nucleic acid impurities from a batch for amplification reactions. Here a thermolabile DNase is used which always degrades unwanted double-stranded DNA in the amplification batch prior to the actual amplification reaction. Owing to its thermolability, the DNase used is irreversibly deactivated at the latest during the first temperature increase to above 90° C. during the PCR reaction. The PCR reaction can only then be commenced when the DNase reaction is concluded. A simultaneity of the DNA degradation reaction and an RNA reaction is thus not suggested by the method known from the cited American published specification.

Also, all these more recent methods are, however, in part time consuming, cost intensive and can possibly lead to cross-contamination during the simultaneous processing of several RNA preparations. Furthermore it is also the case with the previously known methods described above that DNA degradation does not take place concurrently with the RNA reaction or RNA analysis, but the DNA degradation is always carried out prior to the actual RNA reaction or RNA analysis.

Thus, the problem underlying the present invention is to provide a method for RNA analysis that does not have the disadvantages of the known methods described above. The new method has to be cost effective and less time consuming and keep the expenditure on apparatus within limits.

The invention solves this problem by the method according to independent Claim 1 and a kit according to the independent Claim 13. Further advantageous embodiments, aspects and details of the invention are provided by the dependent claims, the description, the examples and the figures.

The present invention thus relates to an RNA reaction method, characterised in that an RNA reaction and a degradation of double-stranded DNA present takes place in the same vessel, whereby the degradation of the double-stranded DNA is carried out by an enzyme with DNA double-strand-specific endonuclease activity. The RNA reaction and the degradation of double-stranded DNA present preferably takes place at the same time. This has the considerable advantage that it is no longer necessary to wait with the start of a RNA reaction until the unwanted double-stranded DNA present in the reaction batch has been fully degraded or at least so far degraded that it no longer interferes with the RNA reaction or the associated analysis reaction. Also, by means of the method according to the invention the risk that impurities are introduced into the reaction batch by frequent opening of the reaction vessel is reduced Also, in the method according to the invention the RNA reaction on the one hand and the DNA degradation on the other can be carried out at the same temperature. The temperature can thereby lie, for example, in the range from 10 to 80° C., preferably 20 to 70° C., in particular 20 to 60° C.

Thus for the first time the invention combines DNA decontamination of the sample with the RNA reaction in a simultaneous process, that is, the DNA decontamination on the one hand and the RNA reaction or the RNA analysis on the other run sequentially or concurrently or in parallel in one and the same reaction vessel. Typical RNA reactions are, for example, reverse transcription, 1 step RT-PCR (reverse transcription polymerase chain reaction in one step) or tagging reactions of RNA, but are not limited to these.

The present invention thus ensures a degradation of undesirable double-stranded DNA (e.g. genomic DNA (gDNA), linear or circular DNA, e.g. plasmid DNA) at the same time as reactions that contain RNA as analyte (e.g. reverse transcription, see above). The degradation of the double-stranded DNA takes place within the reaction that contains RNA as analyte by means of an enzyme with DNA double-strand-specific endonuclease activity. This enzyme is a deoxyribonuclease (DNase) or several DNases that specifically cleaves or cleave completely or at least partially by endonucleolytic hydrolysis DNA present as an intra- or intermolecular double strand. Furthermore, these DNases are characterised in that a cleavage of DNA single strands and RNA single strands and also RNA and DNA that occur as RNA-DNA hybrids does not take place, or only to a very small extent. With this invention it is possible for the first time for a double-strand-specific DNase to be used simultaneously for the degradation of double-stranded DNA in the presence of, for example, a cDNA synthesis reaction in which an RNA is transcribed into single-stranded DNA, whereby the single-stranded cDNA just formed in the synthesis process is degraded only very slightly or not at all. The DNA double-strand-specific endonucleases that may be used according to the invention can be thermostable or thermolabile.

As previously mentioned above, the present invention relates to the combination of reduction in dsDNA contamination on the one hand and RNA reactions on the other in a simultaneous process. Important thereby are the reaction conditions that equally allow DNA degradation to take place as well as also the reaction with the RNA, whereby the dsDNA decontamination is carried out, for example, with a double-strand-specific DNase.

A "DNA contamination" in an RNA isolate is defined as any double-stranded deoxyribonucleic acid molecule which can be of different origin and occurs together with the RNA in the same reaction vessel as undesired molecule. Double-strandedness of DNA can also occur when a single-stranded DNA is present folded back through self-hybridisation and thus is present double-stranded at least for a time.

The double-stranded DNA (dsDNA) can originate from the original biological material from which the RNA has been also isolated. This can be nuclear, plastidal or mitochondrial in nature. The dsDNA can be also transferred to the original biological material from an external source by biological means, be it by infection, transformation, fusion, incorporation or similar and can thus be, for example, of viral, prokaryotic or eukaryotic origin. In addition, the DNA can also be transferred to the original biological material by unnatural means such as, for example, electroporation, transformation, transfection or other techniques. It can be genomic DNA, plasmid DNA, doubles-stranded oligonucleotides (such as, for example, primer-dimers) or other forms of double-stranded DNA. Moreover, the double-stranded DNA can also be introduced into the RNA preparation either during or after RNA isolation.

Defined as "RNA reaction" are, for example:
(1) any form of change to the RNA such as, for example, degradation, tagging, extension, modification or similar. The RNA can be present thereby as single-stranded, double-stranded or as hybrid molecule (e.g. RNA-DNA hybrid);
where degradation is concerned it is preferably a specific degradation in which RNA is degraded selectively by, for example, ribozyme, RNase H and/or siRNA. An RNase H-enzyme obtained, for example, by mutation or chemical modification can also be used as RNase H;
(2) any form of conversion in which RNA is used as template for polymerase reactions such as, for example, (a) reverse transcription or (b) transcription by RNA polymerases or similar;
in respect of (a): the reverse transcription can be carried out by mutated or non-mutated RNA-dependent DNA polymerases such as, for example, reverse transcriptases from viruses, retrotransposons, bacteria, etc. These can have RNase H activity, or reverse transcriptases can be used that are so mutated that the RNase H activity of the reverse transcriptase was restricted or is not present (e.g. MMLV-RT RNase H$^-$). RNA-dependent DNA synthesis (reverse transcription) can also be carried by enzymes that show altered nucleic acid dependency through mutation or modified reaction conditions and thus obtain the function of the RNA-dependent DNA polymerase. Cited here as example is Tth-DNA polymerase, which is DNA-dependent, and by using modified reaction conditions RNA can also be used as matrix.
In respect of (b): an RNA polymerase reaction starting from RNA as matrix can be carried out with mutated and non-mutated RNA-dependent RNA polymerases from, for example, viruses, prokaryotes or eukaryotes. RNA-dependent RNA syntheses can also be carried out with enzymes that have a changed nucleic acid dependency through mutation or modified reaction conditions and thus obtain the function of the RNA-dependent RNA polymerase. Cited here as example is an RNA amplification method that uses a T7-RNA polymerase and RNA as matrix (EP 1 056 884);
(3) any form of conversion in which the RNA functions as catalyst such as, for example, ribozymes, etc.;
(4) any form of binding reaction. Different binding partners can be involved in the binding reaction whereby at least one partner is RNA. The following binding reactions are feasible such as, for example, RNA-RNA, RNA-DNA, RNA-PNA (known most widely as hybridisation), RNA antibody reactions, RNA aptamer reactions, recognition reactions of RNA with other molecules such as, for example, antibiotics or similar;
(5) any form of composite reactions in which the above-mentioned reactions (1) to (4) are a component of the overall reaction such as, for example, linear RNA amplification reactions (e.g. Eberwine, epiclones, Nugen), exponential RNA amplification methods (e.g. NASBA, TMA) or other amplification methods (e.g. SAGE, RT-PCR, RCA).

When in respect of the present invention discussion relates to RNA as "reaction participant" or of an "RNA reaction method", an "RNA reaction" or an "RNA analysis", this then means that the RNA is indeed involved in a respective reaction or analysis but must not necessarily be changed. Also, in accordance with the present invention the RNA is called a "reaction participant" in reactions from which RNA is recovered unchanged (e.g. when the RNA is used as catalyst or matrix), or when discussion refers to an "RNA reaction method", an RNA reaction" or an "RNA analysis".

If in connection with the present invention use is made of "at the same time" or simultaneity", "in parallel", "simultaneous" or similar it is to be understood that a dsDNA degradation and the RNA reaction takes place in the same reaction vessel. Degradation of the dsDNA contamination and the RNA reaction are thus carried out at the same time and in the one and the same reaction batch. Simultaneity is meant to express that the RNA reaction and a degradation of the dsDNA contamination takes place at the same time in the same reaction vessel and under the same reaction conditions.

It is also advantageous in the method according to the invention, in particular opposite the method known from US 20020042052, that the method according to the invention can take place at a uniform temperature, that is that the RNA reaction and a dsDNA degradation can take place at the same temperature. In addition, it is also beneficial opposite the method known from US 20020042052 that in the method according to the invention it is not necessary to open the reaction vessel again after the dsDNA degradation with DNase and to add a new enzyme (that would possible be irreversibly damaged by warming to over 90° C.) as in that way unnecessary contamination can be avoided.

According to the present invention the RNA reaction is limited by the reaction conditions which not only determine the RNA reaction, but simultaneously should also allow the degradation of the dsDNA contamination. This does not mean that optimal conditions are set respectively for the reaction of the RNA and for degradation of the dsDNA, but the conditions for the RNA reaction and a degradation of the DNA can throughout be adapted to one another. The present invention makes it possible for the first time for an RNA reaction and degradation of dsDNA to take place at the same time in the one and the same reaction vessel.

A "deoxyribonuclease", or abbreviated "DNase", is defined here as an enzyme that specifically completely or at least partially cleaves (degrades) by endonucleolytic hydrolysis DNA present as a intra- or intermolecular double strand, that is an enzyme with DNA double-strand-specific DNA endonuclease activity. This DNase is thus characterised in that a degradation or cleavage of RNA single strands and of DNA single strands and also of a RNA or DNA that is present as RNA-DNA hybrid does not take place or only to a negligibly small extent. The DNases within the meaning of the present invention are either sequence-specific or cleave the dsDNA non-specifically. Both variants can be used within the context of the present invention. It is likewise possible to use thermolabile and/or thermostable DNases. Thus it is clear to the appropriate person skilled in the art in the light of the respective RNA reaction or also of the respective follow-up reaction which enzyme is suitable.

By a "degradation" of the dsDNA it is to be understood that the degradation process progresses so far in every case that the DNA shows only a slight or no a disruptive effect on the RNA reaction(s) or the subsequent applications. A degradation can, but need not necessarily, mean a complete disintegration of double-stranded DNA into its individual components (nucleotides). Within the meaning of the invention the degradation of the dsDNA occurs at least partially at the same time as the RNA reaction.

Figure 2:
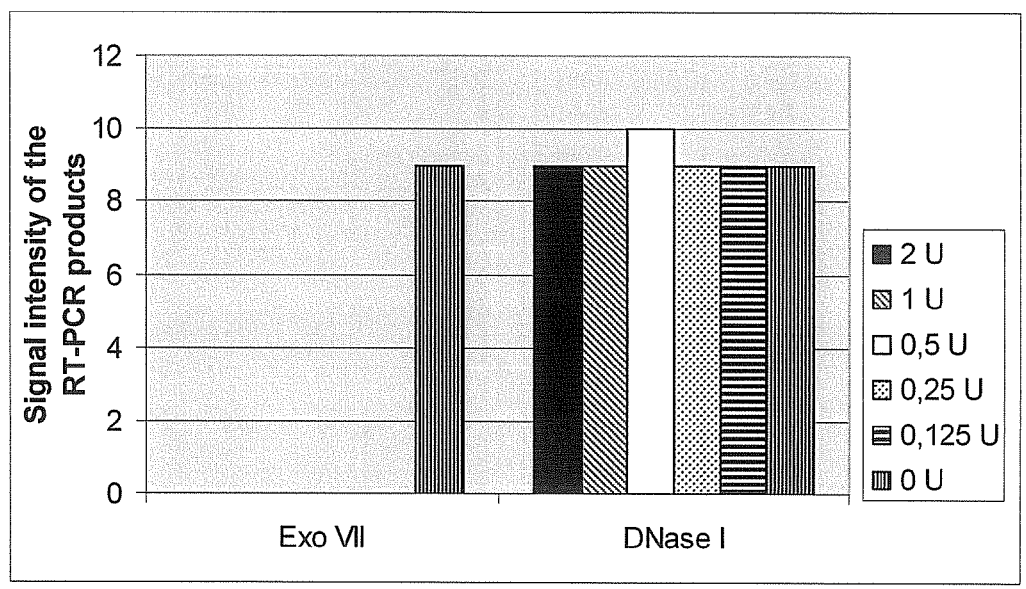
Figure 3:
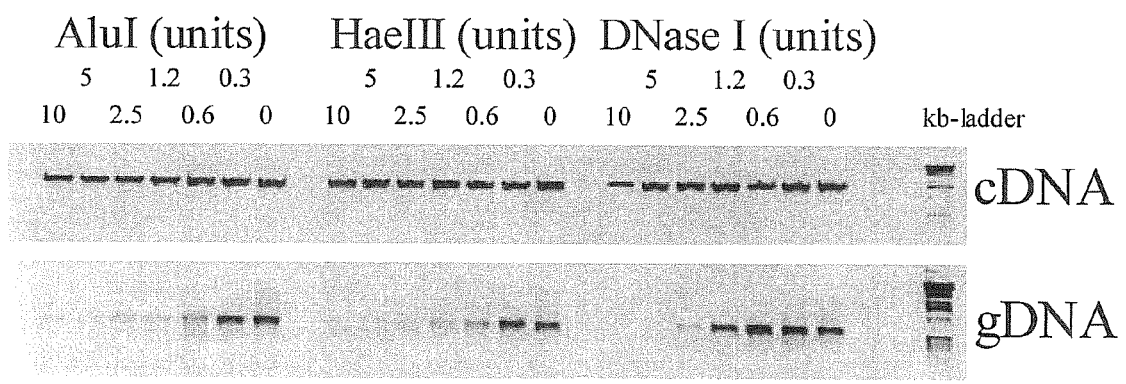
Figure 4:
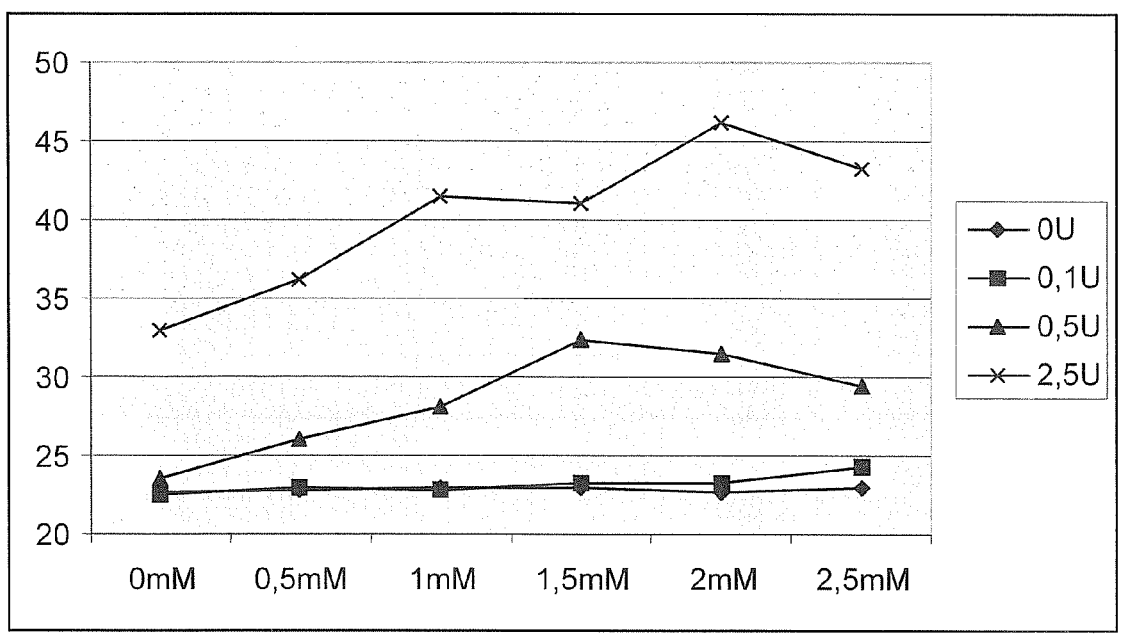
Figure 5:
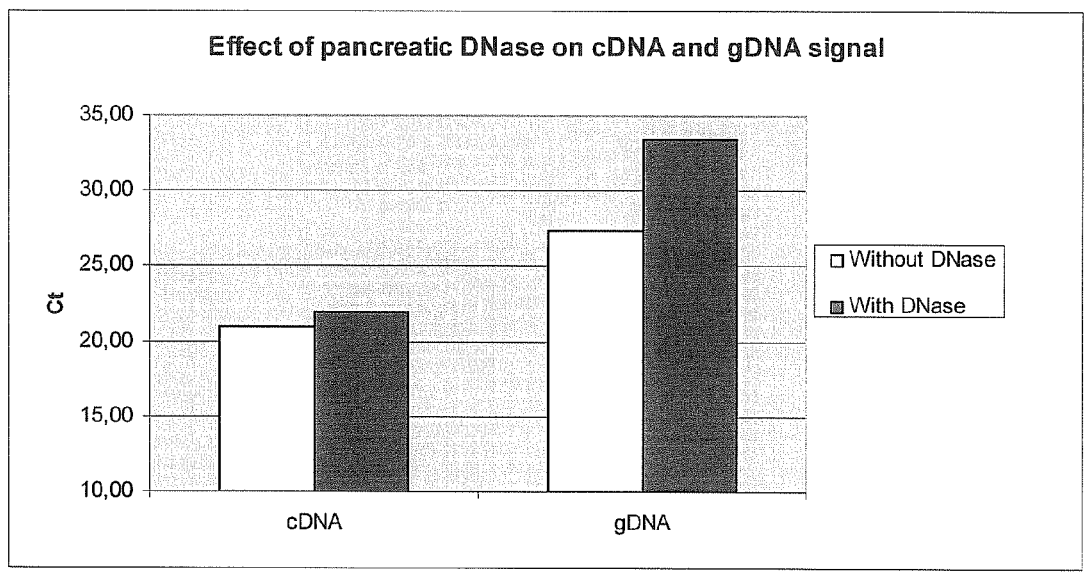

The diagrams show:

FIG. 1 a photo of an agarose gel which shows the result of an electrophoresis according to Example 1;

FIG. 2 a bar chart from which the results of an experiment on the possible effect of the reverse transcriptase reaction by various nucleases are seen (Example 2);

FIG. 3 a photo of an agarose gel which shows the result of an electrophoresis according to Example 3;

FIG. 4 a diagram which shows the results listed in Table 1 in graphical form; and FIG. 5 a bar chart which shows the effect of pancreatic DNase I on a cDNA and gDNA signal according to Example 7.

The following enzymes can be used for the degradation of double-stranded DNA, in particular in reverse transcriptase reactions:

1) sequence-independent (sequence-non-specific) endonucleases: these endonucleases can be a native enzyme (isolate from an organism) or prepared from genetically modified organisms (GMOs) or mutants of these enzymes. An example of a sequence-independent endonuclease is DNase I, which according to the invention is particularly preferred for the degradation of dsDNA;

2) sequence-specific endonucleases: these endonucleases can be a native enzyme (isolate from an organism) or prepared from genetically modified organisms (GMOs) or mutants of these enzymes. Examples of sequence-specific endonucleases are the enzymes Alu I or Hae III. Mixtures of sequence-specific endonucleases can also be used.

3) Combinations of sequence-specific endonucleases and sequence non-specific endonuclease.

The endonucleases are generally used in such a manner that the reaction batch contains about 0.01 to about 100 U of enzyme activity, preferably about 0.05 to about 20 U, more preferably about 0.1 to about 10 U. According to international agreement, enzyme activity expressed as 1 U (unit, enzyme unit) corresponds to a) for sequence-non-specific DNA double-strand-specific endonucleases the amount of enzyme that is necessary to convert 1 µmol substrate per minute at 25° C. under optimal conditions, and b) for sequence-specific DNA double-strand-specific restriction endonucleases the amount of enzyme that is necessary to convert 1 µg Lambda-DNA per hour at 37° C. under optimal conditions.

In the case of an RT-PCR the degradation of the dsDNA is carried out in the presence of a reverse transcriptase. Suitable reverse transcriptases are, for example, reverse transcriptases from retroviruses such as, for example, HIV, AMV, MMLV, Omniscript® (QIAGEN GmbH), Sensiscript® (QIAGEN GmbH) etc., or also from retrotransposons. The reverse transcriptases can correspond to the original organism in their amino acid sequence, or they can also have deviations therefrom, for example, changes that lead to loss of RNase H activity, change the processivity or influence the thermostability of the enzyme. DNA polymerases which originally have little or no reverse transcriptase activity can also be used and can be used as reverse transcriptase through the use of suitable reaction conditions or through mutations (e.g. rTth polymerase).

The aqueous buffer solution in which the degradation dsDNA takes place in the presence of reverse transcriptase comprises at least:

1) a DNA double-strand-specific endonuclease (as described above);

2) a reverse transcriptase (as described above);

3) a buffer substance which buffers the pH value of the experimental batch;

4) a pH value between 6 and 10, particularly preferred between 7 and 9; and 5) divalent cations which support a reverse transcriptase reaction and the enzymatic degradation of genomic DNA such as, for example, $Mg^{2+}$ (in a concentration range between 0.1 and 50 mM), $Mn^{2+}$ (in a concentration range between 0.01 and 10 mM), or Ca$^{2+}$ (in a concentration range between 0.01 and 50 mM).

The reaction batch can also contain other components such as, for example, other enzymes, divalent cations or salts. A heat-stable DNA polymerase can thus also be present.

The reaction temperature can lie, for example, between 10 and 70° C., preferably between 15° C. and 60° C., most particularly preferred between 20° C. and 50° C.

The present invention relates further to a kit for performing a method according to any of claims 1 to 12, whereby the kit comprises at least one reverse transcriptase, a DNA double-strand-specific endonuclease and a reaction buffer for performing a method according to any of the claims 1 to 12 and a dsDNA degradation in one vessel. Preferably the kits are such for performing a cDNA synthesis or for undertaking a 1-step RT-PCR. If the kit serves the performing of a 1-step PCR it can additionally contain a heat-stable DNA polymerase.

The invention is described more closely in the following by means of the examples.

EXAMPLE 1

In each case 1 µg gDNA and 1 µg total-RNA from HeLa cells were mixed for use in a reverse transcriptase reaction. The reverse transcriptase reaction was carried out in an aqueous medium that contained an oligo-dT primer, dNTPs, an RNase inhibitor, a buffer (Buffer RT from the Omniscript RT Kit of QIAGEN GmbH, Hilden, Germany) for the reverse transcription and a reverse transcriptase (Omniscript®, trademark of QIAGEN GmbH, Hilden, Germany). In addition different double-strand-specific DNases were added:
(1) Alu I restriction endonuclease in an amount of 10 U (obtainable from Roche, Mannheim, Germany);
(2) Hae III restriction endonuclease in an amount of 10 U (Roche).
(3) RNase-free DNase I in an amount of 10 U (Roche);
(4) Alu I restriction endonuclease in an amount of 10 U (Roche) and Hae III restriction endonuclease in an amount of 10 U (Roche).

No DNase was added to an additional reaction batch. This batch served as control. The reaction mixture was incubated for one hour at 37° C. and then (A) analysed by PCR for cDNA degradation and (B) tested for RNA integrity and DNA degradation on an agarose gel (1.2%).

The result is shown in FIG. 1. The degradation of gDNA is recognisable with the use of the DNases AluI, Hae III, DNase I or with the mixture of the DNases Alu I and Hae III, whereby the integrity of the rRNA was not impaired. Likewise, it could be seen on the basis of the RT-PCR signals of the β-actin transcript that the presence of the DNases Alu I, Hae III, DNase I or the mixture of the DNases Alu I and Hae III lead to no change in signal intensity, which demonstrates that the DNases used did not impair the RT reaction.

EXAMPLE 2

Each time 1 ng total RNA from HeLa cells was mixed with 1 µg of a 0.2-9.5 kB RNA-ladder (Invitrogen) for use in a reverse transcriptase reaction. The reverse transcriptase reaction was carried out in an aqueous medium that contained an oligo-dT primer, dNTPs, RNase inhibitor, a buffer (Buffer RT from the Omniscript RT Kit of QIAGEN GmbH, Hilden, Germany) for the reverse transcription and a reverse transcriptase (Omniscript®, trade mark of QIAGEN GmbH, Hilden, Germany). In addition the DNA double-strand-specific-endonuclease DNase I (RNase-free DNase I) was added. Exonuclease VII ("Exo VII") was added to further batches.

The DNase I (from bovine pancreas; obtainable from Roche, Mannheim, Germany) and the exonuclease VII were used in different amounts. No nuclease was added to a further reaction batch. This batch served as positive control. The batch with exonuclease VII served as negative control. Exonuclease VII is not double-strand-specific and able to degrade single-stranded DNA. The respective reaction mixtures were incubated for one hour at 37° C. and then analysed by PCR for cDNA degradation. The whole β-actin transcript was amplified in the PCR.

The result is shown in FIG. 2. The DNase I led to no impairment of the reverse transcriptase reaction. This is clear opposite the positive control. DNase I shows a signal intensity for RT-PCR fragments which corresponds to the intensity of the positive control. Only the single-strand-specific nuclease exonuclease VII used as negative control led to a considerable degradation of the single-strand-cDNA, so that no RT-PCR specific signal could be found.

EXAMPLE 3

Each of 1 µg genomic DNA and 1 µg total-RNA from HeLa cells were mixed for use in a reverse transcriptase reaction. The reverse transcriptase reaction was carried out in an aqueous medium that contained an oligo-dT primer, dNTPs, an RNase inhibitor and a buffer (Buffer RT from the Omniscript RT Kit of QIAGEN GmbH, Hilden, Germany) for the reverse transcription. In addition different amounts of double-strand-specific nucleases were added:
(1) Alu I restriction endonuclease in an amount of 0-10 U (Roche, Mannheim, Germany);
(2) Hae III restriction endonuclease in an amount of 0-10 U (Roche, Mannheim, Germany); and
(3) RNase-free DNase I in an amount of 0-10 U (Roche, Mannheim, Germany).

Reverse transcriptase was added to one set of the batches in order to be able to investigate the influence of nucleases on the synthesis of single-stranded cDNA. No reverse transcriptase was added to a second set of batches in order to be able to follow the degradation of genomic DNA. The reaction mixtures were incubated for one hour at 37° C. and then analysed by PCR. In the batches in which cDNA synthesis was followed the complete cDNA of the β-actin transcript was amplified. In the batches in which the degradation of genomic DNA was followed a region from the 5'-end of the β-actin gene was amplified. Since the primer set spans an intron the genomic amplificate shows a size of >600 bp, whereas the amplificate of the cDNA has a size of ca. 200 bp.

The result is shown in FIG. 3. FIG. 3 shows a photo or a 1% agarose gel on whose tracks batches with different nuclease concentrations were investigated. It can be seen from FIG. 3 that the reverse transcription was not impaired by the presence of the nucleases tested, which can be recognised in that the cDNA bands for all of the three nucleases tested remain clearly visible at all concentrations, see the upper region of FIG. 3. In contrast it is equally clear that the use of nucleases leads to a more or less complete degradation of the genomic DNA used when a certain minimal amount of nuclease (5 U) is added, see lower region of FIG. 3.

EXAMPLE 4

Each time 150 ng total RNA from HeLa cells were mixed with 150 ng gDNA in order to carry out a DNase reaction under reverse transcriptase reaction conditions. The reaction was carried out in an aqueous medium that contained oligo-dT primer, dNTPs, an RNase inhibitor and a buffer (Buffer RT from the Omniscript RT Kit of QIAGEN GmbH, Hilden, Germany) for the reverse transcription. In addition 0; 0.1; 0.5; or 2.5 units double-strand-specific nuclease (RNase-free DNase I) were added to the batches. Also 0 mM, 0.5 mM, 1 mM, 1.5 mM, 2 mM or 2.5 mM magnesium chloride were added to the batches. No reverse transcriptase was added in order to investigate the DNase I activity under reverse transcriptase reaction conditions. The reaction mixtures were incubated for one hour at 37° C. The DNA degradation was then analysed by quantitative real-time PCR. For this 1 μl of the reaction mixture each time was used for the real-time PCR. A primer pair that amplified a 200 bp fragment from the 5'-end of the β-actin was used. The resulting amplificate was detected with SYBR green.

The result is shown in FIG. 4 and Table 1. The degradation of the genomic DNA was determined from the CT value and is dependent upon the amount of RNase-free DNase I used. The activity of RNase-free DNase I can be modulated by the addition of extra magnesium chloride when the highest CT values were obtained for 2.5 U DNase and 2 mM $MgCl_2$.

TABLE 1

| $MgCl_2$ | DNase I (0 U) CT cycle | DNase I (0.1 U) CT cycle | DNase I (0.5 U) CT cycle | DNase I (2.5 U) CT cycle |
|---|---|---|---|---|
| 0 mM | 22.7 | 22.5 | 23.5 | 32.9 |
| 0.5 mM | 22.8 | 22.9 | 26.1 | 36.2 |
| 1 mM | 22.9 | 22.8 | 28.1 | 41.5 |
| 1.5 mM | 22.9 | 23.3 | 32.3 | 41.1 |
| 2 mM | 22.6 | 23.3 | 31.4 | 46.2 |
| 2.5 mM | 22.9 | 24.3 | 29.4 | 43.2 |

EXAMPLE 5

Each time 150 ng total RNA from HeLa cells were mixed with 0 ng or 150 ng gDNA for use in a reverse transcriptase reaction. The reaction was carried out in an aqueous medium that contained an oligo-dT primer, dNTPs, RNase inhibitor and a buffer (Buffer RT from the Omniscript RT Kit of QIAGEN GmbH, Hilden, Germany) for the revere transcription. In addition, 2.5 units of double-strand-specific endonuclease (RNase-free DNase I) are added to a part of the batches. One set of the batches received a reverse transcriptase in order to be able to investigate the influence of the nucleases on the synthesis of single-stranded cDNA. No reverse transcriptase was added to a second batch in order to be able follow the degradation of the genomic DNA. The reaction mixtures were incubated for one hour at 37° C. The cDNA synthesis and the DNA degradation were then analysed by quantitative real time PCR. In each case 1 μl and 0.1 μl of the reverse transcriptase reaction were used for the real time PCR. A primer pair that amplified a 210 bp fragment from the 3'-end of the β-actin was used. The resulting amplificate was detected with SYBR green.

The result of this investigation was that the reverse transcription was not impaired by the presence of RNase-free DNase I. By use of RNase-free DNase I the genomic DNA was degraded more than 1000 times. At the same time the cDNA generated was not, or only insignificantly, digested. The result is collated in Table 2.

The DNase step can also be carried out in a very brief reaction before the actual RNA-modifying reaction, whereby, however, as in the above batches the DNase remains in the reaction mixture and is not removed from the system by heat inactivation or a purification step.

TABLE 2

| Transferred volumes | CT cycle 150 ng Hela DNA | Mean value | CT cycle 0 ng Hela DNA | Mean value |
|---|---|---|---|---|
| Without reverse transcription, without DNase 1 μl | 22.1 22.4 22.0 | 22.2 | 32.6 33.5 34.0 | 33.4 |
| Without reverse transcription, with DNase 1 μl | 32.9 31.8 31.8 | 32.2 | 34.0 35.2 31.3 | 33.5 |
| Without reverse transcription, without DNase 0.1 μl | 25.3 25.4 25.6 | 25.4 | 34.4 32.4 32.9 | 33.2 |
| Without reverse transcription, with DNase 0.1 μl | 34.3 33.8 33.9 | 34.0 | 32.6 31.5 33.1 | 32.4 |
| With reverse transcription, with DNase 1 μl | 13.3 13.5 13.4 | 13.4 | 13.4 13.3 13.5 | 13.4 |
| With reverse transcription, without DNase 1 μl | 13.6 13.9 13.8 | 13.8 | 13.8 13.5 13.7 | 13.7 |
| With reverse transcription, with DNase 0.1 μl | 16.3 16.5 16.6 | 16.5 | 15.9 16.4 16.7 | 16.3 |
| With reverse transcription, without DNase 0.1 μl | 16.0 16.5 16.3 | 16.3 | 16.2 16.6 16.6 | 16.5 |

EXAMPLE 6

Each time 10 μg to 1 μg total RNA from HeLa cells were mixed with identical amounts of gDNA for use in a reverse transcriptase reaction. The reaction was carried out in an aqueous medium that contained an oligo-dT primer, random octamers, dNTPs, RNase inhibitor and a buffer (gDNA Wipe-out Buffer and Quantiscript RT Buffer from the QuantiTecto Reverse Transcription Kit of QIAGEN GmbH, Hilden, Germany) for the reverse transcription. Also 2.5 units double-strand-specific endonuclease (RNase-free DNase I) were added to a part of the batches. Reverse transcriptase was added to one set of the batches in order to be able to investigate the influence of the nucleases on the synthesis of single-stranded cDNA. No reverse transcriptase was added to a second set of batches in order to be able to follow the degradation of genomic DNA. Before the actual cDNA synthesis the DNase step was carried out for 2 minutes at 37° C. Only then were the reaction mixtures incubated for 15 minutes in the presence of the reverse transcriptase at 37° C. Next, the cDNA synthesis and the DNA degradation analysed by quantitative real time PCR. In each case 1 μl of the reverse transcriptase reaction was used for the real time PCR. A QuantiTect Gene Expression Assay (QIAGEN GmbH, Hilden, Germany) was used for the Gen RPSLA, together with the QuantiTect Probe PCR Kit (also from QIAGEN), which contains all necessary reaction components such as HotStar Taq DNA Polymerase (QIAGEN), reaction buffer and dNTPs. The HotStar Taq DNA Polymerase was reactivated for 15 minutes at 95° C., after which the PCR was carried out for 50 cycles with the following temperature profile: 15 sec 56° C., 30 sec 76° C., 30 sec 94° C. The reverse transcriptase reaction was deactivated for 5 min at 95° C. before use in the PCR reaction. The extent of the genomic DNA depletion is reported in the following table 3 in CT values:

TABLE 3

| | Difference–DNase/+DNase | | | | | |
|---|---|---|---|---|---|---|
| | 1 μg | 100 ng | 10 ng | 1 ng | 100 pg | 10 pg |
| RNA 1/DNA 1 | 20.6 | 18.7 | 18.1 | 17.8 | 14.2 | 5.4 |
| RNA 2/DNA 2 | 23.3 | 20.7 | 20.0 | 13.6 | 8.3 | 10.4 |
| RNA 2/DNA 1 | 23.1 | 21.7 | 21.4 | 18.8 | 14.8 | 12.1 |

The result shows that by use of RNase-free DNase I, whose incubation is carried out prior to the actual reverse transcriptase step, the genomic DNA is generally depleted more than 1000 times.

A further batch was used to demonstrate that the DNase step can also be integrated into the process of a so-called 1-step RT-PCR. In a 1-step RT-PCR reaction the whole reaction batch including all reagents necessary for the reverse transcriptase step and the subsequent PCR step are combined. The reaction is started with the reverse transcription and continues directly into the PCR step without opening the reaction vessel. The following example shows that a DNase step can also be introduced into such a continuous method scheme that does not allow further operator interaction.

EXAMPLE 7

In each case 20 ng total RNA from HeLa cells and 20 ng high molecular gDNA were used in each 1-step RT-PCR. 150 μM $CaCl_2$ were added to the reaction. Each reaction was carried out with the QuantiTect RT-PCR Kit (QIAGEN GmbH, Hilden, Germany), which contains all necessary reaction components such as reverse transcriptase, HotStar Taq DNA polymerase, reaction buffer and dNTPs. The reactions were initiated with and without DNase I. The reverse transcriptase was not used in reactions that were solely to detect genomic DNA in order not to obtain an additional signal from the cDNA. Reaction batches in which DNase I was used received 0.25 units DNase I. A transcript region for which identical sequences occur in genomic DNA was detected as target gene. The PCR products that were generated from genomic DNA and cDNA had the same size and consequently should be amplified and detected with the same efficiency.

The result is shown in FIG. 5 and can be summarised as follows. The CT value of genomic DNA increases through the use DNase by more than 6 cycles, which corresponds to a 100 fold gDNA degradation, whereas the CT value of cDNA changes only insignificantly. This leads to the conclusion that a gDNA removal step is also usable in 1-step RT-PCR and leads to a significant degradation of genomic DNA, whereas cDNA remains intact, or is only insignificantly degraded. The increase in the CT value on using RNA (cDNA) is essentially attributable to the depletion of the genomic DNA contained in the RNA sample.

The invention claimed is:

1. A method of analyzing RNA, comprising, degradation of double-stranded DNA and an RNA reaction, wherein the degradation of double-stranded DNA and the RNA reaction are carried out in the same reaction vessel at the same time and at the same temperature, wherein the degradation of double-stranded DNA is carried out with an enzyme with DNA double-strand-specific endonuclease activity, wherein the RNA reaction is a conversion reaction, wherein the RNA is used as a template for a polymerase reaction, and wherein the RNA is analyzed after the RNA reaction.

2. The method of claim 1, wherein the RNA reaction comprises a tagging, extension or modification of the RNA.

3. The method of claim 1, wherein the conversion reaction is a reverse transcription reaction.

4. A method of analyzing RNA, comprising, degradation of double-stranded DNA and an RNA reaction, wherein the degradation of double-stranded DNA and the RNA reaction are carried out in the same reaction vessel at the same time and at the same temperature, wherein the degradation of double-stranded DNA is carried out with an enzyme with DNA double-strand-specific endonuclease activity, wherein the RNA acts as a catalyst in the RNA reaction, thereby analyzing RNA.

5. The method of claim 1, wherein the RNA is involved in a binding reaction in the RNA reaction.

6. The method of claim 1, wherein the RNA reaction is a combined reaction, wherein at least two of the reactions selected from the group consisting of a tagging of the RNA, an extension of the RNA, a modification of the RNA, or a conversion reaction are involved.

7. The method of claim 1, wherein the degradation of DNA is carried out with an enzyme selected from the group consisting of DNase 1 and restriction endonucleases.

8. The method of claim 1, wherein the method is carried out at a pH value of between 6 and 10.

9. The method of claim 1, wherein the reaction comprises divalent cations.

10. The method of claim 9, wherein the divalent cations are selected from the group consisting of $Mg^{2+}$, $Mn^{2+}$ and $Ca^{2+}$.

11. A method of analyzing RNA, comprising, degradation of double-stranded DNA and an RNA reaction, wherein the degradation of double-stranded DNA and the RNA reaction are carried out in the same reaction vessel at the same time and at the same temperature, wherein the degradation of double-stranded DNA is carried out with an enzyme with DNA double-strand-specific endonuclease activity, wherein the RNA reaction is a specific degradation reaction, wherein the RNA is selectively degraded, and wherein the RNA is selectively degraded by a ribozyme, RNase H or by siRNA-induced RNA degradation, thereby analyzing RNA.

12. The method of claim 8, wherein the method is carried out at a pH value of between 7 and 9.

13. The method of claim 1, wherein the double stranded DNA is degraded by RNAse-free DNase I.

14. The method of claim 1, wherein the double-stranded DNA is degraded by a restriction endonuclease.

15. The method of claim 1, wherein the degradation of double stranded DNA is carried out in the presence of an RNAse inhibitor.

* * * * *